(12) United States Patent
Li et al.

(10) Patent No.: US 8,119,658 B2
(45) Date of Patent: Feb. 21, 2012

(54) TRIAZOLOPYRIDINE 11-BETA HYDROXYSTEROID DEHYDROGENASE TYPE I INHIBITORS

(75) Inventors: Jun Li, Princeton, NJ (US); Jeffrey A. Robl, Newtown, PA (US); James J. Li, Pennington, NJ (US); Lawrence J. Kennedy, Titusville, NJ (US); Haixia Wang, Princeton, NJ (US); Jie Jack Li, Killingworth, CT (US); Xinhua Qian, Flemington, NJ (US); Rajendra P. Deshpande, Hillsborough, NJ (US); Laxma R. Kolla, Princeton Junction, NJ (US); Reginald O. Cann, Princeton Junction, NJ (US); Chenkou Wei, Princeton Junction, NJ (US); Michael Galella, Kendall Park, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 353 days.

(21) Appl. No.: 12/206,801

(22) Filed: Sep. 9, 2008

(65) Prior Publication Data

US 2009/0093516 A1    Apr. 9, 2009

Related U.S. Application Data

(60) Provisional application No. 60/976,506, filed on Oct. 1, 2007.

(51) Int. Cl.
| | |
|---|---|
| A61K 31/437 | (2006.01) |
| C07D 471/04 | (2006.01) |
| A61P 3/04 | (2006.01) |
| A61P 3/10 | (2006.01) |
| A61P 9/12 | (2006.01) |
| A61P 3/00 | (2006.01) |

(52) U.S. Cl. ........................ 514/303; 546/119
(58) Field of Classification Search .................. 546/119; 514/303
See application file for complete search history.

(56) References Cited

U.S. PATENT DOCUMENTS

| | | | |
|---|---|---|---|
| 3,083,204 A | 3/1963 | Klavehn et al. | |
| 3,597,423 A | 8/1971 | Wiedemann et al. | |
| 4,358,453 A | 11/1982 | Bristol et al. | |
| 4,691,051 A | 9/1987 | Georgiev et al. | |
| 5,236,917 A | 8/1993 | Dunlap et al. | |
| 6,043,369 A * | 3/2000 | Schefczik | 546/119 |
| 6,242,615 B1 | 6/2001 | Pelleter et al. | |
| 6,696,464 B2 | 2/2004 | McClure et al. | |
| 6,730,690 B2 | 5/2004 | Olson et al. | |
| 6,740,647 B1 | 5/2004 | Baucke et al. | |
| 7,144,907 B2 | 12/2006 | Wallace et al. | |
| 7,230,099 B2 | 6/2007 | Wallace et al. | |
| 2003/0114460 A1 | 6/2003 | Hughes et al. | |
| 2004/0053959 A1 | 3/2004 | Buzon, Sr. et al. | |
| 2004/0072830 A1 | 4/2004 | Okada et al. | |
| 2004/0133011 A1 | 7/2004 | Waddell et al. | |
| 2004/0209858 A1 | 10/2004 | Bennani et al. | |
| 2005/0049276 A1 | 3/2005 | Kaufman et al. | |
| 2005/0049419 A1 | 3/2005 | Wallace et al. | |
| 2005/0054701 A1 | 3/2005 | Wallace et al. | |
| 2005/0070720 A1 | 3/2005 | Balkovec et al. | |
| 2005/0075365 A1 | 4/2005 | Braganza et al. | |
| 2005/0113283 A1 | 5/2005 | Solow-Cordero et al. | |
| 2005/0229333 A1 | 10/2005 | Glenn, Jr. et al. | |
| 2005/0277647 A1 | 12/2005 | Link et al. | |
| 2006/0030610 A1 | 2/2006 | Koch et al. | |
| 2006/0035922 A1 | 2/2006 | Mathias et al. | |
| 2006/0079506 A1 | 4/2006 | Linders et al. | |
| 2006/0094699 A1 | 5/2006 | Kampen et al. | |
| 2006/0111348 A1 | 5/2006 | Kampen et al. | |
| 2006/0111366 A1 | 5/2006 | Andersen et al. | |
| 2006/0148871 A1 | 7/2006 | Rohde et al. | |
| 2006/0149070 A1 | 7/2006 | Rohde et al. | |
| 2006/0247245 A1 | 11/2006 | Xu | |
| 2006/0281750 A1 | 12/2006 | Li et al. | |
| 2006/0287357 A1 | 12/2006 | Li et al. | |
| 2008/0234249 A1 | 9/2008 | Ye et al. | |
| 2009/0124609 A1 | 5/2009 | Albrecht et al. | |
| 2009/0124612 A1 | 5/2009 | Albrecht et al. | |

FOREIGN PATENT DOCUMENTS

EP    0 130 882    1/1985

(Continued)

OTHER PUBLICATIONS

Dawood et al., Bollettino Chimico Farmaceutico (2001), 140(3), 149-154.*
El-Moybayed et al., Egyptian Journal of Pharmaceutical Sciences (1989), 30(1-4), 329-37.*
El-Kerdawy et al., Oriental Journal of Chemistry (1990), 6(2), 115-19.*
El-Salman et al., Pharmazie (1999), 54(3), 178-183.*
El-Nabawia et al., Alexandria Journal of Pharmaceutical Sciences (1999), 13(2), 145-148.*

(Continued)

*Primary Examiner* — D M Seaman
*Assistant Examiner* — Niloofar Rahmani
(74) *Attorney, Agent, or Firm* — Terence J. Bogie

(57) ABSTRACT

Novel compounds are provided which are 11-beta-hydroxysteroid dehydrogenase type I inhibitors. 11-beta-hydroxysteroid dehydrogenase type I inhibitors are useful in treating, preventing, or slowing the progression of diseases requiring 11-beta-hydroxysteroid dehydrogenase type I inhibitor therapy. These novel compounds of formula I:

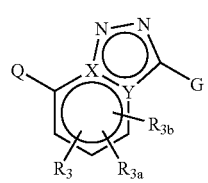

or stereoisomers or pharmaceutically acceptable salts thereof, wherein G, Q, X, Y, $R_3$, $R_{3a}$, and $R_{3b}$ are defined herein.

20 Claims, 8 Drawing Sheets

FOREIGN PATENT DOCUMENTS

| | | |
|---|---|---|
| EP | 0 430 385 | 6/1991 |
| EP | 430385 * | 6/1991 |
| EP | 0 699 438 | 3/1996 |
| JP | 47-47396 | 11/1972 |
| JP | 2000-319277 | 11/2000 |
| JP | 2002-356458 | 12/2002 |
| WO | WO 92/18132 | 10/1992 |
| WO | WO 95/09634 | 4/1995 |
| WO | WO 97/33859 | 9/1997 |
| WO | WO 97/47601 | 12/1997 |
| WO | WO 98/05336 | 2/1998 |
| WO | WO 98/25923 | 6/1998 |
| WO | WO 98/43946 | 10/1998 |
| WO | WO 99/09984 | 3/1999 |
| WO | WO 99/31075 | 6/1999 |
| WO | WO 99/37668 | 7/1999 |
| WO | WO 00/66572 | 11/2000 |
| WO | WO 01/60818 | 8/2001 |
| WO | WO 02/12236 | 2/2002 |
| WO | WO 02/076973 | 10/2002 |
| WO | WO 03/063845 | 8/2003 |
| WO | WO 03/065983 | 8/2003 |
| WO | WO 03/104207 | 12/2003 |
| WO | WO 03/104208 | 12/2003 |
| WO | WO 2004/056744 | 7/2004 |
| WO | WO 2004/056745 | 7/2004 |
| WO | WO 2004/058730 | 7/2004 |
| WO | WO 2004/058741 | 7/2004 |
| WO | WO 2004/065351 | 8/2004 |
| WO | WO 2004/089380 | 10/2004 |
| WO | WO 2004/089415 | 10/2004 |
| WO | WO 2004/089416 | 10/2004 |
| WO | WO 2004/089470 | 10/2004 |
| WO | WO 2004/089896 | 10/2004 |
| WO | WO 2004/106294 | 12/2004 |
| WO | WO 2005/046685 | 5/2005 |
| WO | WO 2005/047250 | 5/2005 |
| WO | WO 2005/073200 | 8/2005 |
| WO | WO 2005/097052 | 10/2005 |
| WO | WO 2006/015737 | 2/2006 |
| WO | WO 2006/018727 | 2/2006 |
| WO | WO 2006/018735 | 2/2006 |
| WO | WO 2006/026754 | 3/2006 |
| WO | WO 2006/030805 | 3/2006 |
| WO | WO 2006/034804 | 4/2006 |
| WO | WO 2006/036816 | 4/2006 |
| WO | WO 2006/036932 | 4/2006 |
| WO | WO 2006/038116 | 4/2006 |
| WO | WO 2006/038738 | 4/2006 |
| WO | WO 2006/040039 | 4/2006 |
| WO | WO 2006/042599 | 4/2006 |
| WO | WO 2006/044687 | 4/2006 |
| WO | WO 2006/044821 | 4/2006 |
| WO | WO 2006/044958 | 4/2006 |
| WO | WO 2006/047317 | 5/2006 |
| WO | WO 2006/047631 | 5/2006 |
| WO | WO 2006/048330 | 5/2006 |
| WO | WO 2006/048331 | 5/2006 |
| WO | WO 2006/049952 | 5/2006 |
| WO | WO 2006/058752 | 6/2006 |
| WO | WO 2006/069787 | 7/2006 |
| WO | WO 2006/074244 | 7/2006 |
| WO | WO 2006/080533 | 8/2006 |
| WO | WO 2006/135667 | 12/2006 |
| WO | WO 2006/135795 | 12/2006 |
| WO | WO 2006/138657 | 12/2006 |
| WO | WO 2007/007688 | 1/2007 |
| WO | WO 2007/038452 | 4/2007 |
| WO | WO 2007/047625 | 4/2007 |
| WO | WO 2007/068330 | 6/2007 |
| WO | WO 2007/113226 | 10/2007 |
| WO | WO 2008/063287 | 5/2008 |
| WO | WO 2008/066789 | 6/2008 |
| WO | WO 2008/124085 | 10/2008 |
| WO | WO 2008/124153 | 10/2008 |

OTHER PUBLICATIONS

Abarca, B. et al., "Triazolopyridines. Part 24: New polynitrogenated potential helicating ligands", Tetrahedron, vol. 60, pp. 5785-5792 (2004).

Bhattacharyya, K.C., "Formation and Reaction of ββ-Disubstituted α-Keto-Glutaric Acids", Current Science, No. 11, pp. 312-313 (1952).

Jones, G. et al., "Triazolopyridines. 18. Nucleophilic Substitution Reactions on Triazolopyridines; A New Route to 2,2'-Bipyridines", Tetrahedron, vol. 53, No. 24, pp. 8257-8268 (1997).

Latham, E.J. et al., "Fluorescence Studies of some 1,2,3-Triazolo[1,5-α]pyridine and Imidazo[1,2-α]pyridine Esters and their Vinylogues", J. Heterocyclic Chem., vol. 33, pp. 991-992 (1996).

* cited by examiner

Experimental (top) and simulated (bottom) powder patterns for Form N-1 of Example 1G DSC for Form N-1 of Example 1G TGA for Form N-1 of Example 1G Moisture sorption isotherm of Form N-1 of Example 1G DSC for Form N-2 of Example 1G TGA for Form N-2 of Example 1G Experimental (top) and simulated (bottom) powder patterns for Form N-1 of Example 1H

TRIAZOLOPYRIDINE 11-BETA HYDROXYSTEROID DEHYDROGENASE TYPE I INHIBITORS

CROSS-REFERENCES TO RELATED APPLICATION

This application claims priority benefit under Title 35 §119(e) of U.S. provisional Application 60/976,506, filed Oct. 1, 2007, the contents of which are herein incorporated by reference in its entirety.

BACKGROUND OF THE INVENTION

The steroid hormone cortisol is a key regulator of many physiological processes. However, an excess of cortisol, as occurs in Cushing's Disease, provokes severe metabolic abnormalities including: type 2 diabetes, cardiovascular disease, obesity, and osteoporosis. Many patients with these diseases, however, do not show significant increases in plasma cortisol levels. In addition to plasma cortisol, individual tissues can regulate their glucocorticoid tone via the in situ conversion of inactive cortisone to the active hormone cortisol. Indeed, the normally high plasma concentration of cortisone provides a ready supply of precursor for conversion to cortisol via the intracellular enzyme 11-beta-hydroxysteroid dehydrogenase type I (11beta-HSD1).

11beta-HSD1 is a member of the short chain dehydrogenase superfamily of enzymes. By catalyzing the conversion of cortisone to cortisol, 11beta-HSD1 controls the intracellular glucocorticoid tone according to its expression and activity levels. In this manner, 11beta-HSD1 can determine the overall metabolic status of the organ. 11beta-HSD1 is expressed at high levels in the liver and at lower levels in many metabolically active tissues including the adipose, the CNS, the pancreas, and the pituitary. Taking the example of the liver, it is predicted that high levels of 11beta-HSD1 activity will stimulate gluconeogenesis and overall glucose output. Conversely, reduction of 11beta-HSD1 activity will down regulate gluconeogenesis resulting in lower plasma glucose levels.

Various studies have been conducted that support this hypothesis. For example, transgenic mice expressing 2× the normal level of 11beta-HSD1 in only the adipose tissue show abdominal obesity, hyperglycemia, and insulin resistance. (Masuzaki, H. et al., "A Transgenic Model of Visceral Obesity and the Metabolic Syndrome", *Science*, 294:2166-2170 (2001). Conversely, when the 11beta-HSD1 gene is ablated by homologous recombination, the resulting mice are resistant to diet induced obesity and the accompanying dysregulation of glucose metabolism (Morton, N. M. et al., "Novel Adipose Tissue-Mediated Resistance to Diet-induced Visceral Obesity in 11β-Hydroxysteroid Dehydrogenase Type 1-Deficient Mice", *Diabetes*, 53:931-938 (2004). In addition, treatment of genetic mouse models of obesity and diabetes (ob/ob, db/db and KKAy mice) with a specific inhibitor of 11beta-HSD1 causes a decrease in glucose output from the liver and an overall increase in insulin sensitivity (Alberts, P. et al., "Selective Inhibition of 11β-Hydroxysteroid Dehydrogenase Type I Improves Hepatic Insuling Sensitivity in Hyperglycemic Mice Strains", *Endocrinology*, 144:4755-4762 (2003)). Furthermore, inhibitors of 11beta-HSD1 have been shown to be effective in treating metabolic syndrome and atherosclerosis in high fat fed mice (Hermanowski-Vosatka et al., *J. Exp. Med.*, 202(4):517-527 (2002)). Based in part on these studies, it is believed that local control of cortisol levels is important in metabolic diseases in these model systems. In addition, the results of these studies also suggest that inhibition of 11beta-HSD1 will be a viable strategy for treating metabolic diseases such as type 2 diabetes, obesity, and the metabolic syndrome.

Lending further support to this idea are the results of a series of preliminary clinical studies. For example, several reports have shown that adipose tissue from obese individuals has elevated levels of 11beta-HSD1 activity. In addition, studies with carbenoxolone, a natural product derived from licorice that inhibits both 11beta-HSD1 and 11beta-HSD2 (converts cortisol to cortisone in kidney) have shown promising results. A seven day, double blind, placebo controlled, cross over study with carbenoxolone in mildly overweight individuals with type 2 diabetes showed that patients treated with the inhibitor, but not the placebo group, displayed a decrease in hepatic glucose production (Andrews, R. C. et al., *J. Clin. Endocrinol. Metab.*, 88:285-291 (2003)). This observation is consistent with the inhibition of 11beta-HSD1 in the liver. The results of these preclinical and early clinical studies strongly support the concept that treatment with a potent and selective inhibitor of 11beta-HSD1 will be an efficacious therapy in patients afflicted with type 2 diabetes, obesity, and the metabolic syndrome.

SUMMARY OF THE INVENTION

In accordance with the present invention, bicyclic and related compounds are provided that have the general structure of formula I:

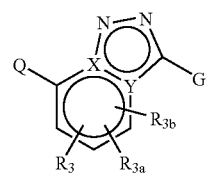

wherein G, Q, X, Y, $R_3$, $R_{3a}$, and $R_{3b}$ are defined below.

The compounds of the present invention inhibit the activity of the enzyme 11-beta-hydroxysteroid dehydrogenase type I. Consequently, the compounds of the present invention may be used in the treatment of multiple diseases or disorders associated with 11-beta-hydroxysteroid dehydrogenase type I, such as diabetes and related conditions, microvascular complications associated with diabetes, the macrovascular complications associated with diabetes, cardiovascular diseases, Metabolic Syndrome and its component conditions, inflammatory diseases and other maladies. Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermittent claudication), abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

The present invention provides for compounds of formula I, pharmaceutical compositions employing such compounds, and for methods of using such compounds. In particular, the present invention provides a pharmaceutical composition comprising a therapeutically effective amount of a compound of formula I alone or in combination with a pharmaceutically acceptable carrier.

Further, in accordance with the present invention, a method is provided for preventing, inhibiting, or treating the progression or onset of diseases or disorders associated with the activity of the enzyme 11-beta-hydroxysteroid dehydrogenase type I, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

Further, the present invention provides for crystalline forms of the compounds of formula I, pharmaceutical compositions employing such crystalline forms, and for methods of using such forms.

Furthermore, the present invention provides for processes for preparing compounds of formula I. These processes may be characterized, without limitation, by a) facile adaptation to larger scale production, such as pilot plant or manufacturing scales; b) process steps and/or techniques enabling improvements in the purity (including chiral purity), stability and/or ease of handling of intermediates and/or final compounds; and/or c) fewer process steps.

DESCRIPTION OF THE INVENTION

Figure 1:
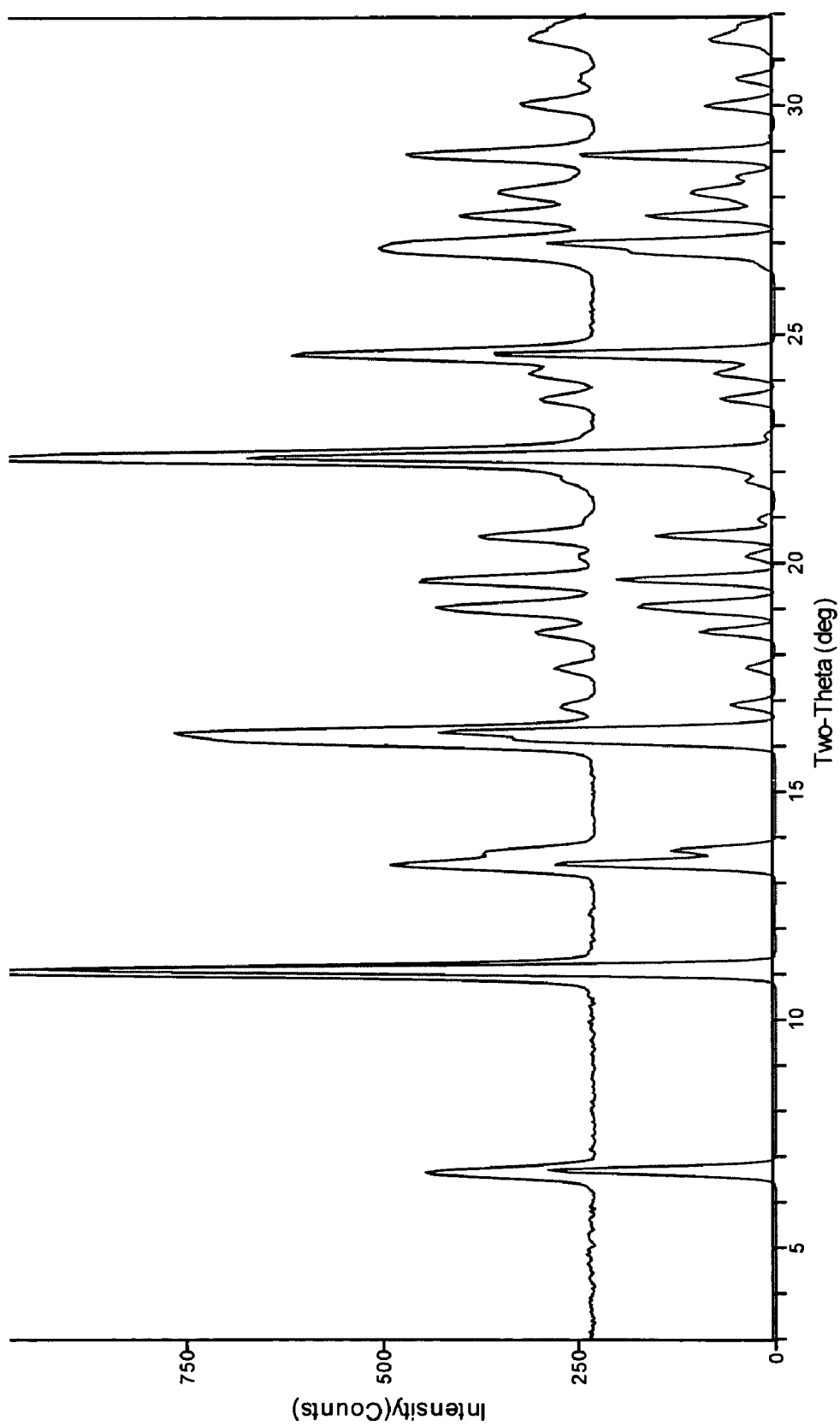
FIG. 1 shows observed (experimental at room temperature) and simulated (calculated at room temperature) powder x-ray diffraction patterns (Cu Kα$\lambda$=1.5418 Å) of an N-1 crystalline form of a salt of a compound of Formula I.

In accordance with the present invention, compounds of formula I

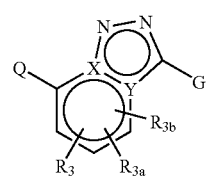

enantiomers, diastereomers, or salts thereof wherein:

Q is L, $L_{aa}$ or $L_{ee}$;
X is C and Y is N; or
X is N and Y is C;
G is $R_4$, $R_{4aa}$ or $R_{4ee}$;
L is -alkenyl-$(W_1)_n$, -cycloalkyl-$(W_1)_n$ or -alkyl-$(W_2)_n$;
$L_{aa}$ is -alkenyl-$(W_1)_n$ or -alkyl-$(W_{2aa})_n$;
$L_{ee}$ is -alkenyl-$(W_{1ee})_n$, -cycloalkyl-$(W_1)_n$ or -alkyl-$(W_{2ee})_n$;
n is 1 to 3;
$W_1$, at each occurrence, is independently halogen, —OH, —CN, —CO$_2$R$_6$, —CONR$_8$R$_{8a}$, —OCONR$_8$R$_{8a}$, —SO$_2$NR$_8$R$_{8a}$, —SOR$_6$, —SO$_2$R$_6$, —NR$_9$SO$_2$R$_{9a}$, —NR$_9$CO$_2$R$_{9a}$, —NR$_9$COR$_{9a}$, alkyl, cycloalkyl, haloalkyl, alkoxy, aryloxy, haloalkoxy, alkylthio, arylthio, arylsulfonyl, alkylamino, amino, aminoalkyl, arylamino or heteroarylamino;
$W_{1ee}$ is independently halogen, —OH, —CN, —CO$_2$R$_6$, —CONR$_8$R$_{8a}$, —OCONR$_8$R$_{8a}$, —SO$_2$NR$_8$R$_{8a}$, —SOR$_6$, —SO$_2$R$_6$, —NR$_9$SO$_2$R$_{9a}$, —NR$_9$CO$_2$R$_{9a}$, —NR$_9$COR$_{9a}$, cycloalkyl, alkyl, haloalkyl, alkoxy, aryloxy, haloalkoxy, alkylthio, arylthio, arylsulfonyl, alkylamino, amino, aminoalkyl, arylamino or heteroarylamino;
$W_2$ is independently halogen, —OH, —CO$_2$H, —CN, —CO$_2$R$_6$, —CONR$_8$R$_{8a}$, —OCOR$_6$, —OCONR$_8$R$_{8a}$, —SO$_2$NR$_8$R$_{8a}$, —SO-alkyl, —SO$_2$-alkyl, —NR$_9$SO$_2$R$_{9a}$, —NR$_9$CO$_2$R$_{9a}$, —NR$_9$COR$_{9a}$, cycloalkyl, alkyl, haloalkyl, alkoxy, alkenyl, haloalkoxy, alkylthio, alkylamino, amino or aminoalkyl;
$W_{2aa}$ is independently halogen, —OH, —CN, —CO$_2$H, —CO$_2$R$_6$, —CONR$_8$R$_{8a}$, —OCOR$_6$, —OCONR$_8$R$_{8a}$, —SO$_2$NR$_8$R$_{8a}$, —SO-alkyl, —SO$_2$-alkyl, —NR$_9$SO$_2$R$_{9a}$, —NR$_9$CO$_2$R$_{9a}$, —NR$_9$COR$_{9a}$, —OR$_{9b}$OR$_{9b}$Si(R$_{9b}$)$_3$, cycloalkyl, alkyl, haloalkyl, alkoxy, alkenyl, haloalkoxy, alkylthio, alkylamino, amino or aminoalkyl;
$W_{2ee}$ is independently halogen, —OH, —CN, —CO$_2$H, —CO$_2$R$_6$, —CONR$_8$R$_{8a}$, —OCOR$_6$, —OCONR$_8$R$_{8a}$, —SO$_2$NR$_8$R$_{8a}$, —SO-alkyl, —SO$_2$-alkyl, —NR$_9$SO$_2$R$_{9a}$, —NR$_9$CO$_2$R$_{9a}$, —NR$_9$COR$_{9a}$, cycloalkyl, alkyl, haloalkyl, alkenyl, haloalkoxy, alkylthio, amino, aminoalkyl, aryl, heteroaryl or heterocyclyl, wherein the aryl, heteroaryl or heterocyclyl may be optionally substituted with $R_7$, $R_{7a}$, $R_{7b}$, and $R_{7c}$; provided that $W_{2aa}$ or $W_{2ee}$ are not only halogen or alkyl;
$R_3$, $R_{3a}$ and $R_{3b}$ are independently hydrogen, halogen, —OH, —CN, —NO$_2$, —CO$_2$R$_{8a}$, —CONR$_8$R$_{8a}$, —SO$_2$NR$_8$R$_{8a}$, —SOR$_{8a}$, —SO$_2$R$_{8a}$, —NR$_8$SO$_2$R$_6$, —NR$_8$CO$_2$R$_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is alkyl, cycloalkyl or heterocyclyl, all of which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_8R_{8a}$, —$CONR_8R_{8a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4aa}$ is cycloalkyl, which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_8R_{8a}$, —$CONR_8R_{8a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4ee}$ is alkyl or cycloalkyl, both of which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_8R_{8a}$, —$CONR_8R_{8a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_{8a}$, $CO_2R_{8a}$, $SO_2NR_8R_{8a}$, or $SO_2R_{8a}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, cyanoalkyl, alkoxy, haloalkoxy, aryl, aryloxy, arylaryl, arylalkyl, arylalkyloxy, alkenyl, cycloalkyl, cycloalkylalkyl, cycloalkylalkyloxy, amino, —OH, —$CO_2R_8$, —$CONR_8R_{8a}$, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, alkylsilicaalkyloxy, —$SO_2R_{9b}$—$NO_2$, —CN or thiol, wherein the aryl or heteroaryl may be optionally substituted with $R_{10}$, $R_{10a}$, $R_{10b}$, and $R_{10c}$;

$R_8$ and $R_{8a}$, at each occurrence, is independently hydrogen, alkyl, cycloalkyl, aryl, heteroaryl or heterocyclyl, all of which may be optionally substituted with $R_{10}$, $R_{10a}$, $R_{10b}$, and $R_{10c}$;

or alternatively $R_8$ and $R_{8a}$ can be taken together with the nitrogen to which they are attached to form a heterocyclyl ring containing 1, 2, 3, or 4 heteroatoms independently selected from the group consisting of N, NH, O and S, which may be optionally substituted with $R_{10}$, $R_{10a}$, $R_{10b}$, and $R_{10c}$;

$R_9$ and $R_{9a}$, at each occurrence, is independently hydrogen, alkyl, cycloalkyl, aryl, arylalkyl, heteroaryl or heterocyclyl, all of which may be optionally substituted with $R_{10}$, $R_{10a}$, $R_{10b}$, and $R_{10c}$;

$R_{9b}$, at each occurrence, is independently alkyl, cycloalkyl, aryl or heteroaryl, all of which may be optionally substituted with $R_{10}$, $R_{10a}$, $R_{10b}$, and $R_{10c}$; and $R_{10}$, $R_{10a}$, $R_{10b}$, and $R_{10c}$, at each occurrence, are independently halo, alkyl, haloalkyl, cyanoalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol;

provided that:

(a) $W_1$, $W_{1ee}$, $W_2$, or $W_{2aa}$ is not cycloalkyl when n is 1 and $R_4$, $R_{4aa}$ or $R_{4ee}$ are cycloalkyl;

(b) $W_{2ee}$ is not cycloalkyl, aryl, heteroaryl or heterocyclyl when n is 1 and $R_{4ee}$ is cycloalkyl;

(c) $R_7$, $R_{7a}$, $R_{7b}$, and $R_{7c}$ must be substituted with at least one $R_{10}$, $R_{10a}$, $R_{10b}$, or $R_{10c}$ when (i) $L_{ee}$ is cycloalkyl, (ii) $R_{4ee}$ is cycloalkyl substituted with aryl, heterocyclyl or heteroaryl, (iii) the aryl, heteroaryl or heterocyclyl is substituted with $R_7$, $R_{7a}$, $R_{7b}$, or $R_{7c}$; and (iv) $R_7$, $R_{7a}$, $R_{7b}$, and $R_{7c}$ is aryl, heteroaryl or heterocyclyl;

(d) $L_{aa}$ and $L_{ee}$ are not $C_{1-3}$alkyl or halo$C_{1-3}$alkyl when $R_{4aa}$ or $R_{4ee}$ are substituted with an optionally substituted aryl moiety; and (e) $W_{2ee}$ is not halogen, alkyl, haloalkyl or aryl when $R_{4ee}$ is alkyl.

In another embodiment, compounds are those in which the compound is a compound of formula Iaa, Idd or Iee:

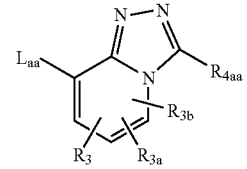

Iaa

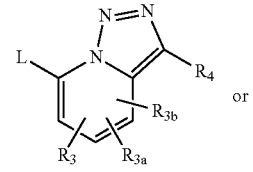

Idd or

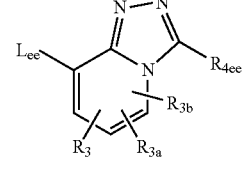

Iee provided that:

(a) $W_1$, $W_{1ee}$, $W_2$, or $W_{2aa}$ is not cycloalkyl when n is 1 and $R_4$, $R_{4aa}$ or $R_{4ee}$ are cycloalkyl;

(b) $W_{2ee}$ is not cycloalkyl, aryl, heteroaryl or heterocyclyl when n is 1 and $R_{4ee}$ is cycloalkyl;

(c) $R_7$, $R_{7a}$, $R_{7b}$, and $R_{7c}$ must be substituted with at least one $R_{10}$, $R_{10a}$, $R_{10b}$, or $R_{10c}$ when (i) $L_{ee}$ is cycloalkyl, (ii) $R_{4ee}$ is cycloalkyl substituted with aryl, heterocyclyl or heteroaryl, (iii) the aryl, heteroaryl or heterocyclyl is substituted with $R_7$, $R_{7a}$, $R_{7b}$, or $R_{7c}$; and (iv) $R_7$, $R_{7a}$, $R_{7b}$, and $R_{7c}$ is aryl, heteroaryl or heterocyclyl;

(d) $L_{aa}$ and $L_{ee}$ are not $C_{1-3}$alkyl or halo$C_{1-3}$alkyl when $R_{4aa}$ or $R_{4ee}$ are substituted with an optionally substituted aryl moiety; and (e) $W_{2ee}$ is not halogen, alkyl, haloalkyl or aryl when $R_{4ee}$ is alkyl.

In another embodiment, compounds are those in which:

L is -alkenyl-$(W_1)_n$ or -alkyl-$(W_2)_n$;

$L_{aa}$ is -alkenyl-$(W_1)_n$ or -alkyl-$(W_{2aa})_n$;

$L_{ee}$ is -alkenyl-$(W_{1ee})_n$, -cycloalkyl-$(W_1)_n$ or -alkyl-$(W_{2ee})_n$;

n is 1 to 3;

$W_1$, at each occurrence, is independently halogen, —OH, —CN, —$CO_2R_6$, —$CONR_8R_{8a}$, —$OCONR_8R_{8a}$, —$SO_2NR_8R_{8a}$, —$SOR_6$, —$SO_2R_6$, —$NR_9SO_2R_{9a}$, —$NR_9CO_2R_{9a}$, alkyl, cycloalkyl, haloalkyl, alkoxy, aryloxy, haloalkoxy, alkylthio, arylthio, arylsulfonyl, alkylamino, aminoalkyl, arylamino or heteroarylamino;

$W_{1ee}$ is independently halogen, —OH, —CN, —$CO_2R_6$, —$CONR_8R_{8a}$, —$OCONR_8R_{8a}$, —$SO_2NR_8R_{8a}$, —$SOR_6$, —$SO_2R_6$, —$NR_9SO_2R_{9a}$, —$NR_9CO_2R_{9a}$, cycloalkyl, alkyl, haloalkyl, alkoxy, aryloxy, haloalkoxy, alkylthio, arylthio, arylsulfonyl, alkylamino, aminoalkyl, arylamino or heteroarylamino;

$W_2$ is independently halogen, —OH, —$CO_2H$, —CN, —$CO_2R_6$, —$CONR_8R_{8a}$, —$OCOR_6$, —$OCONR_8R_{8a}$, —$SO_2NR_8R_{8a}$, —SO-alkyl, —$SO_2$-alkyl, —$NR_9SO_2R_{9a}$, —$NR_9CO_2R_{9a}$, —$NR_9COR_{9a}$, cycloalkyl, alkyl, haloalkyl, alkoxy, alkenyl, haloalkoxy, alkylthio, alkylamino, amino or aminoalkyl;

$W_{2aa}$ is independently halogen, —OH, —CN, —$CO_2H$, —$CO_2R_6$, —$CONR_8R_{8a}$, —$OCOR_6$, —$OCONR_8R_{8a}$, —$SO_2NR_8R_{8a}$, —SO-alkyl, —$SO_2$-alkyl, —$NR_9SO_2R_{9a}$, —$NR_9CO_2R_{9a}$, —$NR_9COR_{9a}$, —$OR_{9b}OR_{9b}Si(R_{9b})_3$, cycloalkyl, alkyl, haloalkyl, alkoxy, alkenyl, haloalkoxy, alkylthio, alkylamino, amino or aminoalkyl;

$W_{2ee}$ is independently halogen, —OH, —CN, —$CO_2H$, —$CO_2R_6$, —$CONR_8R_{8a}$, —$OCOR_6$, —$OCONR_8R_{8a}$, —$SO_2NR_8R_{8a}$, —SO-alkyl, —$SO_2$-alkyl, —$NR_9SO_2R_{9a}$, —$NR_9CO_2R_{9a}$, —$NR_9COR_{9a}$, cycloalkyl, alkyl, haloalkyl, alkenyl, haloalkoxy, alkylthio, aminoalkyl, aryl, heteroaryl or heterocyclyl, wherein the aryl, heteroaryl or heterocyclyl may be optionally substituted with $R_7$, $R_{7a}$, $R_{7b}$, and $R_{7c}$; provided that $W_{2aa}$ or $W_{2ee}$ are not only halogen;

$R_3$, $R_{3a}$ and $R_{3b}$ are independently hydrogen, halogen, —OH, —CN, —$NO_2$, —$CO_2R_{8a}$, —$CONR_8R_{8a}$, —$SO_2NR_8R_{8a}$, —$SOR_{8a}$, —$SO_2R_{8a}$, —$NR_8SO_2R_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is alkyl or cycloalkyl, both of which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_8R_{8a}$, —$CONR_8R_{8a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4aa}$ is cycloalkyl, which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_8R_{8a}$, —$CONR_8R_{8a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4ee}$ is alkyl or cycloalkyl, both of which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_8R_{8a}$, —$CONR_8R_{8a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_{8a}$ or $CO_2R_{8a}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, cyanoalkyl, alkoxy, haloalkoxy, aryl, aryloxy, arylaryl, arylalkyl, arylalkyloxy, alkenyl, cycloalkyl, cycloalkylalkyl, cycloalkylalkyloxy, amino, —OH, —$CO_2R_8$, —$CONR_8R_{8a}$, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$SO_2R_{9b}$—$NO_2$, —CN or thiol, wherein the aryl or heteroaryl may be optionally substituted with $R_{10}$, $R_{10a}$, $R_{10b}$, and $R_{10c}$;

$R_8$ and $R_{8a}$, at each occurrence, is independently hydrogen, alkyl, cycloalkyl, aryl, heteroaryl or heterocyclyl, all of which may be optionally substituted with $R_{10}$, $R_{10a}$, $R_{10b}$, and $R_{10c}$;

or alternatively $R_8$ and $R_{8a}$ can be taken together with the nitrogen to which they are attached to form a heterocyclyl ring containing 1, 2, 3, or 4 heteroatoms independently selected from the group consisting of N, NH, O and S, which may be optionally substituted with $R_{10}$, $R_{10a}$, $R_{10b}$, and $R_{10c}$;

$R_9$ and $R_{9a}$, at each occurrence, is independently hydrogen, alkyl, cycloalkyl, aryl, arylalkyl, heteroaryl or heterocyclyl, all of which may be optionally substituted with $R_{10}$, $R_{10a}$, $R_{10b}$, and $R_{10c}$;

$R_{9b}$, at each occurrence, is independently alkyl, cycloalkyl, aryl or heteroaryl, all of which may be optionally substituted with $R_{10}$, $R_{10a}$, $R_{10b}$, and $R_{10c}$;

$R_{10}$, $R_{10a}$, $R_{10b}$, and $R_{10c}$, at each occurrence, are independently halo, alkyl, haloalkyl, cyanoalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol;

provided that:

(a) $W_1$, $W_{1ee}$, $W_2$, or $W_{2aa}$ is not cycloalkyl when n is 1 and $R_4$, $R_{4aa}$ or $R_{4ee}$ are cycloalkyl;

(b) $W_{2ee}$ is not cycloalkyl, aryl, heteroaryl or heterocyclyl when n is 1 and $R_{4ee}$ is cycloalkyl;

(c) $R_7$, $R_{7a}$, $R_{7b}$, and $R_{7c}$ must be substituted with at least one $R_{10}$, $R_{10a}$, $R_{10b}$, or $R_{10c}$ when (i) $L_{ee}$ is cycloalkyl, (ii) $R_{4ee}$ is cycloalkyl substituted with aryl, heterocyclyl or heteroaryl, (iii) the aryl, heteroaryl or heterocyclyl is substituted with $R_7$, $R_{7a}$, $R_{7b}$, or $R_{7c}$; and (iv) $R_7$, $R_{7a}$, $R_{7b}$, and $R_{7c}$ is aryl, heteroaryl or heterocyclyl;

(d) $L_{aa}$ and $L_{ee}$ are not $C_{1-3}$alkyl or halo$C_{1-3}$alkyl when $R_{4aa}$ or $R_{4ee}$ are substituted with an optionally substituted aryl moiety; and (e) $W_{2ee}$ is not halogen, alkyl, haloalkyl or aryl when $R_{4ee}$ is alkyl.

In another embodiment, compounds are those in which:

L is -alkenyl-$(W_1)_n$ or -alkyl-$(W_2)_n$;

$L_{aa}$ is -alkenyl-$(W_1)_n$ or -alkyl-$(W_{2aa})_n$;

$L_{ee}$ is -alkenyl-$(W_{1ee})_n$, -cycloalkyl-$(W_1)_n$ or -alkyl-$(W_{2ee})_n$;

n is 1 to 3;

$W_1$, at each occurrence, is independently halogen, —OH, —CN, —$CO_2R_6$, —$CONR_8R_{8a}$, —$OCONR_8R_{8a}$, —$SO_2NR_8R_{8a}$, —$SOR_6$, —$SO_2R_6$, —$NR_9SO_2R_{9a}$, alkyl, haloalkyl, alkoxy, aryloxy, haloalkoxy, alkylthio, arylthio, arylsulfonyl, alkylamino, aminoalkyl, arylamino or heteroarylamino;

$W_{1ee}$ is independently halogen, —OH, —CN, —$CO_2R_6$, —$CONR_8R_{8a}$, —$OCONR_8R_{8a}$, —$SO_2NR_8R_{8a}$, —$SOR_6$, —$SO_2R_6$, —$NR_9SO_2R_{9a}$, alkyl, haloalkyl, alkoxy, aryloxy, haloalkoxy, alkylthio, arylthio, arylsulfonyl, alkylamino, aminoalkyl, arylamino or heteroarylamino;

$W_2$ is independently halogen, —OH, —$CO_2H$, —CN, —$CO_2R_6$, —$CONR_8R_{8a}$, —$OCOR_6$, —$OCONR_8R_{8a}$, —$SO_2NR_8R_{8a}$, —SO-alkyl, —$SO_2$-alkyl, —$NR_9SO_2R_{9a}$, —$NR_9COR_{9a}$, alkyl, haloalkyl, alkoxy, alkenyl, haloalkoxy, alkylthio, alkylamino, amino or aminoalkyl;

$W_{2aa}$ is independently halogen, —OH, —CN, —$CO_2H$, —$CO_2R_6$, —$CONR_8R_{8a}$, —$OCOR_6$, —$OCONR_8R_{8a}$, —$SO_2NR_8R_{8a}$, —SO-alkyl, —$SO_2$-alkyl, —$NR_9SO_2R_{9a}$, —$NR_9COR_{9a}$, —$OR_{9b}OR_{9b}Si(R_{9b})_3$, alkyl, alkoxy, alkenyl, haloalkoxy, alkylthio, alkylamino, amino or aminoalkyl;

$W_{2ee}$ is independently halogen, —OH, —CN, —$CO_2H$, —$CO_2R_6$, —$CONR_8R_{8a}$, —$OCOR_6$, —$OCONR_8R_{8a}$, —$SO_2NR_8R_{8a}$, —SO-alkyl, —$SO_2$-alkyl, —$NR_9SO_2R_{9a}$, —$NR_9CO_2R_{9a}$, alkyl, alkenyl, haloalkoxy, alkylthio or aminoalkyl;

provided that $W_{2aa}$ or $W_{2ee}$ are not only halogen;

$R_3$, $R_{3a}$ and $R_{3b}$ are independently hydrogen, halogen, —OH, —CN, —$NO_2$, —$CO_2R_{8a}$, —$CONR_8R_{8a}$, —$SO_2NR_8R_{8a}$, —$SOR_{8a}$, —$SO_2R_{8a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is alkyl or cycloalkyl, both of which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_8R_{8a}$, —$CONR_8R_{8a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4aa}$ is cycloalkyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_8R_{8a}$, —$CONR_8R_{8a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4ee}$ is alkyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_8R_{8a}$, —$CONR_8R_{8a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aiyl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, cyanoalkyl, alkoxy, haloalkoxy, aryl, aryloxy, arylaryl, arylalkyl, arylalkyloxy, alkenyl, cycloalkyl, cycloalkylalkyl, cycloalkylalkyloxy, amino, —OH, —$CO_2R_8$, —$CONR_8R_{8a}$, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$SO_2R_{9b}$—$NO_2$, —CN or thiol, wherein the aryl or heteroaryl may be optionally substituted with $R_{10}$, $R_{10a}$, $R_{10b}$, and $R_{10c}$;

$R_8$ and $R_{8a}$, at each occurrence, is independently hydrogen, alkyl, cycloalkyl, aryl, heteroaryl or heterocyclyl, all of which may be optionally substituted with $R_{10}$, $R_{10a}$, $R_{10b}$, and $R_{10c}$;

or alternatively $R_8$ and $R_{8a}$ can be taken together with the nitrogen to which they are attached to form a heterocyclyl ring containing 1, 2, 3, or 4 heteroatoms independently selected from the group consisting of N, NH, O and S, which may be optionally substituted with $R_{10}$, $R_{10a}$, $R_{10b}$, and $R_{10c}$;

$R_9$ and $R_{9a}$, at each occurrence, is independently hydrogen, alkyl, cycloalkyl, aryl, arylalkyl, heteroaryl or heterocyclyl, all of which may be optionally substituted with $R_{10}$, $R_{10a}$, $R_{10b}$, and $R_{10c}$;

$R_{9b}$, at each occurrence, is independently alkyl, cycloalkyl, aryl or heteroaryl, all of which may be optionally substituted with $R_{10}$, $R_{10a}$, $R_{10b}$, and $R_{10c}$; and $R_{10}$, $R_{10a}$, $R_{10b}$, and $R_{10c}$, at each occurrence, are independently halo, alkyl, haloalkyl, cyanoalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol.

In another embodiment, compounds are those in which:

L is -alkenyl-$(W_1)_n$ or -alkyl-$(W_2)_n$;

$L_{aa}$ is -alkenyl-$(W_1)_n$ or -alkyl-$(W_{2aa})_n$;

$L_{ee}$ is -cycloalkyl-$(W_1)_n$ or -alkyl-$(W_{2ee})_n$;

n is 1 to 3;

$W_1$, at each occurrence, is independently halogen, —OH, —CN, —$CO_2R_6$, —$CONR_8R_{8a}$, —$OCONR_8R_{8a}$, —$SO_2NR_8R_{8a}$, —$SOR_6$, —$SO_2R_6$, —$NR_9SO_2R_{9a}$, alkyl, haloalkyl, alkoxy, aryloxy, haloalkoxy, alkylthio, arylthio, arylsulfonyl, aminoalkyl, arylamino or heteroarylamino;

$W_2$ is independently halogen, —OH, —$CO_2H$, —CN, —$CO_2R_6$, —$CONR_8R_{8a}$, —$OCOR_6$, —$OCONR_8R_{8a}$, —$SO_2NR_8R_{8a}$, —SO-alkyl, —$SO_2$-alkyl, —$NR_9SO_2R_{9a}$, —$NR_9COR_{9a}$, alkyl, haloalkyl, alkoxy, alkenyl, haloalkoxy, alkylthio, alkylamino or aminoalkyl;

$W_{2aa}$ is independently halogen, —OH, —CN, —$CO_2H$, —$CO_2R_6$, —$CONR_8R_{8a}$, —$OCOR_6$, —$OCONR_8R_{8a}$, —$SO_2NR_8R_{8a}$, —SO-alkyl, —$SO_2$-alkyl, —$NR_9SO_2R_{9a}$, —$NR_9COR_{9a}$, —$OR_{9b}OR_{9b}Si(R_{9b})_3$, alkyl, alkoxy, alkenyl, haloalkoxy, alkylthio, alkylamino or aminoalkyl;

$W_{2ee}$ is independently halogen, —OH, —CN, —$CO_2H$, —$CO_2R_6$, —$CONR_8R_{8a}$, —$OCOR_6$, —$OCONR_8R_{8a}$, —$SO_2NR_8R_{8a}$, —SO-alkyl, —$SO_2$-alkyl, —$NR_9SO_2R_{9a}$, alkyl, alkenyl, haloalkoxy, alkylthio or aminoalkyl;

provided that $W_{2aa}$ or $W_{2ee}$ are not only halogen;

$R_3$, $R_{3a}$ and $R_{3b}$ are independently hydrogen, halogen, —OH, —CN, —$NO_2$, —$CO_2R_{8a}$, —$CONR_8R_{8a}$, —$SO_2NR_8R_{8a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is alkyl or cycloalkyl, both of which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_8R_{8a}$, —$CONR_8R_{8a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4aa}$ is cycloalkyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_8R_{8a}$, —$CONR_8R_{8a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4ee}$ is alkyl, which may be optionally substituted with one or more substituents selected from halogen, —OH, —$OR_6$, —$SR_6$, —$OCOR_6$, —CN, —$COR_6$, —$CO_2R_6$, —$CO_2H$, —OCONR$_8$R$_{8a}$, —CONR$_8$R$_{8a}$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_6$, at each occurrence, is independently alkyl, cycloalkyl, aryl or heteroaryl, all of which may be optionally substituted with R$_7$, R$_{7a}$, R$_{7b}$, and R$_{7c}$;

R$_7$, R$_{7a}$, R$_{7b}$, and R$_{7c}$, at each occurrence, are independently halo, alkyl, haloalkyl, alkoxy, haloalkoxy, aryl, aryloxy, arylaryl, arylalkyl, arylalkyloxy, alkenyl, cycloalkyl, cycloalkylalkyl, cycloalkylalkyloxy, amino, —OH, —CO$_2$R$_8$, —CONR$_8$R$_{8a}$, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —SO$_2$R$_{9b}$ —NO$_2$, —CN or thiol, wherein the aryl or heteroaryl may be optionally substituted with R$_{10}$, R$_{10a}$, R$_{10b}$, and R$_{10c}$;

R$_8$ and R$_{8a}$, at each occurrence, is independently hydrogen, alkyl, cycloalkyl, aryl, heteroaryl or heterocyclyl, all of which may be optionally substituted with R$_{10}$, R$_{10a}$, R$_{10b}$, and R$_{10c}$;

R$_9$ and R$_{9a}$, at each occurrence, is independently hydrogen, alkyl, cycloalkyl, aryl, arylalkyl, heteroaryl or heterocyclyl, all of which may be optionally substituted with R$_{10}$, R$_{10a}$, R$_{10b}$, and R$_{10c}$;

R$_{9b}$, at each occurrence, is independently alkyl, cycloalkyl, aryl or heteroaryl, all of which may be optionally substituted with R$_{10}$, R$_{10a}$, R$_{10b}$, and R$_{10c}$; and R$_{10}$, R$_{10a}$, R$_{10b}$, and R$_{10c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

In yet another embodiment, compounds are those in which:

L is -alkyl-(W$_2$)$_n$;

L$_{aa}$ is -alkenyl-(W$_1$)$_n$ or -alkyl-(W$_{2aa}$)$_n$;

L$_{ee}$ is -cycloalkyl-(W$_1$)$_n$ or -alkyl-(W$_{2ee}$)$_n$;

n is 1 to 2;

W$_1$, at each occurrence, is independently halogen, —OH, —CN, —CO$_2$R$_6$, —CONR$_8$R$_{8a}$, —OCONR$_8$R$_{8a}$, —SO$_2$NR$_8$R$_{8a}$, —SOR$_6$, —SO$_2$R$_6$, alkyl, haloalkyl, alkoxy, aryloxy, haloalkoxy, alkylthio, arylthio, arylsulfonyl, aminoalkyl, arylamino or heteroarylamino;

W$_2$ is independently halogen, —OH, —CO$_2$H, —CN, —CO$_2$R$_6$, —CONR$_8$R$_{8a}$, —OCOR$_6$, —SO$_2$NR$_9$R$_{9a}$, —SO-alkyl, —SO$_2$-alkyl, —NR$_9$SO$_2$R$_{9a}$, —NR$_9$COR$_{9a}$, alkyl, haloalkyl, alkoxy, alkenyl, haloalkoxy, alkylthio, alkylamino or aminoalkyl;

W$_{2aa}$ is independently halogen, —OH, —CN, —CO$_2$H, —CO$_2$R$_6$, —CONR$_8$R$_{8a}$, —OCOR$_6$, —OCONR$_8$R$_{8a}$, —SO$_2$NR$_8$R$_{8a}$, —SO-alkyl, —SO$_2$-alkyl, —NR$_9$SO$_2$R$_{9a}$, alkyl, alkoxy, alkenyl, haloalkoxy, alkylthio, alkylamino or aminoalkyl;

W$_{2ee}$ is independently halogen, —OH, —CN, —CO$_2$H, —CO$_2$R$_6$, —CONR$_8$R$_{8a}$, —OCOR$_6$, —OCONR$_9$R$_{9a}$, —SO$_2$NR$_8$R$_{8a}$, —SO-alkyl, —SO$_2$-alkyl, —NR$_9$SO$_2$R$_{9a}$, alkyl, alkenyl, haloalkoxy, alkylthio or aminoalkyl;

provided that W$_{2aa}$ or W$_{2ee}$ are not only halogen;

R$_3$, R$_{3a}$ and R$_{3b}$ are independently hydrogen, halogen, —OH, —CN, —NO$_2$, —CO$_2$R$_{8a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with R$_7$, R$_{7a}$, R$_{7b}$, and R$_{7c}$;

R$_4$ is alkyl or cycloalkyl, both of which may be optionally substituted with one or more substituents selected from halogen, —OH, —OR$_6$, —SR$_6$, —CN, —COR$_6$, —CO$_2$R$_6$, —CO$_2$H, —CONR$_8$R$_{8a}$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_{4aa}$ is cycloalkyl, which may be optionally substituted with one or more substituents selected from halogen, —OH, —OR$_6$, —SR$_6$, —CN, —COR$_6$, —CO$_2$R$_6$, —CO$_2$H, —CONR$_8$R$_{8a}$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_{4ee}$ is alkyl, which may be optionally substituted with one or more substituents selected from halogen, —OH, —OR$_6$, —SR$_6$, —CN, —COR$_6$, —CO$_2$R$_6$, —CO$_2$H, —CONR$_8$R$_{8a}$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_6$, at each occurrence, is independently alkyl, cycloalkyl, aryl or heteroaryl, all of which may be optionally substituted with R$_7$, R$_{7a}$, R$_{7b}$, and R$_{7c}$;

R$_7$, R$_{7a}$, R$_{7b}$, and R$_{7c}$, at each occurrence, are independently halo, alkyl, haloalkyl, alkoxy, haloalkoxy, aryl, aryloxy, arylaryl, arylalkyl, arylalkyloxy, alkenyl, cycloalkyl, cycloalkylalkyl, cycloalkylalkyloxy, amino, —OH, —CO$_2$R$_8$, —CONR$_8$R$_{8a}$, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —SO$_2$R$_{9b}$ —NO$_2$, —CN or thiol, wherein the aryl or heteroaryl may be optionally substituted with R$_{10}$, R$_{10a}$, R$_{10b}$, and R$_{10c}$;

R$_8$ and R$_{8a}$, at each occurrence, is independently hydrogen, alkyl, cycloalkyl, aryl or heteroaryl, all of which may be optionally substituted with R$_{10}$, R$_{10a}$, R$_{10b}$, and R$_{10c}$;

R$_9$ and R$_{9a}$, at each occurrence, is independently hydrogen, alkyl, cycloalkyl, aryl, arylalkyl or heteroaryl, all of which may be optionally substituted with R$_{10}$, R$_{10a}$, R$_{10b}$, and R$_{10c}$;

R$_{9b}$, at each occurrence, is independently alkyl, cycloalkyl, aryl or heteroaryl, all of which may be optionally substituted with R$_{10}$, R$_{10a}$, R$_{10b}$, and R$_{10c}$; and R$_{10}$, R$_{10a}$, R$_{10b}$, and R$_{10c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

In another embodiment, compounds are those in which:

L is -alkyl-(W$_2$)$_n$;

L$_{aa}$ is -alkenyl-(W$_1$)$_n$ or -alkyl-(W$_{2aa}$)$_n$;

L$_{ee}$ is -cycloalkyl-(W$_1$)$_n$ or -alkyl-(W$_{2ee}$)$_n$;

n is 1 to 2;

W$_1$, at each occurrence, is independently halogen, —OH, —CN, —CO$_2$R$_6$, —CONR$_8$R$_{8a}$, —OCONR$_8$R$_{8a}$, —SO$_2$NR$_8$R$_{8a}$, —SOR$_6$, —SO$_2$R$_6$, alkyl, haloalkyl, alkoxy, aryloxy, haloalkoxy, alkylthio, arylthio, arylsulfonyl, arylamino or heteroarylamino;

W$_2$ is independently halogen, —OH, —CO$_2$H, —CN, —CO$_2$R$_6$, —CONR$_8$R$_{8a}$, —OCOR$_6$, —OCONR$_8$R$_{8a}$, —SO$_2$NR$_8$R$_{8a}$, —SO-alkyl, —SO$_2$-alkyl, —NR$_9$SO$_2$R$_{9a}$, alkyl, haloalkyl, alkoxy, alkenyl, haloalkoxy, alkylthio, alkylamino or aminoalkyl;

$W_{2aa}$ is independently halogen, —OH, —CN, —CO$_2$H, —CO$_2$R$_6$, —CONR$_8$R$_{8a}$, —OCOR$_6$, —OCONR$_8$R$_{8a}$, —SO$_2$NR$_8$R$_{8a}$, —SO-alkyl, —SO$_2$-alkyl, —NR$_9$SO$_2$R$_{9a}$, alkyl, alkoxy, alkenyl, haloalkoxy or alkylthio;

$W_{2ee}$ is independently halogen, —OH, —CN, —CO$_2$H, —CO$_2$R$_6$, —CONR$_8$R$_{8a}$, —OCOR$_6$, —OCONR$_8$R$_{8a}$, —SO$_2$NR$_8$R$_{8a}$, —SO-alkyl, —SO$_2$-alkyl, —NR$_9$SO$_2$R$_{9a}$, alkyl, alkenyl, haloalkoxy or alkylthio;

provided that $W_{2aa}$ or $W_{2ee}$ are not only halogen;

$R_3$, $R_{3a}$ and $R_{3b}$ are independently hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —OR$_6$, —SR$_6$, —CN, —COR$_6$, —CO$_2$R$_6$, —CO$_2$H, —CONR$_8$R$_{8a}$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4aa}$ is cycloalkyl, which may be optionally substituted with one or more substituents selected from halogen, —OH, —OR$_6$, —SR$_6$, —CN, —COR$_6$, —CO$_2$R$_6$, —CO$_2$H, —CONR$_8$R$_{8a}$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4ee}$ is alkyl, which may be optionally substituted with one or more substituents selected from halogen, —OH, —OR$_6$, —SR$_6$, —CN, —COR$_6$, —CO$_2$R$_6$, —CO$_2$H, —CONR$_8$R$_{8a}$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, haloalkoxy, aryl, aryloxy, arylaryl, arylalkyl, arylalkyloxy, alkenyl, cycloalkyl, cycloalkylalkyl, cycloalkylalkyloxy, amino, —OH, —CO$_2$R$_8$, —CONR$_8$R$_{8a}$, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —SO$_2$R$_{9b}$—NO$_2$, —CN or thiol, wherein the aryl or heteroaryl may be optionally substituted with $R_{10}$, $R_{10a}$, $R_{10b}$, and $R_{10c}$;

$R_8$ and $R_{8a}$, at each occurrence, is independently hydrogen, alkyl, aryl or heteroaryl, all of which may be optionally substituted with $R_{10}$, $R_{10a}$, $R_{10b}$, and $R_{10c}$;

$R_9$ and $R_{9a}$, at each occurrence, is independently hydrogen, alkyl, cycloalkyl, aryl or heteroaryl, all of which may be optionally substituted with $R_{10}$, $R_{10a}$, $R_{10b}$, and $R_{10c}$;

$R_{9b}$, at each occurrence, is independently alkyl, cycloalkyl, aryl or heteroaryl, all of which may be optionally substituted with $R_{10}$, $R_{10a}$, $R_{10b}$, and $R_{10c}$; and $R_{10}$, $R_{10a}$, $R_{10b}$, and $R_{10c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

In still yet another embodiment, compounds are those in which:

L is -alkyl-(W$_2$)$_n$;
$L_{aa}$ is -alkyl-(W$_{2aa}$)$_n$;
$L_{ee}$ is -alkyl-(W$_{2ee}$)$_n$;
n is 1 to 2;

$W_2$ is independently halogen, —OH, —CO$_2$H, —CN, —CO$_2$R$_6$, —CONR$_8$R$_{8a}$, —OCOR$_6$, —OCONR$_9$R$_{9a}$, —SO$_2$NR$_8$R$_{8a}$, —SO-alkyl, —SO$_2$-alkyl, —NR$_9$SO$_2$R$_{9a}$, alkyl, haloalkyl, alkoxy or haloalkoxy;

$W_{2aa}$ is independently halogen, —OH, —CN, —CO$_2$H, —CO$_2$R$_6$, —CONR$_8$R$_{8a}$, —OCONR$_8$R$_{8a}$, —SO$_2$NR$_8$R$_{8a}$, —SO-alkyl, —SO$_2$-alkyl, —NR$_9$SO$_2$R$_{9a}$, alkyl, alkoxy, alkenyl or haloalkoxy;

$W_{2ee}$ is independently halogen, —OH, —CN, —CO$_2$H, —CO$_2$R$_6$, —CONR$_8$R$_{8a}$, —OCONR$_8$R$_{8a}$, —SO$_2$NR$_8$R$_{8a}$, —SO-alkyl, —SO$_2$-alkyl, —NR$_9$SO$_2$R$_{9a}$, alkyl, alkoxy, alkenyl or haloalkoxy;

provided that $W_{2aa}$ or $W_{2ee}$ are not only halogen;

$R_3$, $R_{3a}$ and $R_{3b}$ are independently hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is a 3- to 10-membered cycloalkyl, which may be optionally substituted with one or more substituents selected from halogen, —OH, —OR$_6$, —SR$_6$, —CN, —COR$_6$, —CO$_2$R$_6$, —CO$_2$H, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4aa}$ is cycloalkyl, which may be optionally substituted with one or more substituents selected from halogen, —OH, —OR$_6$, —SR$_6$, —CN, —COR$_6$, —CO$_2$R$_6$, —CO$_2$H, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4ee}$ is alkyl, which may be optionally substituted with one or more substituents selected from halogen, —OH, —OR$_6$, —SR$_6$, —CN, —COR$_6$, —CO$_2$R$_6$, —CO$_2$H, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl;

$R_7$, $R_{7a}$, $R_{7b}$, and $R_{7c}$, at each occurrence, are independently halo, alkyl, haloalkyl, alkoxy, haloalkoxy, aryl, aryloxy, arylaryl, arylalkyl, arylalkyloxy, alkenyl, cycloalkyl, cycloalkylalkyl, cycloalkylalkyloxy, amino, —OH, —CO$_2$R$_8$, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —SO$_2$R$_{9b}$—NO$_2$, —CN or thiol, wherein the aryl or heteroaryl may be optionally substituted with $R_{10}$, $R_{10a}$, $R_{10b}$, and $R_{10c}$;

$R_8$ and $R_{8a}$, at each occurrence, is independently hydrogen, alkyl or aryl, all of which may be optionally substituted with $R_{10}$, $R_{10a}$, $R_{10b}$, and $R_{10c}$;

$R_9$ and $R_{9a}$, at each occurrence, is independently hydrogen, alkyl, cycloalkyl, aryl or heteroaryl, all of which may be optionally substituted with $R_{10}$, $R_{10a}$, $R_{10b}$, and $R_{10c}$;

$R_{9b}$, at each occurrence, is independently alkyl, cycloalkyl, aryl or heteroaryl; and $R_{10}$, $R_{10a}$, $R_{10b}$, and $R_{10c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

In one embodiment, compounds are those in which:

L is -alkyl-(W$_2$)$_n$;

L$_{aa}$ is -alkyl-(W$_{2aa}$)$_n$;

L$_{ee}$ is -alkyl-(W$_{2ee}$)$_n$;

n is 1 to 2;

W$_2$ is independently halogen, —OH, —CO$_2$H, —CN, —CO$_2$R$_6$, —CONR$_8$R$_{8a}$, —OCOR$_6$, —OCONR$_8$R$_{8a}$, —SO$_2$NR$_8$R$_{8a}$, —SO-alkyl, —SO$_2$-alkyl, alkyl or haloalkyl;

W$_{2aa}$ is independently halogen, —OH, —CN, —CO$_2$H, —CO$_2$R$_6$, —CONR$_8$R$_{8a}$, —OCONR$_8$R$_{8a}$, —SO$_2$NR$_8$R$_{8a}$, —SO-alkyl, —SO$_2$-alkyl, —NR$_9$SO$_2$R$_{9a}$, alkyl, alkoxy or haloalkoxy;

W$_{2ee}$ is independently halogen, —OH, —CN, —CO$_2$H, —CO$_2$R$_6$, —CONR$_8$R$_{8a}$, —OCONR$_8$R$_{8a}$, —SO$_2$NR$_8$R$_{8a}$, —SO-alkyl, —SO$_2$-alkyl, —NR$_9$SO$_2$R$_{9a}$, alkyl, alkoxy or haloalkoxy;

provided that W$_{2aa}$ or W$_{2ee}$ are not only halogen;

R$_3$, R$_{3a}$ and R$_{3b}$ are independently hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl;

R$_4$ is a 3- to 7-membered cycloalkyl, which may be optionally substituted with one or more substituents selected from halogen, —OH, —OR$_6$, —SR$_6$, —CN, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_{4aa}$ is cycloalkyl, which may be optionally substituted with one or more substituents selected from halogen, —OH, —OR$_6$, —SR$_6$, —CN, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_{4ee}$ is alkyl, which may be optionally substituted with one or more substituents selected from halogen, —OH, —OR$_6$, —SR$_6$, —CN, —COR$_6$, —CO$_2$R$_6$, —CO$_2$H, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_6$, at each occurrence, is independently alkyl, cycloalkyl, aryl or heteroaryl;

R$_7$, R$_{7a}$, R$_{7b}$, and R$_{7c}$, at each occurrence, are independently halo, alkyl, haloalkyl, alkoxy, haloalkoxy, aryl, aryloxy, arylaryl, arylalkyl, cycloalkyl, amino, —OH, —CO$_2$R$_8$, hydroxyalkyl, heteroaryl, heteroaryloxy, heteroarylalkyl, alkylthio, arylalkylthio, —NO$_2$ or —CN, wherein the aryl or heteroaryl may be optionally substituted with R$_{10}$, R$_{10a}$, R$_{10b}$, and R$_{10c}$;

R$_8$ and R$_{8a}$, at each occurrence, is independently hydrogen or alkyl, wherein the alkyl may be optionally substituted with R$_{10}$, R$_{10a}$, R$_{10b}$, and R$_{10c}$; and R$_9$ and R$_{9a}$, at each occurrence, is independently hydrogen, alkyl, aryl or heteroaryl, all of which may be optionally substituted with R$_{10}$, R$_{10a}$, R$_{10b}$, and R$_{10c}$;

R$_{9b}$, at each occurrence, is independently alkyl, aryl or heteroaryl; and

R$_{10}$, R$_{10a}$, R$_{10b}$, and R$_{10c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

In still yet another embodiment, compounds are those in which:

L is -alkyl-(W$_2$)$_n$;

L$_{aa}$ is -alkyl-(W$_{2aa}$)$_n$;

L$_{ee}$ is -alkyl-(W$_{2ee}$)$_n$;

n is 1 to 2;

W$_2$ is independently halogen, —OH, —CN, —CO$_2$R$_6$, —SO-alkyl, —SO$_2$-alkyl, alkyl, or haloalkyl;

W$_{2aa}$ is independently —OH, —CN, —CO$_2$R$_6$, —SO-alkyl, —SO$_2$-alkyl, alkyl, alkoxy, or haloalkoxy;

W$_{2ee}$ is independently —OH, —CN, —CO$_2$R$_6$, —SO-alkyl, —SO$_2$-alkyl, alkyl or haloalkoxy;

R$_3$, R$_{3a}$ and R$_{3b}$ are independently hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl;

R$_4$ is a 3- or 4-membered cycloalkyl, which may be optionally substituted with one or more substituents selected from halogen, —OH, —OR$_6$, —SR$_6$, —CN, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_{4aa}$ is cycloalkyl, which may be optionally substituted with one or more substituents selected from halogen, —OH, —OR$_6$, —SR$_6$, —CN, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_{4ee}$ is alkyl, which may be optionally substituted with one or more substituents selected from halogen, —OH, —OR$_6$, —SR$_6$, —CN, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$;

R$_6$, at each occurrence, is independently alkyl, cycloalkyl, aryl or heteroaryl; and R$_7$, R$_{7a}$, R$_{7b}$, and R$_{7c}$, at each occurrence, are independently halo, alkyl, haloalkyl, alkoxy, aryl, aryloxy, arylalkyl, cycloalkyl, amino, —OH, hydroxyalkyl, heteroaryl, heteroaryloxy, heteroarylalkyl, alkylthio, arylalkylthio, —NO$_2$, or —CN.

In still yet another embodiment, compounds are those in which:

R$_{4aa}$ is cyclopropyl or cyclobutyl, both of which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_8$R$_{8a}$, —CONR$_8$R$_{8a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$; and R$_{4ee}$ is isopropyl, which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_8$R$_{8a}$, —CONR$_8$R$_{8a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$.

In still yet another embodiment, compounds are those in which the compound is a compound of formula Iaa or Iee:

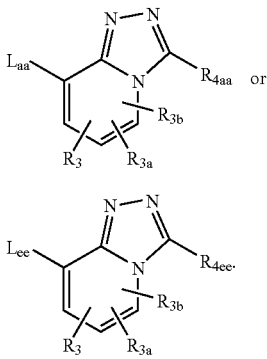

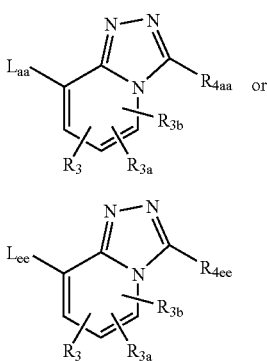

In another embodiment, compounds are those compounds in which the compound is a compound of formula Iaa or Iee:

Iaa

Iee wherein:

$L_{aa}$ is -alkyl-OH;

$L_{ee}$ is -alkyl-OH;

$R_3$, $R_{3a}$ and $R_{3b}$ are independently selected from hydrogen, halogen, —$CF_3$, $OCF_3$, alkyl or alkoxy.

In another embodiment, compounds are those compounds in which:

$R_3$, $R_{3a}$ and $R_{3b}$ are independently selected from hydrogen or halogen;

$R_{4aa}$ is cyclopropyl or cyclobutyl, both of which may be optionally substituted with one or more substituents selected from halogen, —OH, —$OR_6$, —CN, —$COR_6$, —$CO_2R_6$, —$CO_2H$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_{4ee}$ is isopropyl, which may be optionally substituted with one or more substituents selected from halogen, —OH, —$OR_6$, —CN, —$COR_6$, —$CO_2R_6$, —$CO_2H$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, or cycloalkyl; and $R_7$, $R_{7a}$, $R_{7b}$, and $R_{7c}$, at each occurrence, are independently halo, alkyl, haloalkyl, alkoxy, aryl, aryloxy, arylalkyl, cycloalkyl, amino, —OH, hydroxyalkyl, heteroaryl, heteroaryloxy, alkylthio, —$NO_2$, or —CN.

In another embodiment, compounds of the present invention are selected from the compounds exemplified in the examples, preferably examples 1, 11, 24 and 91, more preferably Example 1.

In another embodiment, a compound of the present invention is the hydrochloride or bisulfate salt of Example 1.

In yet another embodiment, a compound of the present invention is the hydrochloride salt of Example 1.

In still yet another embodiment, the compound of the present invention is a crystalline form of the hydrochloride salt of Example 1, preferably the N-1 or N-2 form, more preferably the N-1 form.

In one embodiment, the crystalline form is in substantially pure form.

In one embodiment, the crystalline form of the hydrochloride salt of Example 1 is characterized by unit cell parameters substantially equal to the following:

Cell Dimensions:

a=13.5209(3)

b=10.0154(2)

c=13.4607(3)

α=90

β=102.139(1)

γ=90

Space group: $P2_1/c$

Molecules/asymmetric unit (Z'): 1

Density, calc g-cm$^{-3}$: 1.358

In one embodiment, the crystalline form of the hydrochloride salt of Example 1 is characterized by characterized by a powder X-ray diffraction pattern comprising the following 2θ values (Cu Kα λ-1.5418 Å) 6.7±0.1, 11.1±0.1, 13.4±0.1, 13.7±0.1, 16.3±0.1, 19.1±0.1, 19.6±0.1, 22.3±0.1 and 24.6±0.1 at room temperature.

In one embodiment, the crystalline form of the hydrochloride salt of Example 1 is characterized by as characterized by a powder X-ray diffraction pattern substantially in accordance with that shown in FIG. 1.

Figure 2:
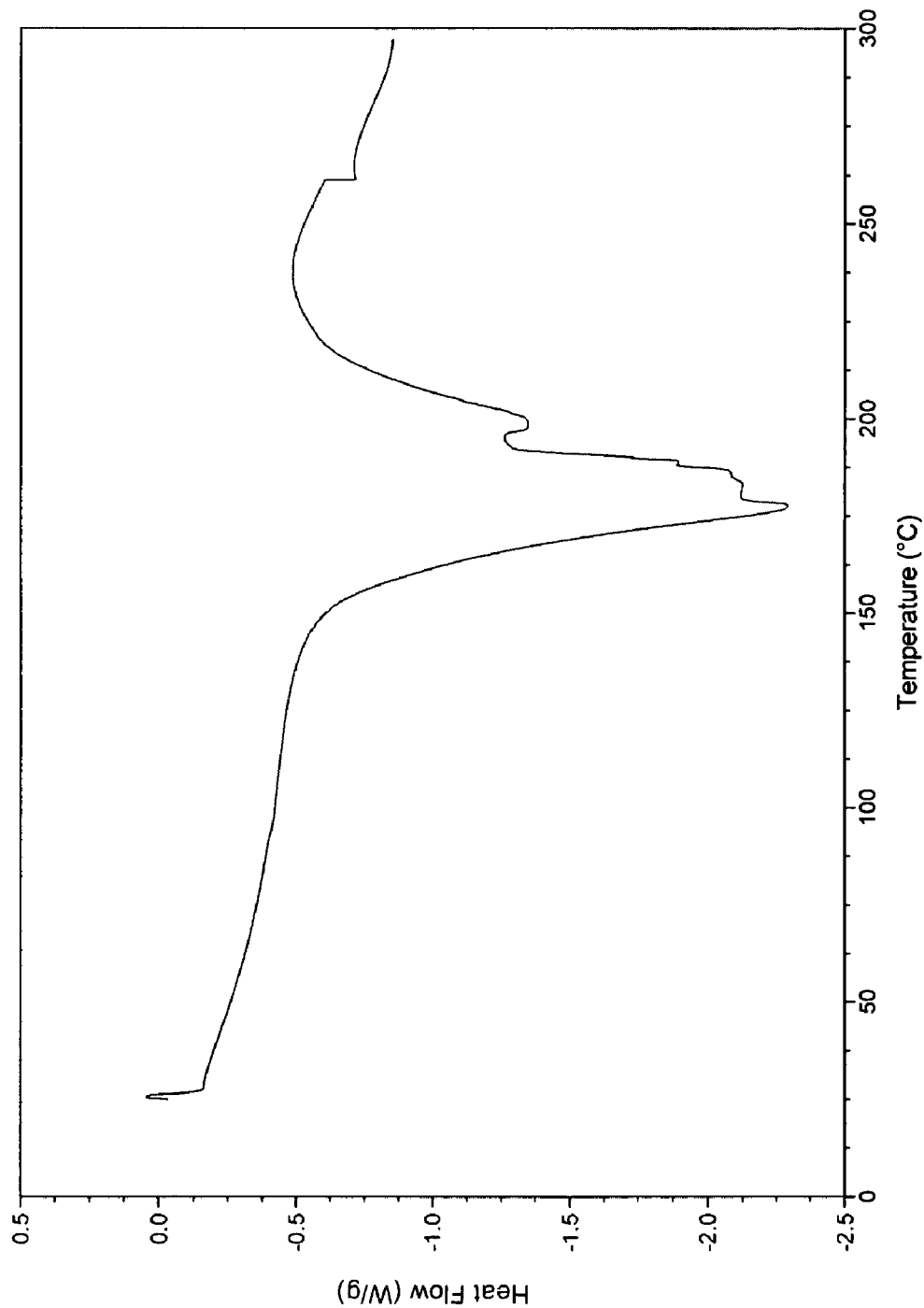
FIG. 2 shows a differential scanning calorimetry (DSC) thermogram of the N-1 crystalline form of a salt of a compound of Formula I.

In one embodiment, the crystalline form of the hydrochloride salt of Example 1 is characterized by is characterized by a differential scanning calorimetry thermogram substantially in accordance with that shown in FIG. 2, having an endothermic transition above ca. 150° C.

Figure 3:
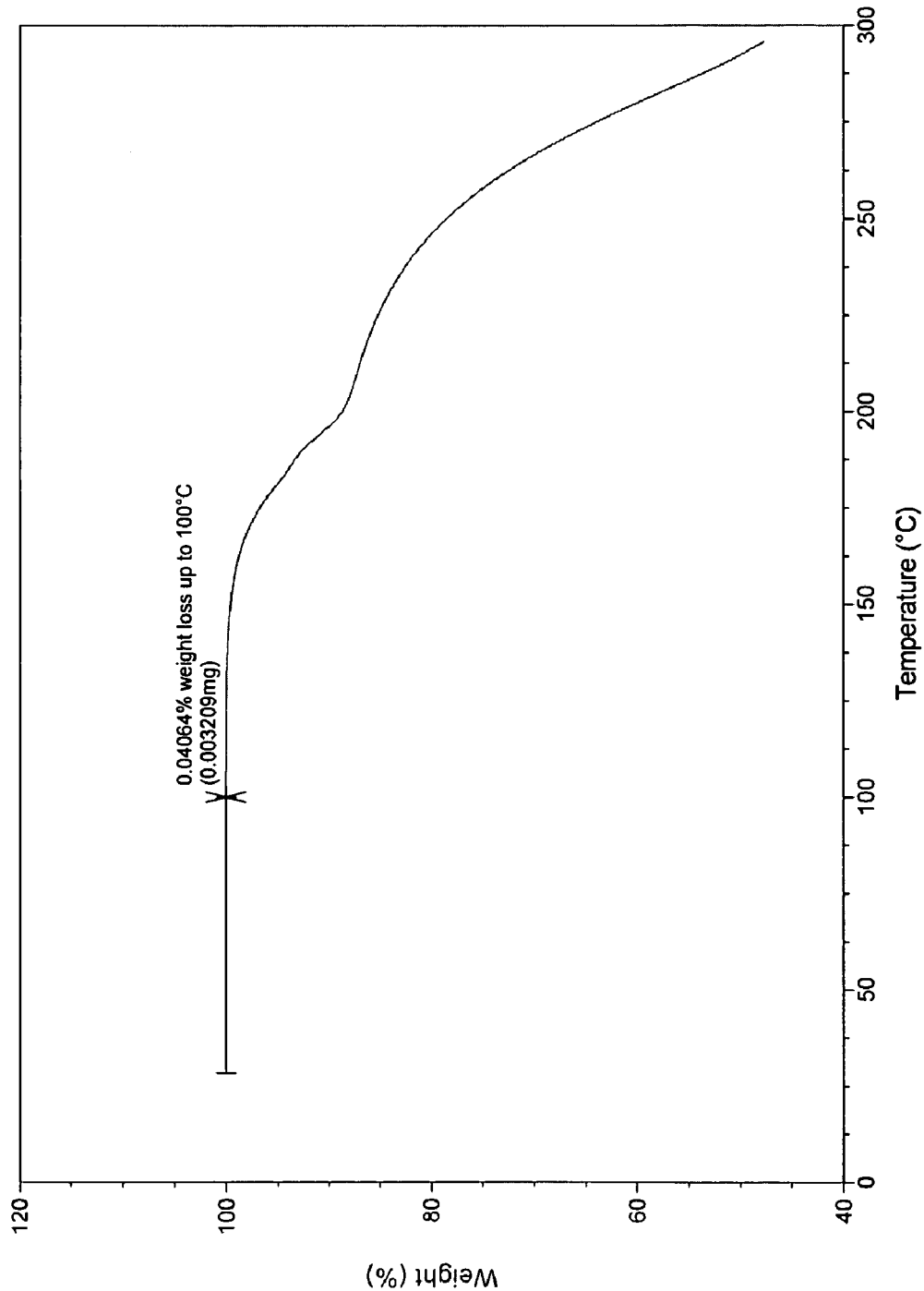
FIG. 3 shows a thermogravimetric analysis (TGA) curve of the N-1 crystalline form of a salt of a compound of Formula I.

In one embodiment, the crystalline form of the hydrochloride salt of Example 1 is characterized by a thermal gravimetric analysis curve in accordance with that shown in FIG. 3, having negligible weight loss up to about 100° C.

In another embodiment, the crystalline form of the hydrochloride salt of Example 1 is characterized by unit cell parameters substantially equal to the following:

Cell Dimensions:

a=12.908(4)

b=12.813(4)

c=10.959(2)

α=90

β=90

γ=90

Space group: $Pca2_1$

Molecules/asymmetric unit (Z'): 1

Density, calc g-cm$^{-3}$: 1.335

In another embodiment, the crystalline form of the hydrochloride salt of Example 1 is characterized by a powder X-ray diffraction pattern comprising the following 2θ values (Cu Kα λ-1.5418 Å) 6.9±0.1, 13.7±0.1, 15.4±0.1, 17.4±0.1, 21.2±0.1, 22.4±0.1 and 23.3±0.1 at room temperature.

Figure 5:
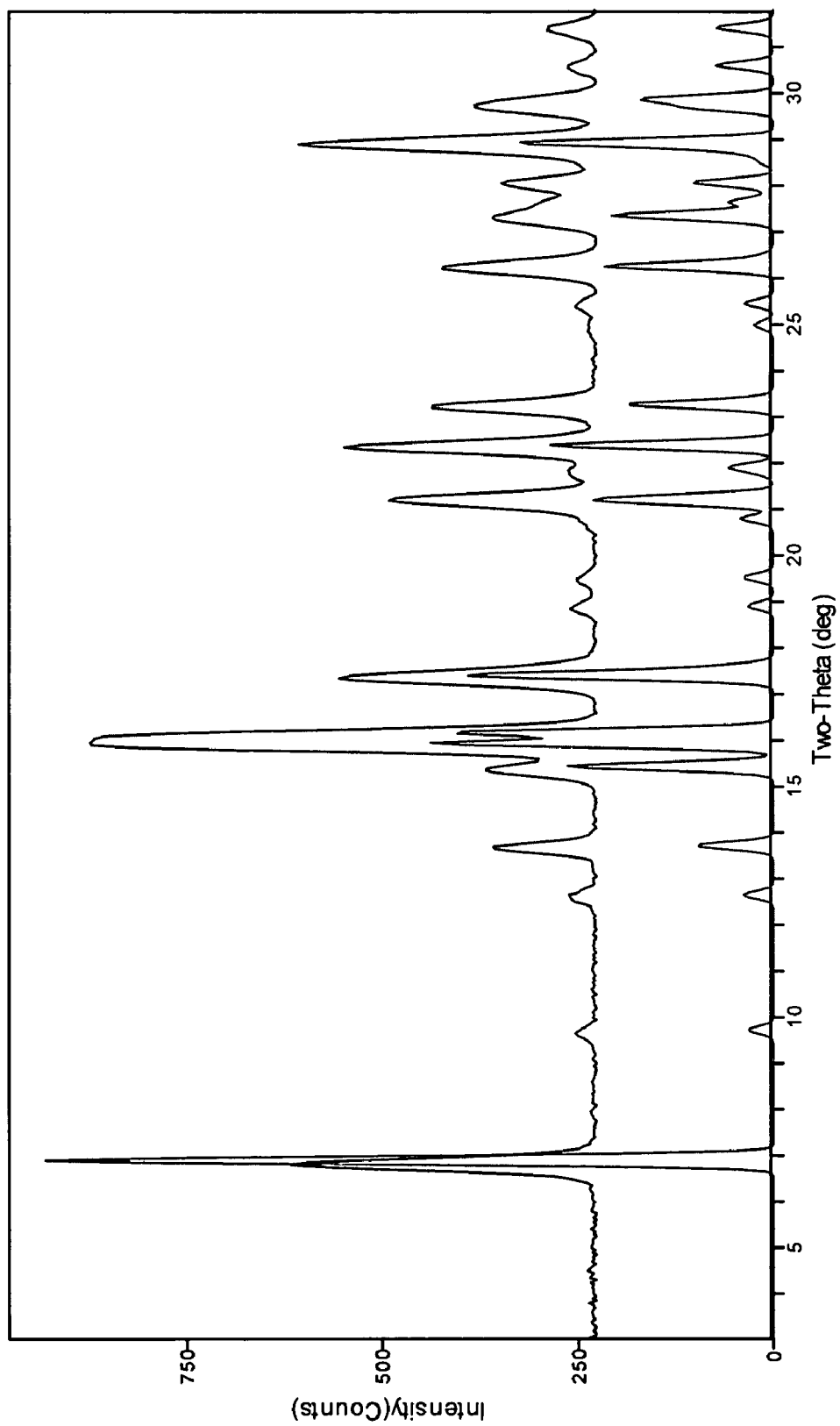
FIG. 5 shows observed (experimental at room temperature) and simulated (calculated at room temperature) powder x-ray diffraction patterns (Cu Kα$\lambda$=1.5418 Å) of an N-2 crystalline form of a salt of a compound of Formula I.

In another embodiment, the crystalline form of the hydrochloride salt of Example 1 is characterized by a powder X-ray diffraction pattern substantially in accordance with that shown in FIG. 5.

Figure 6:
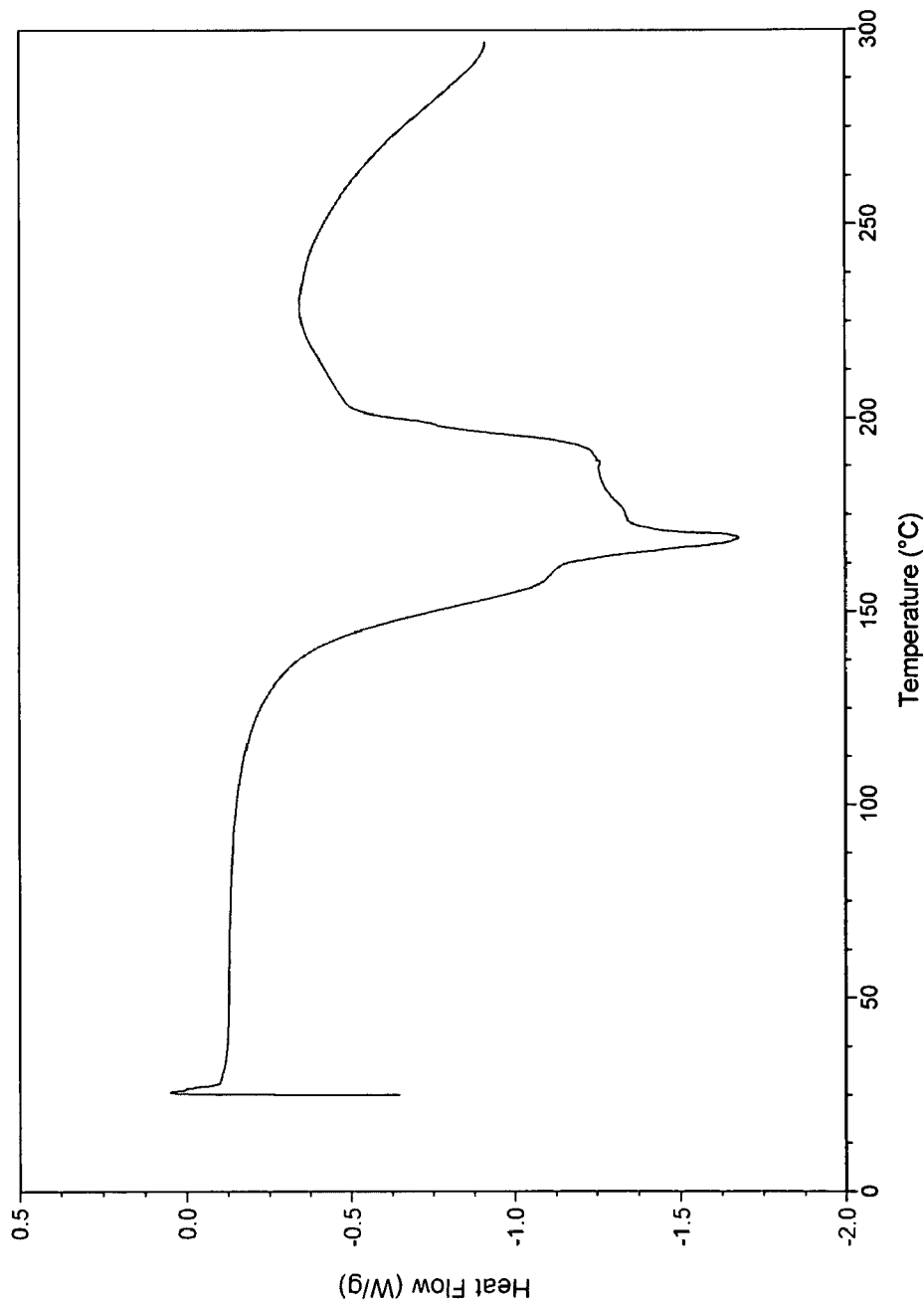
FIG. 6 shows a differential scanning calorimetry (DSC) thermogram of the N-2 crystalline form of a salt of a compound of Formula I.

In another embodiment, the crystalline form of the hydrochloride salt of Example 1 is characterized by a differential scanning calorimetry thermogram substantially in accordance with that shown in FIG. 6, having an endothermic transition above ca. 150° C.

Figure 7:
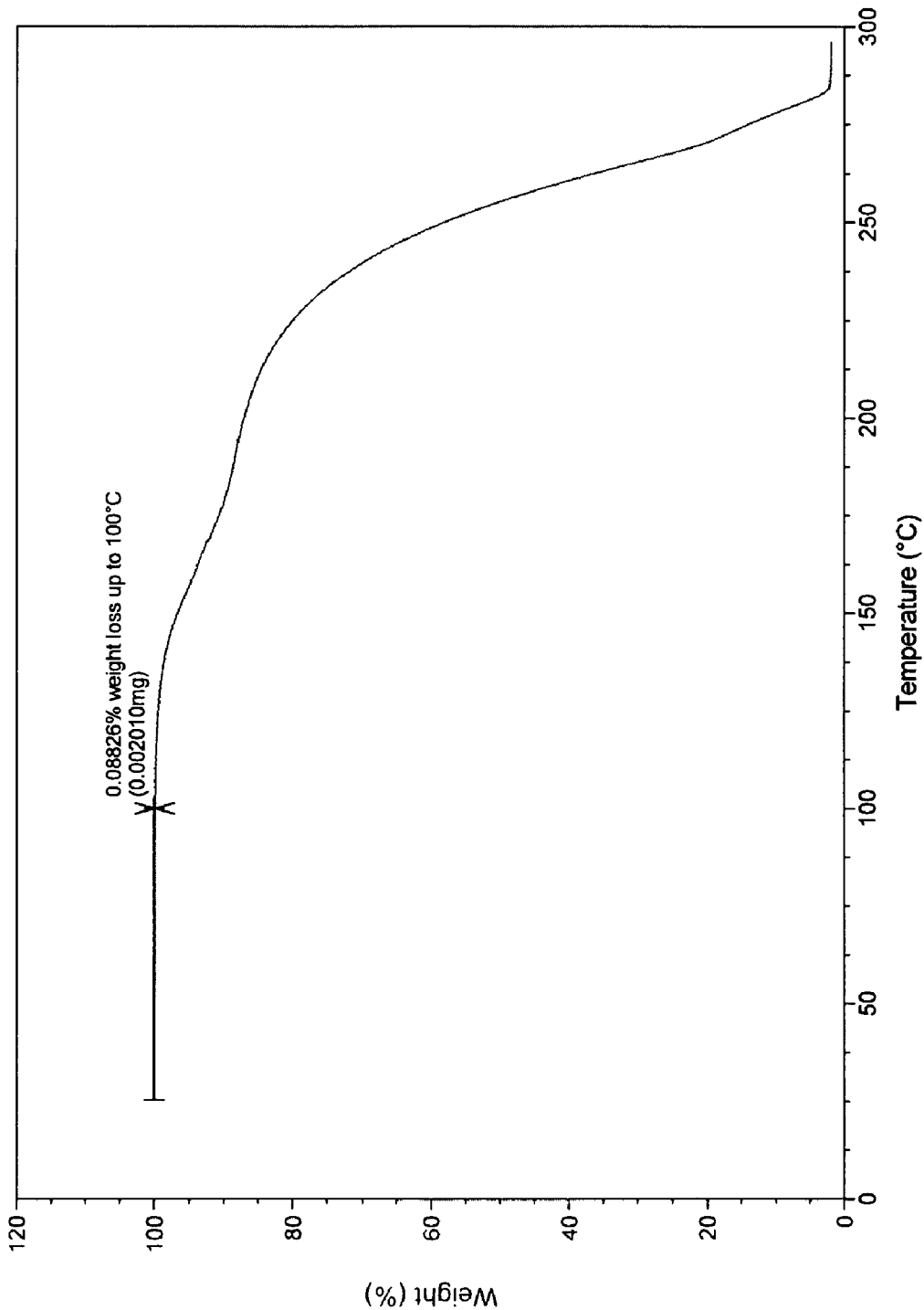
FIG. 7 shows a thermogravimetric analysis (TGA) curve of the N-2 crystalline form of a salt of a compound of Formula I.

In another embodiment, the crystalline form of the hydrochloride salt of Example 1 is characterized by a thermal gravimetric analysis curve in accordance with that shown in FIG. 7, having negligible weight loss up to about 100° C.

In another embodiment, the compound of the present invention is the bisulfate salt of Example 1.

In another embodiment, Example 1 is a crystalline form of the bisulfate salt, preferably, N-1 form, more preferably a substantially pure form.

In another embodiment, the crystalline form of the bisulfate salt of Example 1 is characterized by unit cell parameters substantially equal to the following:
Cell Dimensions:
- a=10.016(1)
- b=19.772(3)
- c=10.169(1)
- α=90
- β=103.454(7)
- γ=90
- Space group: $P2_1/c$
- Molecules/asymmetric unit (Z'): 1
- Density, calc g-cm$^{-3}$: 1.444

Figure 8:
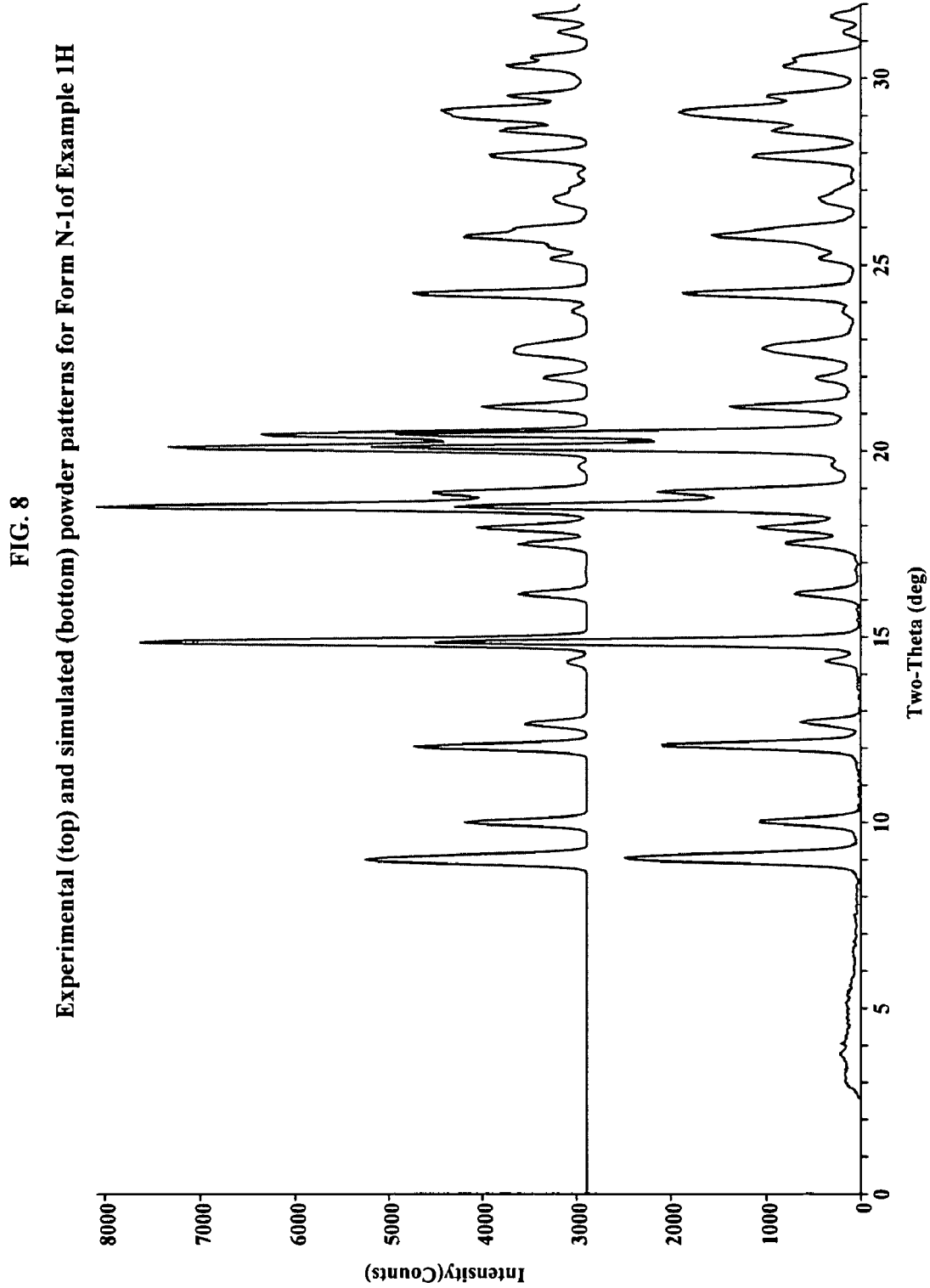
FIG. 8 shows observed (experimental at room temperature) and simulated (calculated at room temperature) powder x-ray diffraction patterns (Cu Kα$\lambda$=1.5418 Å) of another N-1 crystalline form of a salt of a compound of Formula I.

In one embodiment, the crystalline form of the bisulfate salt of Example 1 is characterized by a powder X-ray diffraction pattern substantially in accordance with that shown in FIG. 8.

In another embodiment, the present invention relates to pharmaceutical compositions comprised of a therapeutically effective amount of a compound of the present invention, preferably Examples 1, 1G, 1H, 11, 24 and 91, alone or, optionally, in combination with a pharmaceutically acceptable carrier and/or one or more other agent(s).

In another embodiment, the present invention relates to methods of inhibiting the activity of the enzyme 11-beta-hydroxysteroid dehydrogenase type I comprising administering to a mammalian patient, for example, a human patient, in need thereof a therapeutically effective amount of a compound of the present invention, preferably Examples 1, 1G, 1H, 11, 24 and 91, alone, or optionally, in combination with another compound of the present invention and/or at least one other type of therapeutic agent.

In another embodiment, the present invention relates to a method for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis, acute coronary syndrome, myocardial infarction, angina pectoris, peripheral vascular disease, intermittent claudication, abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma, rheumatoid arthritis, Cushing's Disease, Alzheimer's Disease and osteoarthritis.

In another embodiment, the present invention relates to a method for preventing, inhibiting, or treating the progression or onset of diabetes, hyperglycemia, obesity, dislipidemia, hypertension, cognitive impairment, rheumatoid arthritis, osteoarthritis, glaucoma, Cushing's Disease and Metabolic Syndrome comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In still another embodiment, the present invention relates to a method for preventing, inhibiting, or treating the progression or onset of diabetes, comprising administering to a mammalian patient, for example, a human patient, in need of prevention, inhibition, or treatment a therapeutically effective amount of a compound of the present invention, preferably Examples 1, 1G, 1H, 11, 24 and 91, alone, or optionally, in combination with another compound of the present invention and/or at least one other type of therapeutic agent.

In yet still another embodiment, the present invention relates to a method for preventing, inhibiting, or treating the progression or onset of hyperglycemia comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of obesity comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In one embodiment, the present invention relates to a method for preventing, inhibiting, or treating the progression or onset of dislipidemia comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of hypertension comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of cognitive impairment comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of rheumatoid arthritis comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of osteoarthritis comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of Metabolic Syndrome comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of glaucoma comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of Cushing's Disease comprising administering to a mammalian patient, for example, a human patient, in need of prevention, inhibition, or treatment a therapeutically effective amount of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to pharmaceutical compositions comprised of a therapeutically effective amount of a crystalline form of a compound of the present invention, preferably Examples 1, 1G, 1H, 11, 24 and 91, alone or, optionally, in combination with a pharmaceutically acceptable carrier and/or one or more other agent(s).

In another embodiment, the present invention relates to methods of inhibiting the activity of the enzyme 11-beta-hydroxysteroid dehydrogenase type I comprising administering to a mammalian patient, for example, a human patient, in need thereof a therapeutically effective amount of a crystalline form of a compound of the present invention, preferably Examples 1, 1G, 1H, 11, 24 and 91, alone, or optionally, in combination with another compound of the present invention and/or at least one other type of therapeutic agent.

In another embodiment, the present invention relates to a method for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis, acute coronary syndrome, myocardial infarction, angina pectoris, peripheral vascular disease, intermittent claudication, abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma, rheumatoid arthritis, Cushing's Disease, Alzheimer's Disease and osteoarthritis.

In another embodiment, the present invention relates to a method for preventing, inhibiting, or treating the progression or onset of diabetes, hyperglycemia, obesity, dislipidemia, hypertension, cognitive impairment, rheumatoid arthritis, osteoarthritis, glaucoma, Cushing's Disease and Metabolic Syndrome comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In still another embodiment, the present invention relates to a method for preventing, inhibiting, or treating the progression or onset of diabetes, comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In yet still another embodiment, the present invention relates to a method for preventing, inhibiting, or treating the progression or onset of hyperglycemia comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of obesity comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In one embodiment, the present invention relates to a method for preventing, inhibiting, or treating the progression or onset of dislipidemia comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of hypertension comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of cognitive impairment comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of rheumatoid arthritis comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of osteoarthritis comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of Metabolic Syndrome comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of glaucoma comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In another embodiment, the present invention relates to a method for preventing, inhibiting, or treating the progression or onset of Cushing's Disease comprising administering to a mammalian patient, for example, a human patient, in need of prevention, inhibition, or treatment a therapeutically effective amount of a crystalline form of a compound of the present invention, preferably Examples 1, 1G, 1H, 11, 24 and 91, alone, or, optionally, in combination with another compound of the present invention and/or at least one other type of therapeutic agent.

In another embodiment, the present invention provides a compound of the present invention, preferably Examples 1, 1G, 1H, 11, 24 and 91, for use in therapy for treating a metabolic disease.

In another embodiment, the present invention provides a combined preparation of a compound of the present invention, preferably Examples 1, 1G, 1H, 11, 24 and 91, and additional therapeutic agent(s) for simultaneous, separate or sequential use in therapy.

In another embodiment, the present invention provides a combined preparation of a compound of the present invention, preferably Examples 1, 1G, 1H, 11, 24 and 91, and additional therapeutic agent(s) for simultaneous, separate or sequential use in treatment of a metabolic disease.

In another embodiment, the present invention provides a novel article of manufacture, comprising: (a) a first container; (b) a pharmaceutical composition located within the first container, wherein the composition, comprises: a first therapeutic agent, comprising: a compound of the present invention, preferably Examples 1, 1G, 1H, 11, 24 and 91; and (c) a package insert stating that the pharmaceutical composition can be used for the treatment of a metabolic disease.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention, preferably Examples 1, 1G, 1H, 11, 24 and 91; and (c) a package insert stating that the pharmaceutical composition can be used in combination with a second therapeutic agent to treat a metabolic disease.

In another embodiment, the present invention provides crystalline forms of compounds of the present invention, preferably Examples 1, 1G, 1H, 11, 24 and 91, for use in therapy for treating a metabolic disease.

In another embodiment, the present invention provides combined preparations of crystalline forms of compounds of the present invention, preferably Examples 1, 1G, 1H, 11, 24 and 91, and additional therapeutic agent(s) for simultaneous, separate or sequential use in therapy.

In another embodiment, the present invention provides combined preparations of crystalline forms of compounds of the present invention, preferably Examples 1, 1G, 1H, 11, 24 and 91, and additional therapeutic agent(s) for simultaneous, separate or sequential use in treatment of a metabolic disease.

In another embodiment, the present invention provides a novel article of manufacture, comprising: (a) a first container; (b) a pharmaceutical composition located within the first container, wherein the composition, comprises: a first therapeutic agent, comprising: a crystalline form of a compound of the present invention, preferably Examples 1, 1G, 1H, 11, 24 and 91; and (c) a package insert stating that the pharmaceutical composition can be used for the treatment of a metabolic disease.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a crystalline form of a compound of the present invention; and (c) a package insert stating that the pharmaceutical composition can be used in combination with a second therapeutic agent to treat a metabolic disease.

In another embodiment, a process for preparing a compound having the formula (VII-f) is disclosed

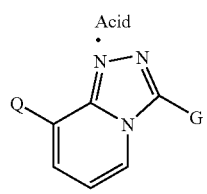

(VII-f)

in which said process comprises reacting a hydrazide of formula VII-d with a carboxylic acid or Ph$_3$PCl$_2$/diisopropyl ethylamine in the presence of a solvent at elevated temperature to afford a 1,2,4-triazolopyridine of formula VII-e and then contacting the 1,2,4-triazolopyridine of formula VII-e with an appropriate acid to provide the compound of formula (VII-f):

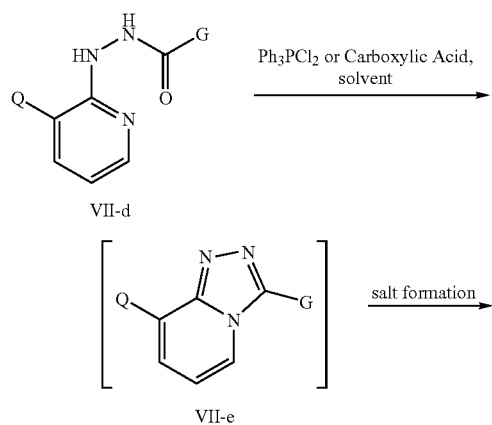

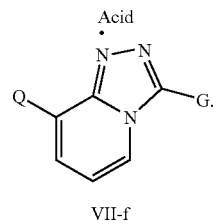

VII-f

In one embodiment, the processes are those in which the hydrazide of formula VII-d is reacted with the carboxylic acid in the presence of a solvent.

In one embodiment, the processes are those in which the hydrazide of formula VII-d is reacted with the carboxylic acid in the presence of a solvent at reflux.

In one embodiment, the processes are those in which the carboxylic acid is selected from acetic acid, p-tosic acid, benzoic acid, 2-,3- or 4-chlorobenzoic acid, 4-fluorobenzoic acid, 2-chlorobenzeneacetic acid, 2- or 4-methylbenzoic acid, 4-methoxybenzoic acid, 2,6-dimethylbenzoic acid, 2,6-dimethoxybenzoic acid, 2-methylpropionic acid and 2,2-dimethylpropanoic acid.

In one embodiment, the processes are those in which solvent is selected from toluene, 1-propanol and mixtures thereof, preferably toluene.

In another embodiment, the processes are those in which the hydrazide of formula VII-d

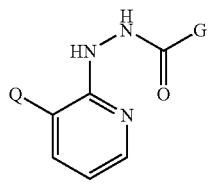

VII-d is prepared by reacting a hydrazinylpyridinyl hydrochloride of formula VII-b with an acid of formula VII-c and oxalyl chloride in a solvent in the presence of a base:

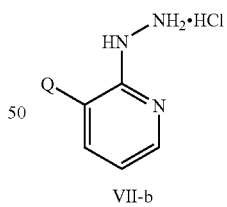

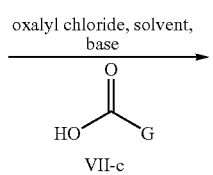

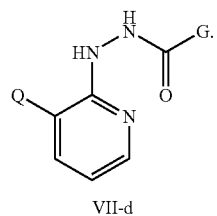

VII-d

In one embodiment, the processes are those in which the reaction of the hydrazinylpyridinyl hydrochloride of formula VII-b with an acid of formula VII-c and oxalyl chloride is carried out at ambient temperature.

In one embodiment, the processes are those in which the solvent used in the reaction of the hydrazinylpyridinyl hydrochloride of formula VII-b with an acid of formula VII-c and oxalyl chloride is selected from toluene, N,N-dimethylformamide, diethylamine, tetrahydrofuran, water, dichloromethane, 2-methyl THF, methyl tert-butyl ether and mixtures thereof, preferably, N,N-dimethylformamide, tetrahydrofuran and mixtures thereof.

In one embodiment, the processes are those in which the base used in the reaction of the hydrazinylpyridinyl hydrochloride of formula VII-b with an acid of formula VII-c and oxalyl chloride is selected from sodium hydroxide, potassium carbonate, triethylamine and dipotassium phosphate, preferably sodium hydroxide and potassium carbonate, more preferably, potassium carbonate.

In another embodiment, the processes are those in which the hydrazinylpyridinyl hydrochloride of formula VII-b

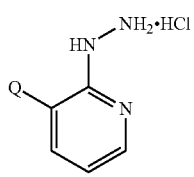

VII-b are prepared by first reacting a halopyridine of formula VII-a with a hydrazine at an elevated temperature followed by HCl salt formation with hydrochloric acid to form the hydrazinylpyridinyl hydrochloride of formula VII-b:

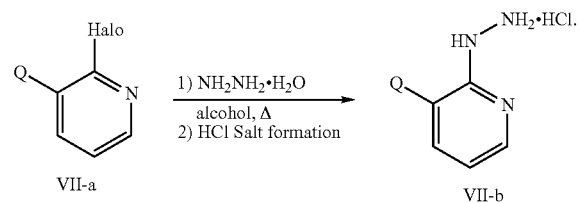

In one embodiment, the processes are those in which the halopyridine of formula VII-a is reacted with the hydrazine in an alcohol, preferably, isopropanol, 1-propanol, 1,4-dioxane, dimethoxyethane, and mixtures thereof, or ether.

In one embodiment, the processes are those in which the halopyridine of formula VII-a is reacted with the hydrazine at 90-100° C., preferably, 92-94° C.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Young, S. D. et al., *Antimicrobial Agents and Chemotherapy*, 2602-2605 (1995).

To the extent that compounds of the formula I, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

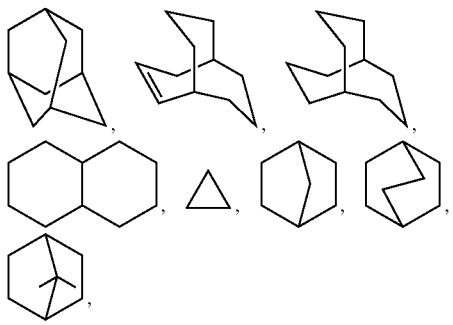

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

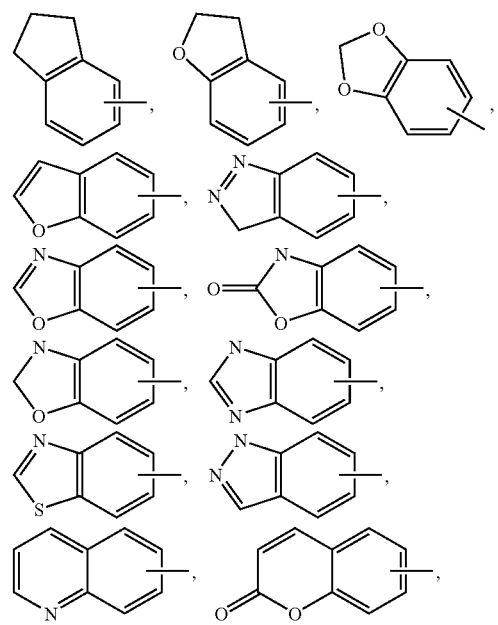

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diaryalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl", "heterocyclic system" or "heterocyclic ring" is intended to mean a stable 3- to 14-membered monocyclic, bicyclic or tricyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —NO$_2$ group.
The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, bisulfate and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., p. 1418 (1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
a) *The Practice of Medicinal Chemistry*, Camille G. Wermuth et al., Ch. 31 (Academic Press, 1996);
b) *Design of prodrugs*, edited by H. Bundgaard (Elsevier, 1985);
c) *A Textbook of Drug Design and Development*, P. Krogsgaard-Larson and H. Bundgaard, eds., Ch. 5, pp. 113-191 (Harwood Academic Publishers, 1991); and
d) *Hydrolysis in Drug and Prodrug Metabolism*, Bernard Testa and Joachim M. Mayer (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization. In addition, the compounds of formula I may exist in tautomeric form. Such tautomeric forms of the formula I are also contemplated herein as part of the present invention.

"Stable compound" and "stable structure" are meant to indicate a compound that is sufficiently robust to survive isolation, handling and storage to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit the activity of the enzyme 11-beta-hydroxysteroid dehydrogenase type I or effective to treat or prevent metabolic or other disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

Compounds of the present invention may be prepared as shown in the following reaction schemes and description thereof, as well as relevant literature procedures that may be used by one skilled in the art. Exemplary reagents and procedures for these reactions appear hereinafter and in the working Examples.

SCHEME I

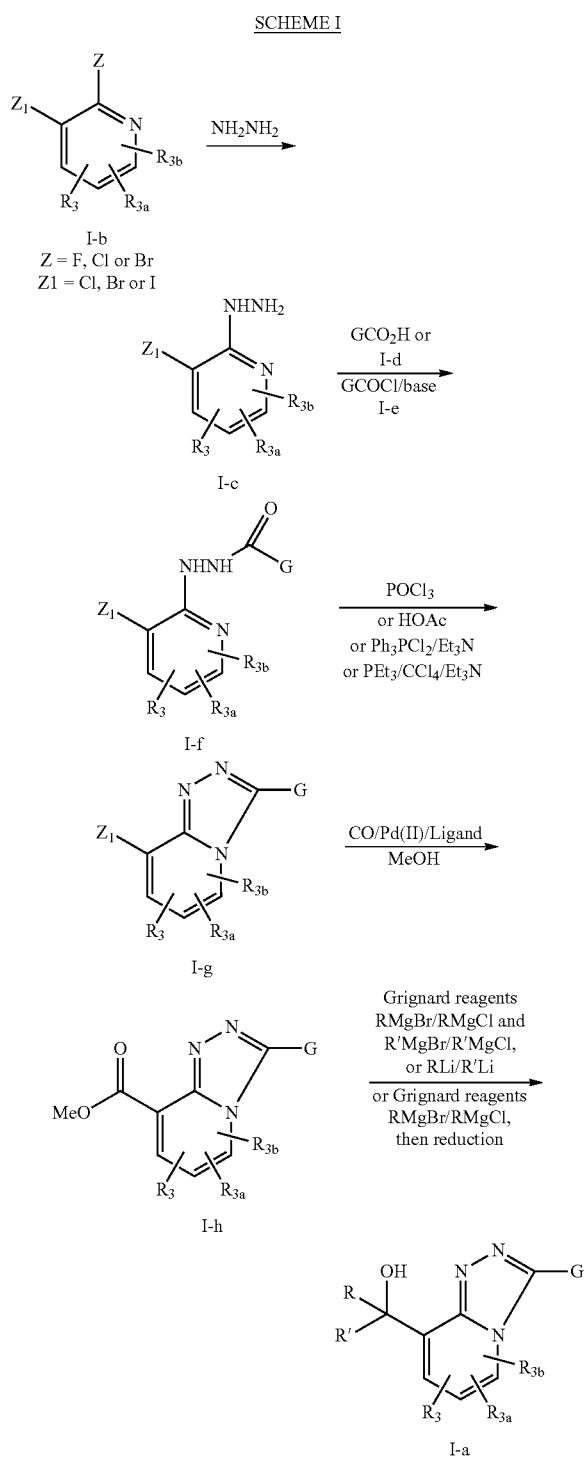

Scheme I describes a method for preparing compounds of formula I-a (a subset of compounds of formula I). A fluoro-, chloro- or bromopyridine intermediate I-b can be obtained commercially, prepared by methods known in the literature or by other methods known to one skilled in the art. Reaction of a compound of formula I-b with hydrazine was carried out at an elevated temperature to provide an intermediate I-c. Acylation of an intermediate I-c with an acid I-d using an appropriate set of amide coupling reagents such NMM/isobutylchloroformate, EDAC/HOBT or other reagents described in Bodanszky, M., *The Practice of Peptide Synthesis,* 2nd Ed. (Spring-Verlag, 1993) provides a hydrazide intermediate I-f. Alternatively, a hydrazide I-c can be prepared from the reaction of I-c and an acid chloride I-e in the presence of an appropriate base such as DIEA or TEA. Formation of 1,2,4-triazolopyridine I-g can be achieved from the reaction of I-f with $Et_3P/CCl_4$ in the presence of a base such as TEA/Hunig's base, or with $Ph_3PCl_2$ in the presence of a base such as TEA. Formation of 1,2,4-triazolopyridine I-g can also be achieved from I-f in the presence of acetic acid at an elevated temperature, either by a conventional heating or a microwave reactor. Alternatively, formation of 1,2,4-triazolopyridine I-g can be achieved from the reaction of I-f with $POCl_3$ at an elevated temperature or by other methods known to one skilled in the art. Formation of 1,2,4-triazolopyridine methyl carboxylate I-h can be achieved by palladium catalyzed carbonation reaction in the presence of CO and methanol. The ester I-h can be treated with Grignard reagents or organo lithium reagents to generate carbinol I-a, or treated with Grignard reagent and followed by reduction using reagent such as NaBH4 to generate hydroxyl compound I-a (R'=hydrogen), or by other methods known to one skilled in the art.

SCHEME II

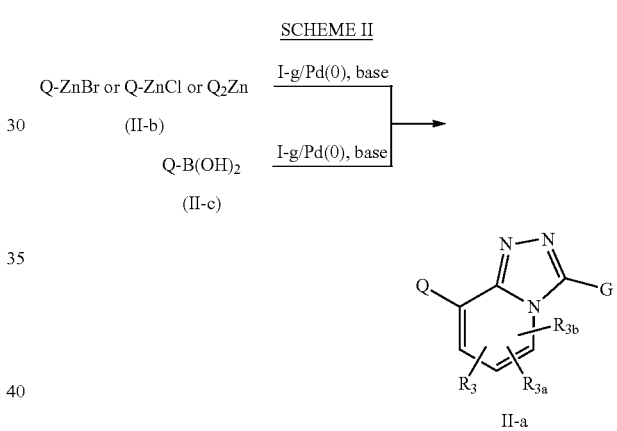

Scheme II describes a method for preparing compounds of formula II-a (a subset of compounds of formula I). Reagents II-b and or II-c can be obtained commercially, prepared by methods known in the literature or by other methods known to one skilled in the art. Formation of a compound II-a can be obtained via coupling reaction of zinc reagents II-b or boronic acid II-c with a bromo-, chloro- or iodo-substituted intermediate I-g ($Z_1$ is Br, Cl or I) in the presence of palladium catalyst. The reactions can be carried out at room temperature, or with heating, or done in a microwave reactor.

SCHEME III

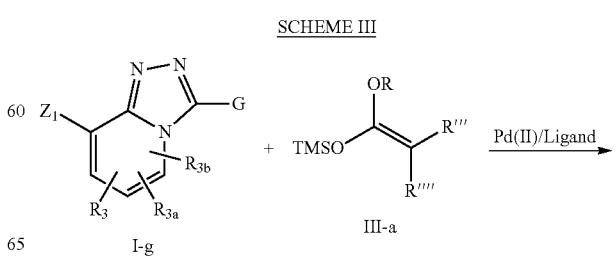

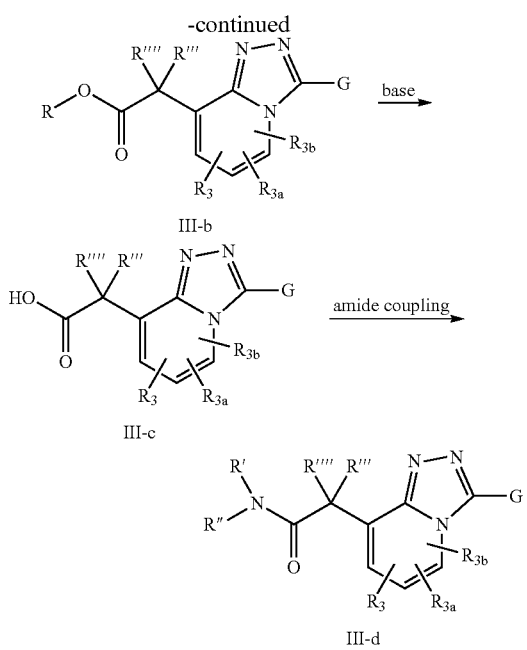

Scheme III describes a method for preparing compounds of formula III-b, III-c, and III-d (a subset of compounds of formula Iaa). Formation of compound III-b can be obtained via coupling reaction of III-a with a bromo-, or iodo-substituted intermediate I-g ($Z_1$ is Br, I) in the presence of palladium catalyst and a base such as potassium carbonate and zinc fluoride at elevated temperature. The reactions can be carried out under a conventional procedure or done in a microwave reactor (*J. Am. Chem. Soc.*, 125:11176 (2003)). Alternatively, compound III-b can be prepared by other methods known to one skilled in the art. Acid III-c can be obtained by hydrolyzing III-b using base such as LiOH. Formation of amide III-d can be achieved by coupling of acid III-c with an amine R'R"NH using an appropriate set of amide coupling reagents such NMM/isobutylchloroformate, EDAC/HOBT or other reagents described in Bodanszky, M., *The Practice of Peptide Synthesis*, 2nd Ed. (Spring-Verlag, 1993). Alternatively, an amide III-d can be prepared from the reaction of a compound of formula III-b and an amine at elevated temperature, or by other methods known to one skilled in the art.

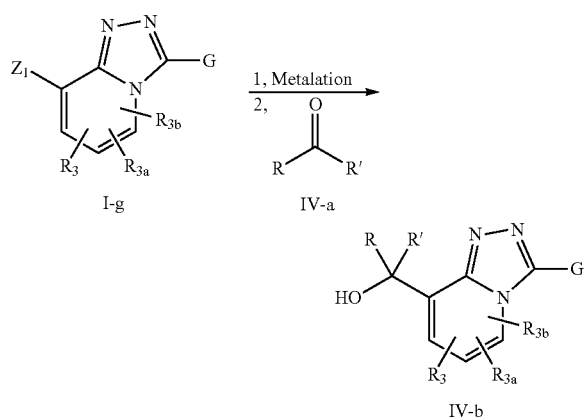

Scheme IV describes a method for preparing compounds of formula IV-b (a subset of compounds of formula Iaa or Iee). Formation of a compound IV-b can be obtained via metalation (metal-halogen exchange) of I-g by using alkyl metal reagent such as BuLi or isopropyl magnesium chloride, followed by addition of aldehyde or ketone IV-a to generate IV-b. Alternatively, compound IV-b can be prepared by other methods known to one skilled in the art.

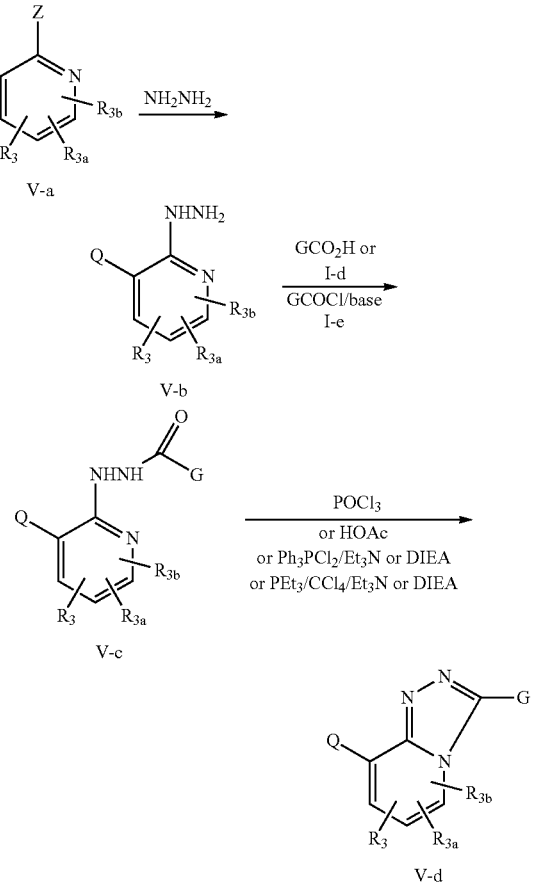

Scheme V describes an alternative method for preparing compounds of formula V-d (a subset of compounds of formula Iaa or Iee). A fluoro-, chloro- or bromopyridine intermediate V-a can be obtained commercially, prepared by methods known in the literature or by other methods known to one skilled in the art. Reaction of a compound of formula V-a with hydrazine in a suitable solvent such as 1-propanol or isopropyl alcohol can be carried out at an elevated temperature to provide an intermediate V-b. V-b may be isolated directly or via a suitable salt form (e.g., HCl salt). Acylation of an intermediate V-b with an acid I-d using an appropriate set of amide coupling reagents such NMM/isobutylchloroformate, EDAC/HOBT or other reagents described in Bodanszky, M., *The Practice of Peptide Synthesis*, 2nd Ed. (Spring-Verlag, 1993) provides a hydrazide intermediate V-c. Alternatively, a hydrazide V-c can be prepared from the reaction of a compound of formula V-b and an acid chloride I-e (which may be prepared by reaction of acid I-d with oxalyl chloride) in the presence of a suitable solvent such as toluene, DMF, or THF) in the presence of an appropriate base such as NaOH, $K_2CO_3$, DIEA or TEA. Formation of 1,2,4-triazolopyridine II-a can be achieved from the reaction of V-c with $Et_3P/CCl_4$ in the presence of a base such as TEA/Hunig's base, or $Ph_3PCl_2$ in the presence of a base such as TEA or DIEA. Formation of 1,2,4-triazolopyridine II-a can also be achieved from V-c in the presence of a carboxylic acid, such as acetic acid, p-tosic acid, benzoic acid, 2-,3- or 4-chlorobenzoic acid, 4-fluorobenzoic acid, 2-chlorobenzeneacetic acid, 2- or 4-methylbenzoic acid, 4-methoxybenzoic acid, 2,6-dimethylbenzoic acid, 2,6-dimethoxybenzoic acid, 2-methylpropionic acid and 2,2-dimethylpropanoic acid, in a solvent, such as toluene, at an elevated temperature, such as reflux, either under a conventional procedure or a microwave reactor to afford 1,2,4-triazolopyridine V-d. Alternatively, formation of 1,2,4-triazolopyridine V-d can be achieved from the reaction of V-c with $POCl_3$ at an elevated temperature or by other methods known to one skilled in the art.

SCHEME VI

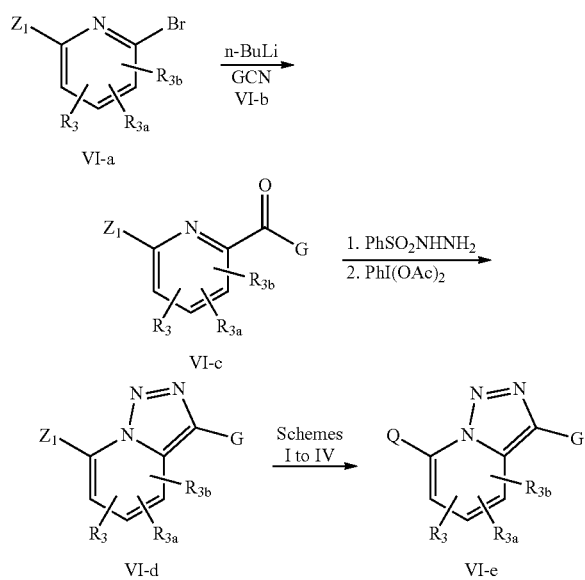

Scheme VI describes a method for preparing compounds of formula VI-e (a subset of compounds of formula Idd). A bromopyridine intermediate VI-a can be obtained commercially, prepared by methods known in the literature, or by other methods known to one skilled in the art. Treatment of a compound of formula VI-a with n-BuLi or other metallating reagents followed by addition of a compound VI-b provides a ketone intermediate VI-c. Formation of a 1,2,3-triazolopyridine VI-d can be achieved by the reaction of a compound VI-c and benzenesulfonohydrazide in the presence of a base such as morpholine (*Tetrahedron*, 53:8257-8268 (1997)), or by other methods known to one skilled in the art followed by cyclization with a reagent such as iodobenzene diacetate. Formation of a compound VI-e can be achieved using similar transformations described in Schemes I to IV, or by other methods known to one skilled in the art.

EXAMPLES

The following working Examples serve to better illustrate, but not limit, some of the preferred embodiments of the present invention.

General

The term HPLC refers to a Shimadzu high performance liquid chromatography with one of following methods:

Method A: YMC or Phenomenex C18 5 micron 4.6×50 mm column using a 4 minute gradient of 0-100% solvent B [90% MeOH: 10% $H_2O$:0.2% $H_3PO_4$] and 100-0% solvent A [10% MeOH:90% $H_2O$:0.2% $H_3PO_4$] with 4 mL/min flow rate and a 1 min. hold, an ultra violet (UV) detector set at 220 nm.

Method B: Phenomenex S5 ODS 4.6×30 mm column, gradient elution 0-100% B/A over 2 min (solvent A=10% MeOH/$H_2O$ containing 0.1% TFA, solvent B=90% MeOH/$H_2O$ containing 0.1% TFA), flow rate 5 mL/min, UV detection at 220 nm.

Method C: YMC S7 ODS 3.0×50 mm column, gradient elution 0-100% B/A over 2 min (solvent A=10% MeOH/$H_2O$ containing 0.1% TFA, solvent B=90% MeOH/$H_2O$ containing 0.1% TFA), flow rate 5 mL/min, UV detection at 220 nm.

The term prep HPLC refers to an automated Shimadzu HPLC system using a mixture of solvent A (10% MeOH/ 90%$H_2O$/0.2%TFA) and solvent B (90% MeOH/10%$H_2O$/ 0.2% TFA). The preparative columns were packed with YMC or Phenomenex ODS C18 5 micron resin or equivalent.

Procedure for Characterizing the Crystal Forms

Single Crystal Data

A Bruker SMART 2K CCD diffractometer equipped with graphite-monochromated Cu Kα radiation, (λ=1.54056 Å) was used to collect diffraction data at room temperature. A full data set was collected using the ω scan mode over the 2θ range with a crystal-to-detector distance of 4.98 cm. An empirical absorption correction utilized the SADABS routine associated with the diffractometer (Bruker AXS. 1998, SMART and SAINTPLUS. Area Detector Control and Integration Software, Bruker AXS, Madison, Wis., USA). The final unit cell parameters were determined using the entire data set.

All structures were solved by direct methods and refined by the full-matrix least-squares techniques, using the SHELXTL software package (Sheldrick, G M. 1997, SHELXTL. Structure Determination Programs. Version 5.10, Bruker AXS, Madison, Wis., USA.). The function minimized in the refinements was $\Sigma_w(|F_O|-|F_C|)^2$. R is defined as $\Sigma||F_O|-|F_C||/\Sigma|F_O|$ while $R_w=[\Sigma_w(|F_O|-|F_C|)^2/\Sigma_w|F_O|^2]^{1/2}$, where w is an appropriate weighting function based on errors in the observed intensities. Difference Fourier maps were examined at all stages of refinement. All non-hydrogen atoms were refined with anisotropic thermal displacement parameters. The hydrogen atoms associated with hydrogen bonding were located in the final difference Fourier maps while the positions of the other hydrogen atoms were calculated from an idealized geometry with standard bond lengths and angles. They were assigned isotropic temperature factors and included in structure factor calculations with fixed parameters.

Alternatively, single crystal data were collected on a Bruker-Nonius[1] CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418

Å). Indexing and processing of the measured intensity data were carried out with the HKL2000 software package[2] in the Collect program suite.[3] Alternately, single crystal data were collected on a Bruker-AXS APEX2 CCD system using Cu Kα radiation (λ=1.5418 Å). Indexing and processing of the measured intensity data were carried out with the APEX2 software package/program suite[4].

[1] BRUKER AXS, Inc., 5465 East Cheryl Parkway Madison, Wis. 53711 USA
[2] Otwinowski, Z. et al., *Macromolecular Crystallography*, Academic, NY, publ., Carter, W. C., Jr. et al., eds., Vol. 276, pp. 307-326 (1997).
[3] Collect Data collection and processing user interface: Collect: Data collection software, R. Hooft, Nonius B. V., 1998.
[4] APEX2 Data collection and processing user interface: *APEX2 User Manual*, Vol. 27; BRUKER AXS, Inc., 5465 East Cheryl Parkway Madison, Wis. 53711 USA.

When indicated, crystals were cooled in the cold stream of an Oxford cryo system[5] during data collection.

[5] Oxford Cryosystems Cryostream cooler: Cosier, J. et al., *J. Appl. Cryst.*, 19:105 (1986).

The structures were solved by direct methods and refined on the basis of observed reflections using either the SDP[6] software package with minor local modifications or the crystallographic packages MAXUS[7] or SHELXTL[4].

[6] SDP, Structure Determination Package, Enraf-Nonius, Bohemia N.Y. 11716. Scattering factors, including f' and f'', in the SDP software were taken from the "International Tables for Crystallography" (Kynoch Press, Birmingham, England, 1974), Vol. IV, Tables 2.2A and 2.3.1.
[7] MaXus solution and refinement software suite: Mackay, S. et al., maXus: a computer program for the solution and refinement of crystal structures from diffraction data.

The derived atomic parameters (coordinates and temperature factors) were refined through full matrix least-squares. The function minimized in the refinements was $\Sigma_W(|F_O|-|F_C|)^2$. R is defined as $\Sigma||F_O|-|F_C||/\Sigma|F_O|$ while $R_W=[\Sigma_W(|F_O|-|F_C|)^2/\Sigma_W|F_O|^2]^{1/2}$, where w is an appropriate weighting function based on errors in the observed intensities. Difference maps were examined at all stages of refinement. Hydrogens were introduced in idealized positions with isotropic temperature factors, but no hydrogen parameters were varied.

PXRD

X-ray powder diffraction (PXRD) data were obtained using a Bruker C2 GADDS (General Area Detector Diffraction System). The radiation was Cu Kα (40 KV, 50 mA). The sample-detector distance was 15 cm. Powder samples were placed in sealed glass capillaries of 1 mm or less in diameter; the capillary was rotated during data collection. Data were collected for $3 \leq 2\theta \leq 35°$ with a sample exposure time of at least 2000 seconds. The resulting two-dimensional diffraction arcs were integrated to create a traditional 1-dimensional PXRD pattern with a step size of 0.02 degrees 2θ in the range of 3 to 35 degrees 2θ.

Alternatively, X-ray powder diffraction (PXRD) data were obtained using a Bruker GADDS manual chi platform goniometer. Powder samples were placed in thin walled glass capillaries of 1 mm or less in diameter; the capillary was rotated during data collection. The sample-detector distance was 17 cm. The radiation was Cu Kα (λ=1.5418 Ang). Data were collected for 3<2θ<35° with a sample exposure time of at least 300 seconds.

DSC

Differential scanning calorimetry (DSC) experiments were performed in a TA Instruments™ model Q2000, Q1000 or 2920. The sample (about 2-6 mg) was weighed in an aluminum pan and recorded accurately to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

TGA

Thermal gravimetric analysis (TGA) experiments were performed in a TA Instruments™ model Q500 or 2950. The sample (about 10-30 mg) was placed in a platinum pan previously tared. The weight of the sample was measured accurately and recorded to a thousandth of a milligram by the instrument. The furnace was purged with nitrogen gas at 100 mL/min. Data were collected between room temperature and 300° C. at 10° C./min heating rate.

Moisture Sorption

Moisture sorption isotherms were collected in a VTI SGA-100 Symmetric Vapor Analyzer using approximately 10 mg of sample. The sample was dried at 60° C. until the loss rate of 0.0005 wt %/min was obtained for 10 minutes. The sample was tested at 25° C. and 3 or 4, 5, 15, 25, 35, 45, 50, 65, 75, 85, and 95% RH. Equilibration at each RH was reached when the rate of 0.0003 wt %/min for 35 minutes was achieved or a maximum of 600 minutes.

ABBREVIATIONS

The following abbreviations are employed in the Examples and elsewhere herein:
Ph=phenyl
Bn=benzyl
i-Bu=iso-butyl
Me=methyl
Et=ethyl
Pr=propyl
Bu=butyl
AIBN=2,2'-Azobisisobutyronitrile
Aq.=aqueous
Boc or BOC=tert-butoxycarbonyl
Cbz=carbobenzyloxy or carbobenzoxy or benzyloxycarbonyl
CO=carbon monoxide
DCM=dichloromethane
DEAD=Diethyl azodicarboxylate
DIAD=Diisopropyl azodicarboxylate
DIEA=N,N-diisopropylethylamine
DMA=N,N-dimethylacetylamide
DMF=N,N-dimethylformamide
DMSO=dimethylsulfoxide
EtOAc=ethyl acetate
EDAC=3-ethyl-3'-(dimethylamino)propyl-carbodiimide hydrochloride (or 1-[(3-(dimethyl)amino)propyl])-3-ethylcarbodiimide hydrochloride)
FMOC=fluorenylmethoxycarbonyl
HOAc or AcOH=acetic acid
HOAT=1-hydroxy-7-azabenzotriazole
HOBT=1-hydroxybenzotriazole
IPA=isopropyl alcohol or isopropanol
LAH=lithium aluminum hydride
MTBE=methyl tertiary butyl ether
mCPBA=3-Chloroperoxybenzoic acid
NMM=N-methyl morpholine
NBS=N-Bromosuccinimide
n-BuLi=n-butyllithium
Oxone®=Monopersulfate
Pd/C=palladium on carbon
PtO2=platinum oxide
PyBOP reagent=benzotriazol-1-yloxy-tripyrrolidino phosphonium hexafluorophosphate
RH=relative humidity
$SOCl_2$=Thionyl chloride
TBAF=tetrabutylammonium fluoride
TBS=tert-Butyldimethylsilyl
TMS=trimethylsilyl TEA=triethylamine
TFA=trifluoroacetic acid
THF=tetrahydrofuran
Eq. or equiv=equivalent(s)
min=minute(s)
h or hr=hour(s)
L=liter
mL=milliliter
μL=microliter
g=gram(s)
mg=milligram(s)
mol=mole(s)
mmol=millimole(s)
meq=milliequivalent
rt or RT=room temperature
sat or sat'd=saturated
aq.=aqueous
TLC=thin layer chromatography
HPLC=high performance liquid chromatography
HPLC Rt=HPLC retention time
LC/MS=high performance liquid chromatography/mass spectrometry
MS or Mass Spec=mass spectrometry
NMR=nuclear magnetic resonance
mp=melting point
$K_3PO_4$=potassium phosphate
$Na_2SO_4$=sodium sulfate
$SiO_2$=silicon dioxide
EA=ethyl amine
$Et_2O$=diethyl ether
MeOH=methanol
$H_3PO_4$=phosphoric acid
$MgSO_4$=magnesium sulfate
$Pd(dppf)Cl_2[CH_2Cl_2]$=bis(diphenylphosphino)ferrocene] dichloropalladium(II), complex with dichloromethane (1:1)
$ZnF_2$=Zinc Fluoride
$Pd(dba)_2$=bis(dibenzylideneacetone)palladium
$P(tBu)_3$=tributylphosphine Example 1

2-(3-(1-(4-Chlorophenyl)cyclopropyl)-[1,2,4]triazolo[4,3-a]pyridin-8-yl) propan-2-ol

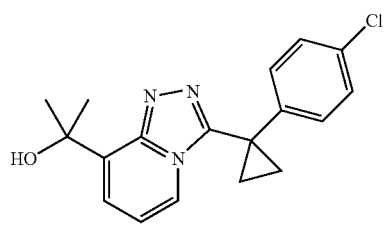

Compound 1A

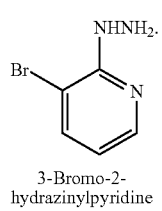

3-Bromo-2-hydrazinylpyridine

To a solution of 2-chloro-3-bromopyridine (14.5 g, 75.1 mmol) in 100 mL of dioxane was added anhydrous hydrazine (35.4 mL, 1130 mmol) at RT. The reaction mixture was heated at reflux for 15 h, and then cooled to RT. After most of the solvent was removed under reduced pressure, the resulting residue was diluted with ethyl acetate, washed with water, dried over $Na_2SO_4$, and concentrated to provide a residue. Recrystallization of the residue in ethyl acetate and hexanes gave compound 1A (12.9 g, 91%) as a solid. LC/MS (m/z)= 188 (M+H)+.

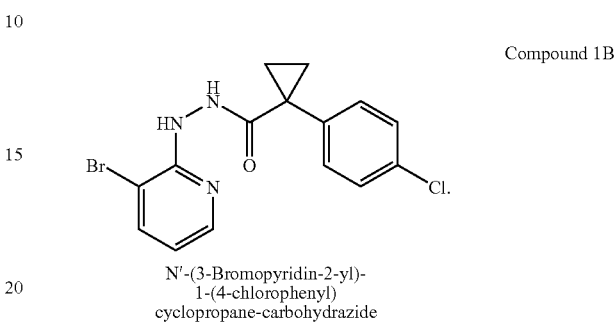

Compound 1B

N'-(3-Bromopyridin-2-yl)-1-(4-chlorophenyl)cyclopropane-carbohydrazide

A stirred solution of 1-(4-chlorophenyl)cyclopropanecarboxylic acid (8.71 g, 44.3 mmol) and NMM in THF (200 mL) was cooled 0° C. Once at the prescribed temperature, isobutyl chloroformate was added dropwise over 10 min, and the resulting white suspension was stirred for 1h. After this time, a solution of compound 1A (8.33g, 44.3 mmol) in THF (250 mL) was added over 10 min. Upon completion of addition, the reaction mixture was stirred for 15 min. At the conclusion of this period, the reaction mixture was warmed to RT, where it was stirred for 2 h. After this time, the reaction mixture was partitioned between ethyl acetate and water. The organic phase was separated, dried over $Na_2SO_4$, and then concentrated in vacuo to afford compound 1B (10.2 g, 27.8 mmol, 63% yield) as an off-white solid. LC/MS (m/z)=366 (M+H)+.

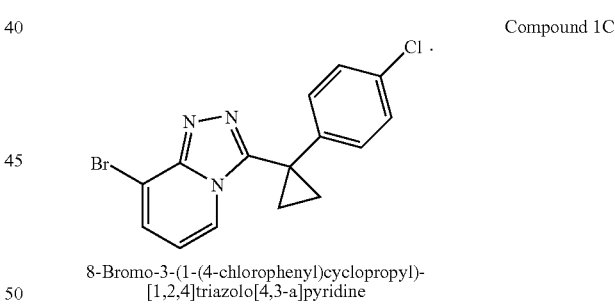

Compound 1C

8-Bromo-3-(1-(4-chlorophenyl)cyclopropyl)-[1,2,4]triazolo[4,3-a]pyridine

A stirred solution of compound 1B (10 g, 27.3 mmol), carbon tetrachloride (31.6 mL, 327 mmol) and Hunig's Base (28.6 mL, 164 mmol) in 275 ml of THF was cooled to 0° C. Triethylphosphine (12.1 mL, 82 mmol) was added dropwise to the solution over 10 min. Upon completion of addition, the reaction mixture was slowly warmed to RT, where it stirred for 16 h. After this time, the reaction mixture was quenched with $H_2O$ (100 mL), and extracted ethyl acetate (2×200 mL). The pooled organic phases were washed with brine, dried over $Na_2SO_4$, and then concentrated in vacuo to afford a yellow solid. The yellow solid was triturated with 100 ml of ethyl acetate/Hexane (2:1, v/v), and the resulting mixture was filtered. The resulting solid was rinsed with more ethyl acetate (50 ml) and compound 1C (7.2 g) was collected via filtration as a pale-yellow solid. LC/MS (m/z)=348 (M+H)+.

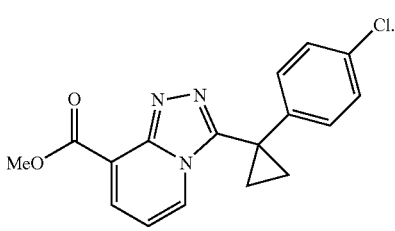

Methyl 3-(1-(4-chlorophenyl)cyclopropyl)-
[1,2,4]triazolo[4,3-a]pyridine-8-carboxylate A pressure reaction flask was charged with compound 1C (2.5 g, 7.17 mmol), 1,3-bis(diphenylphosphino)propane (0.592 g, 1.43 mmol), triethylamine (3.00 mL, 21.5 mmol), and MeOH (50 mL). The mixture was bubbled with CO for 2 min, then sealed and charged with 25 psi of CO (gas). The reaction mixture was heated to 80° C., where it was stirred for 24 h. After this time, the MeOH was removed in vacuo and 20 ml of brine was added. The resulting mixture was extracted with EtOAc (3×30 ml). The combined organic layers were washed with brine, dried over $Na_2SO_4$, filtered and concentrated to provide the crude product. The crude product was purified by column chromatography (eluted with EtOAc/hexane (0 to 100%)) to provide compound 1D (2.02 g) as a light yellow foam. LC/MS (m/z)=328 (M+H)+.

Example 1

Under a nitrogen atmosphere at RT, a microwave tube was charged with a solution of compound 1D (131 mg, 0.40 mmol) in 3 ml of THF, followed by addition of methylmagnesium chloride (400 μL, 3 M in THF, 1.2 mmol). Upon completion of addition, the reaction was stirred at RT for 1 h, and then heated to 65° C. where it stirred for 6 h. After this time, the reaction mixture was cooled to RT. The reaction mixture was quenched with brine (3 ml) and extracted with EtOAc (3×5ml). The combined organic layers were concentrated and purified via column chromatography (40 g silica gel column, from 0% to 100% EtOAc/Hexane) to provide Example 1 (45 mg), as a white foam. LC/MS (m/z)=328 (M+H)+. $^1$H NMR (400 MHz, Chloroform-d): δ1.51 (dd, J=6.9, 4.8 Hz, 2H), 1.66 (dd,J=6.8, 4.8 Hz, 2H,), 1.74 (s, 6H), 5.12 (s, 1H), 6.70 (t,J=4.0 Hz, 1H), 7.04 (dt, J=12, 4.0 Hz, 2H),7.11 (d,J=8.0 Hz, 1H), 7.21 (dt,J=8.0, 4.0 Hz, 2H), 7.21 (d,J=7.8, Hz, 1H). $^{13}$C NMR (100.6 MHz, Chloroform-$d_6$): δ15.25, 19.83, 29.24, 72.04, 113.91, 121.02, 121.17, 127.75, 128.99, 132.73, 137.19, 138.37, 148.27, 149.23.

Example 1G 2-(3-(1-(4-Chlorophenyl)cyclopropyl)-[1,2,4]triazolo[4,3-a]pyridin-8-yl)propan-2-ol HCl Salt

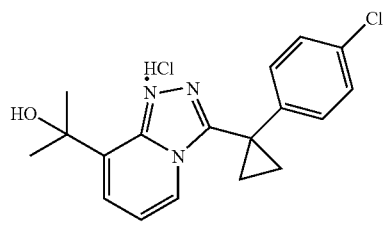

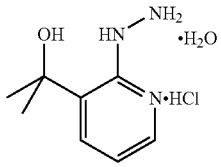

2-(2-Hydrazinylpyridin-3-yl)
propan-2-ol Hydrochloride
Monohydrate

To a 2.0-liter round-bottomed flask was charged sequentially 2-(2-fluoropyridin-3-yl)propan-2-ol (60.0 g, 386.7 mmol., 1.0 equiv.), 1-propanol (120 mL) and $Na_2CO_3$ (43.0 g, 405.7 mmol., 1.05 equiv). Hydrazine monohydrate (96.8 g; 1930 mmol., 5.2 equiv.) was charged to the flask and the resulting mixture was heated to 92-94° C. Once at the prescribed temperature, the reaction mixture was monitored by HPLC until the 2-(2-fluoropyridin-3-yl)propan-2-ol starting material was consumed, which was about 24-26 h. The resulting biphasic slurry was cooled to 20° C. and then water followed by toluene (900 mL) were added. Upon completion of addition, the resulting mixture was stirred at 20° C. for ~10-15 minutes. After this time, the organic and aqueous phases were allowed to settle for 10 min and then the aqueous phase was separated. The organic layer was washed with 20% aqueous brine solution (450 mL) and then concentrated in vacuo at ~55-60° C. to provide a toluene solution (~240 mL). The toluene solution was cooled to 25° C. and 1-propanol (60 mL) was added. To the resulting solution was added a 5-6 N HCl in IPA solution (0.6 equiv.) during a 30-40 min period. Upon completion of addition, a seed of previously prepared 2-(2-hydrazinylpyridin-3-yl)propan-2-ol hydrochloride monohydrate (1.0% wt.) and additional 5-6 NHCl in IPA solution (0.7 equiv.) were added. The resulting slurry was stirred at 20° C. for at least 12 hr and then filtered. The filter cake was washed with a mixture of 1-propanol and toluene (9:1, v/v, 200 mL×3) and then dried in vacuo at the room temperature for 4-5 hrs. After this time, the filter cake was further dried under nitrogen at 40° C. for 2-3 h and then at the room temperature for about 16 hours to provide crude compound 1E (52.1 g, 60.7% yield, HPLC purity >99% area percent).

Compound 1E was also recrystallized by mixing crude 2-(2-hydrazinylpyridin-3-yl)propan-2-ol hydrochloride monohydrate (25 g, 113 mmol), IPA (150 mL) and 1-propanol (100.0 mL) in a 500-mL round-bottomed flask. The resulting slurry was warmed under nitrogen to 55-60° C. where it stirred for ~5-10 minutes. After this time, toluene (100 ml) was added. The resulting mixture was seeded with 2-(2-hydrazinylpyridin-3-yl)propan-2-ol hydrochloride monohydrate (1.0% wt.) and then additional toluene (100 mL, total toluene, 200 mL) was added (total time for complete toluene addition was 30 minutes). Upon completion of addition, the mixture was stirred for about 16 hours and then the resulting slurry was filtered. The filter cake was washed with a toluene and isopropyl alcohol solution (2: 1, v/v, 25 mL×2) and then dried in a vacuum oven at the room temperature under nitrogen sweeping for about 16 hours to provide recrystallized Compound 1E (13.4 g, 53% recovery, melting point: 88.1-111.2° C. (dec.)). IR (KBr) 3392, 3329, 3291, 3246, 3202, 3108, 2983, 1653, 1625, 1600, 1552, 1455, 1390, 1249, 1171, 1105, 1050, 963, 940, 878, 798, 788, 765, 690, 502 $cm^{-1}$. $^1$H NMR (400 MHz, DMSO-$d_6$): δ1.61 (s, 6H), 6.16 (br s, 1H), 6.91 (dd,J=7.3, 5.4 Hz, 1H), 7.62 (d,J=7.2 Hz, 1H), 8.03 (d, J=3.9 Hz, 1H), 8.93 (s, 1H), 9.65 (br s, 2H). $^{13}$C NMR (100.5 MHz, DMSO-d$_6$): δ30.0, 72.0, 115.8, 129.2, 135.2, 141.8, 153.2. HRMS Compound 1E (M+1): calcd 168.1137, found, 168.1137. Anal. Calcd. for Compound 1E: C, 43.35; H, 7.27; N, 18.95; Cl, 15.99. Found: C, 43.53; H, 7.29; N, 19.06, Cl, 15.99.

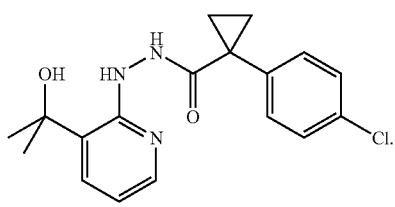

Compound 1F 1-(4-Chlorophenyl)-N'-(3-(2-hydroxypropan-2-yl)pyridin-2-yl)cyclopropanecarbohydrazide To a slurry of 1-(4-chlorophenyl)cyclopropanecarboxylic acid (34.7 g; 177 mmoles; 1.1 equiv.) in toluene (142 mL) was added DMF (124 μL; 1.6 mmoles; 0.01 equiv.). Upon completion of addition, the slurry was stirred at ~25° C. for ~5 minutes and then neat oxalyl chloride (14.8 mL; 167 mmoles; 1.0 equiv.) was added at room temperature over a 20 min. period. The resulting slurry was stirred for ~4 hr (the solids gradually dissolved as the reaction proceeded). In a separate flask, a mixture of compound 1E (35.5 g; 160 mmoles; 1.0 equiv.) and potassium carbonate (51 g; 369 mmoles; 2.3 equiv) in THF (355 mL) was cooled to ~5° C. Once at the prescribed temperature, water (248 mL) was added and the biphasic mixture was stirred for 15 min. At the conclusion of this period, the acid chloride solution was transferred to the biphasic solution over a 20 minute period. Upon completion of the transfer, the reaction mixture was stirred for 30 min. The reaction mixture was analyzed by HPLC, which indicated that the reaction was complete. The aqueous layer was removed and the organic layer was washed with water (180 mL×2) and then concentrated via vacuum distillation at ~60° C. to provide a rich product solution (178 mL). Toluene (70 mL) was added to the rich product solution and the resulting solution was heated to ~70° C. Once at the prescribed temperature, n-heptane (425 mL) was added during a 30 min. period to generate a slurry. The slurry was cooled to ~20° C. where it stirred for 3 hr. After this time, the slurry was filtered. The filter cake was washed with n-heptane (142 mL) and then dried in vacuo at RT for 48 hr to provide crude compound 1F (51 g, yield 92%). Crude compound 1F was suspended in acetonitrile (770 mL) and water (35 mL), and the resulting mixture was heated to ~75° C. where it stirred for 5 minutes in order to achieve full dissolution. The resulting solution was then cooled to ~60° C. Once at the prescribed temperature, water (280 mL) was added during a 1 hour period. The resulting slurry was cooled to ~20° C. during a 2 hr period. Once at the prescribed temperature, the slurry was stirred for two hours. The resulting solids were collected by filtration, washed with water (142 mL) and then dried in vacuo at ~70° C. to afford recrystallized compound 1F (46 g, yield 83%). HPLC purity 99.64%.

Compound 1F was also recrystallized by suspending crude compound 1F (17 g) in methanol (170 mL) and then heating the resulting slurry to reflux in order to achieve full dissolution. Upon dissolution, water (8.5 mL) was added and the resulting slurry was cooled to ~20° C. Once at the prescribed temperature, the slurry was stirred for about 16 hours and then filtered. The filter cake was washed with water (68 mL) and then dried in vacuo at ~70° C. to provide recrystallized compound 1F (14.1 g, yield 83%, melting point 191° C.). IR (KBr) 3355, 3226, 2978, 1633, 1591, 1574, 1541, 1494, 1456, 1384, 1316, 1269, 1240, 1139, 1098, 978, 766, 534 cm$^{-1}$. $^{1}$H NMR (400 MHz, DMSO-d$_6$): δ1.07 (dd,J=6.9, 4.1 Hz, 2H), 1.44 (dd,J=6.8, 4.0 Hz, 2H,), 1.51 (s, 6H), 5.72 (s, 1H), 6.69 (dd,J=7.4, 4.9 Hz, 1H), 7.39 (dd,J=7.6, 1.5 Hz, 1H), 7.43 (dt,J=5.6, 2.3 Hz, 2H), 7.50 (dt, J=5.5, 2.3 Hz, 2H), 7.95 (dd,J=4.9, 1.6 Hz, 1H), 8.97 (d,J=3.2 Hz, 1H), 9.06 (dd,J=3.3 Hz, 1H). $^{13}$C NMR (100.6 MHz, DMSO-d$_6$): δ14.6, 28.6, 28.8, 71.1, 114.4, 127.0, 128.4, 131.6, 131.8, 132.7, 138.7, 145.3, 155.3, 169.7. MS Compound 1F (M+1): m/e, 346.15. Anal. Calcd for Compound 1F: C, 62.52; H, 5.827; N, 12.15; Cl, 10.25. Found: C, 62.58; H, 5.78; N, 12.27, Cl, 10.26.

Example 1G

In a three-necked 50-mL round-bottomed flask, a mixture of compound 1F (1.5 g, 4.34 mmol, 1.0 equiv.), toluene (15 mL) and acetic acid (3 mL, 3.2 g, 52.4 mmol, 12.1 equiv.) was heated to ~100-105° C. where it was stirred for no less than 35.0 hr. After this time, the mixture was analyzed by HPLC, which indicated that the reaction was >97% complete. The reaction mixture was distilled at atmospheric pressure to provide a residue (~10.0 mL). Toluene (15 mL) was added to the residue and the resulting mixture was again concentrated with atmospheric distillation to a volume of ~16.5 mL. The resulting mixture was cooled to 20° C. where it stirred for about 16 hours. At the conclusion of this period, the mixture was diluted with water (12 mL) and then conc. HCl (560 μL, 6.5 mmol, 1.5 equiv.) was added. The resulting mixture was stirred for ~10 min and then the organic layer was separated and discarded. The aqueous layer was extracted with a mixture of toluene/heptane (2:1, v/v, 6 mL). The organic layer was again separated and discarded. Toluene (15 mL) was added to the aqueous layer and the resulting aqueous biphasic mixture was cooled to ~5° C. Once at the prescribed temperature, 10 NNaOH (aqueous, 950 μL; 9.5 mmoles; 2.2 equiv.) was added to adjust the pH to ~14. Upon completion of addition, the resulting mixture was stirred for 15 min and then the organic and aqueous layers were separated. The organic layer was washed with 10% wt. NaCl (aqueous, 7.5 mL) and then diluted with toluene (7.5 mL). The resulting mixture was concentrated by atmospheric distillation to a final volume of ~13.5 mL. This solution was cooled to ~20° C. and then a mixture (~0.5 mL, 0.4 equiv.) of conc. HCl (560 μL, aqueous, 6.5 mmoles; 1.5 equiv) in IPA (1.5 mL) was slowly added followed by a seed of Example 1G (7.9 mg, 0.5%). To the resulting light slurry was added the remainder (~1.5 mL, 1.1 equiv.) of the conc. HCl/IPA mixture over a 10 minute period. Upon completion of addition, the resulting slurry was stirred at ~20° C. for about 16 hours. At the conclusion of this period, the slurry was filtered. The filter cake was washed with toluene (5 mL) and then dried in vacuo to afford crude Example 1G, HPLC Purity 99.29%, 1.2 g, as a white solid. Yield=72.8%.

Alternatively, Example 1G can be prepared as follows:

In a 50-mL three necked round bottomed flask, a mixture of compound 1F (1.0 g, 2.95 mmol, 1 equiv.), toluene (5.1 mL) and acetic acid (1.7 mL, 1.8 g, 29.5 mmol, 10 equiv.) was heated to ~100° C. for 24 hr. The mixture was diluted with toluene (15 mL). The resulting mixture was concentrated by distillation at ~110° C. to provide a solution with a final volume of ~8.0 mL. This solution was cooled to ~20° C. and then a solution (~0.5 mL, 0.5 equiv.) of conc. HCl (540 μL, aqueous, 6.3 mmol., 2.1 equiv.) in isopropyl alcohol (1.5 mL) was added. Upon completion of addition, a seed of Example 1G (11.8 mg) was added to generate a light slurry. To the light slurry was added the remainder (~1.5 mL, 1.6 equiv.) of the conc. HCl/IPA mixture during a 3 minute period. The resulting slurry was stirred at ~20° C. for about 16 hours. At the conclusion of this period, the slurry was filtered. The filter cake was washed with toluene (4 mL) and then dried in vacuo to afford crude Example 1G, ~1.0 g, HPLC Purity 99.13%, as a white solid.

Preparation of Crystalline N-1 Form of Example 1G

Crude Example 1G (1.15 g) was dissolved in EtOH (7.5 mL) at ~65° C. Upon dissolution, n-heptane (7.5 mL) and a seed crystal of Example 1G were added to generate a seed bed, and the resulting light slurry was stirred for ~10 min. After this time, additional n-heptane (15 mL) was added during a 15 min. period. This resulting slurry was stirred at 65° C. for 30 min and then cooled to ~20° C. where it stirred for no less than 16 hours. At the conclusion of this period, the slurry was filtered. The filter cake was washed with 10% ethanol in n-heptanes (5 mL) and then dried in a vacuum oven at 45° C. for about 16 hours to afford Example 1G (1.0 g, yield 63.9%) as a white solid. The material was analyzed by the methods described above to be a crystalline material. The crystalline material was assigned the N-1 form. $^1$H NMR (600.1 MHz, $CD_3OD$-$d_4$): δ1.74 (s, 6H), 1.74, 1.82 (overlapped, dd, J=7.6, 5.1 Hz, 2H, 2H), 7.32 (d,J=8.6 Hz, 2H), 7.32 (d,J=8.6 Hz, 2H), 7.51 (t,J=7.1 Hz, 1H), 8.02 (dd,J=7.3, 0.9 Hz, 1H), 8.51 (dd,J=6.8, 0.9 Hz, 1H). $^{13}$C NMR (125.8 MHz, $CD_3OD$-$d_4$): δ16.1, 20.6, 30.5, 72.6, 119.9, 125.0, 129.6, 130.4, 133.6, 134.6, 136.3, 138.3, 144.5, 150.0.

Alternatively, the crystalline N-1 form of Example 1G was prepared from crude Example 1G as follows:

Crude Example 1G (~1.0 g) was dissolved in EtOH (5 mL) at ~65° C. Upon dissolution, n-heptane (5 mL) was added and the resulting mixture was stirred for ~10 min. to generate a seed bed. The light slurry was stirred for ~10 min and then additional n-heptane (7.5 mL) was added during a 15 minute period. Upon completion of addition, the slurry was stirred for 30 minutes then cooled to ~20° C. where it stirred for about 16 hours. At the conclusion of this period, the slurry was filtered. The filter cake was washed with 10% ethanol in n-heptanes (5 mL) and then dried in a vacuum oven at 45° C. for about 16 hours to afford Example 1G (0.8 g, yield 72.4%) as a white solid. HPLC Purity 99.83% area percent. The solid was determined to have similar physical properties as described above.

Preparation of Crystalline N-2 Form of Example 1G

Crude Example 1G (318 mg) was dissolved in toluene (1.8 L) at 90° C. The resulting solution was stirred at 90° C. for 30 min and then cooled slowly to 20° C. over 3 hours. Once at the prescribed temperature, the cooling bath was turned off and the resulting slurry was stirred for about 16 hours. After this time, the resulting white solid was collected by filtration and dried at 30° C. in a vacuum oven for about 16 hours to provide 220 mg of material. The material was analyzed by PXRD to be a crystalline material. The crystalline material was assigned to be the N-2 form.

Alternatively, the crystalline N-2 form of Example 1G was prepared from crude Example 1G as follows:

Crude Example 1G (100 mg) was dissolved in MTBE (0.6 L) at 75° C. The resulting solution was stirred at 75° C. for 20 minutes and then cooled slowly to 20° C. over 2.5 hours. Once at the prescribed temperature, the cooling bath was turned off and the resulting slurry was stirred for about 16 hours. After this time, the resulting white solid was collected by filtration and dried at 30° C. in a vacuum oven for about 16 hours to provide a solid. The solid was determined to have similar physical properties as the N-2 form described above.

The crystalline forms of Example 1G were prepared and are tabulated as Examples 1G(a) and 1G(b) shown in Table 1 below. Said crystalline forms comprise crystals of forms N-1 and N-2. The forms of Example 1G were analyzed using one or more of the testing methods described hereinabove.

TABLE 1

| Example | Form | Solvents | Type |
|---------|------|----------|------|
| 1G(a) | N-1 | Butanol | Neat crystal |
| 1G(b) | N-2 | IPA/MeOH/Toluene/MTBE | Neat crystal |

Example 1G(a)

Single Crystal X-ray Measurements

Following the above Single Crystal Data procedure, the approximate unit cell dimensions in Angstroms (Å), as measured at a sample temperature of room temperature, as well as the crystalline cell volume (V), space group (sg), molecules per asymmetric unit, and crystal density for the N-1 form of Example 1G are shown below.

Cell Dimensions:
a=13.5209(3)
b=10.0154(2)
c=13.4607(3)
α=90
β=102.139(1)
γ=90
Space group: $P2_1/c$
Molecules/asymmetric unit (Z'): 1
Density, calc g-cm$^{-3}$: 1.358

The unit cell parameters were obtained from single crystal X-ray crystallographic analysis according to the procedure described in Stout et al., *X-Ray Structure Determination: A Practical Guide* (MacMillian, 1968), previously herein incorporated by reference.

Figure 4:
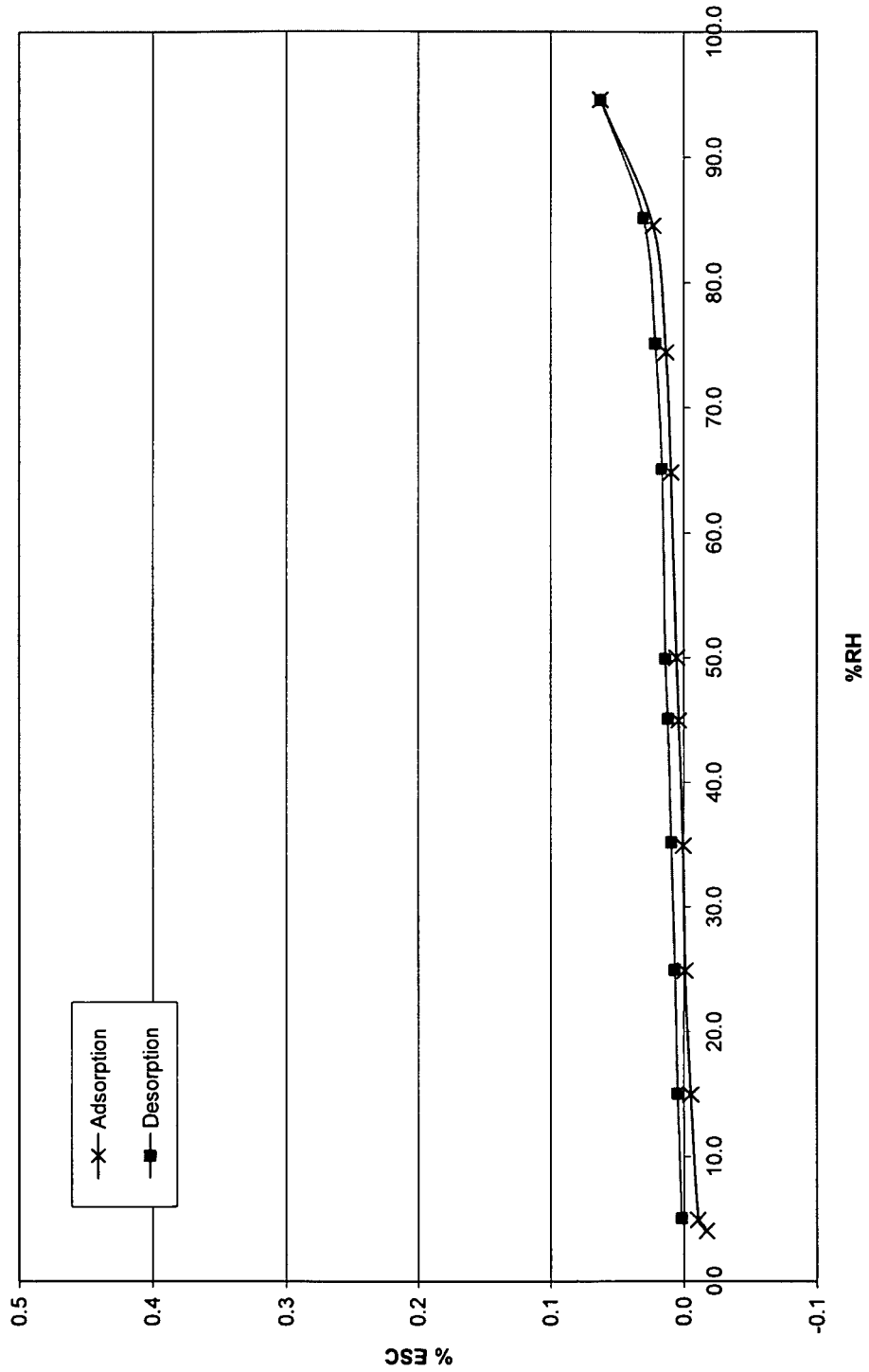
FIG. 4 shows a moisture sorption isotherm analysis of the N-1 crystalline form of a salt of a compound of Formula I.

A moisture sorption study indicates that the Form N-1 is non-hygroscopic in the range from about 25 to about 75% RH at 25° C. FIG. 4 shows a moisture sorption isotherm analysis of the N-1 crystalline form of Example 1G.

Powder X-ray Diffraction

X-ray powder diffraction (PXRD) data were obtained using the PXRD procedure described hereinabove. Table 2a and FIG. 1 show the PXRD data for the N-1 crystalline form for Example 1G.

TABLE 2a

Characteristic diffraction peak positions (degrees 2θ ± 0.1) @ RT, based on a high quality pattern collected with a diffractometer (CuKα) with a spinning capillary with 2θ calibrated with a NIST other suitable standard

| Peak No. | 2-Theta (°) |
|----------|-------------|
| 1 | 6.7 |
| 2 | 11.1 |
| 3 | 13.4 |
| 4 | 13.7 |
| 5 | 16.3 |
| 6 | 19.1 |
| 7 | 19.6 |
| 8 | 22.3 |
| 9 | 24.6 |

Differential Scanning Calorimetry (DSC)

Differential scanning calorimetry was conducted for each crystalline form using a TA Instruments™ model Q1000. For each analysis, the DSC cell/sample chamber was purged with 50 mL/min from above of ultra-high purity nitrogen gas. The instrument was calibrated with high purity indium. The heating rate was 10° C. per minute in the temperature range between 25 and 300° C. The heat flow, which was normalized by sample weight, was plotted versus the measured sample temperature. The data were reported in units of watts/gram ("W/g"). The plot was made with the endothermic peaks pointing down. FIG. 2 shows the DSC thermogram for the N-1 crystal form of Example 1G, which was observed to have an endothermic transition above ca. 150° C.

Thermogravimetric Analysis (TGA)

Thermogravimetric analysis was conducted using the procedure described above. FIG. 3 shows the TGA curve for the N-1 crystal form of Example 1G, which has a negligible weight loss up to about 100° C.

Example 1G(b)

Single Crystal X-ray Measurements

Following the above Single Crystal Data procedure, the approximate unit cell dimensions in Angstroms (Å), as measured at a sample temperature of room temperature, as well as the crystalline cell volume (V), space group (sg), molecules per asymmetric unit, and crystal density for the N-2 form of Example 1G are shown below.

Cell Dimensions:
    a=12.908(4)
    b=12.813(4)
    c=10.959(2)
    α=90
    β=90
    γ=90
    Space group: Pca2$_1$
    Molecules/asymmetric unit (Z'): 1
    Density, calc g-cm$^{-3}$: 1.335

The unit cell parameters were obtained from single crystal X-ray crystallographic analysis according to the procedure described in Stout et al., *X-Ray Structure Determination: A Practical Guide* (MacMillian, 1968), previously herein incorporated by reference.

Powder X-ray Diffraction

X-ray powder diffraction (PXRD) data were obtained using the PXRD procedure described hereinabove. Table 2b and FIG. 5 show the PXRD data for the N-2 crystalline form for Example 1G.

TABLE 2b

Characteristic diffraction peak positions (degrees 2θ ± 0.1) @ RT, based on a high quality pattern collected with a diffractometer (CuKα) with a spinning capillary with 2θ calibrated with a NIST other suitable standard

| Peak No. | 2-Theta (°) |
|---|---|
| 1 | 6.9 |
| 2 | 13.7 |
| 3 | 15.4 |
| 4 | 17.4 |
| 5 | 21.2 |
| 6 | 22.4 |
| 7 | 23.3 |

Differential Scanning Calorimetry (DSC)

Differential scanning calorimetry was conducted for each crystalline form using a TA Instruments™ model Q1000. For each analysis, the DSC cell/sample chamber was purged with 50 mL/min from above of ultra-high purity nitrogen gas. The instrument was calibrated with high purity indium. The heating rate was 10C per minute in the temperature range between 25 and 300° C. The heat flow, which was normalized by sample weight, was plotted versus the measured sample temperature. The data were reported in units of watts/gram ("W/g"). The plot was made with the endothermic peaks pointing down. FIG. 6 shows the DSC thermogram for the N-2 crystal form of Example 1G, which was observed to have an endothermic transition above ca. 150° C.

Thermogravimetric Analysis (TGA)

Thermogravimetric analysis was conducted using the procedure described above. FIG. 7 shows the TGA curve for the N-2 crystal form of Example 1G, which has a negligible weight loss up to about 100° C.

Example 1H 2-(3-(1-(4-Chlorophenyl)cyclopropyl)-[1,2,4]triazolo[4,3-a]pyridin-8-yl)propan-2-ol Bisulfate Salt

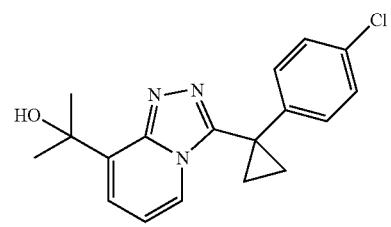

In order to affect dissolution, an aqueous sulfuric acid solution (~5:1 v/v) was added to a half-dram vial containing crude Example 1 at room temperature. A solid precipitated without agitation within a minute of the addition of the aqueous sulfuric acid solution. The resulting solid was collected by filtration to afford Example 1H as a white solid. The material was analyzed by one or more of the methods described above to be a crystalline material. The crystalline material was assigned the N-1 form.

Single Crystal X-ray Measurements

Following the above Single Crystal Data procedure, the approximate unit cell dimensions in Angstroms (Å), as measured at a sample temperature of room temperature, as well as the crystalline cell volume (V), space group (sg), molecules per asymmetric unit, and crystal density for the N-1 form of Example 1H are shown below.

Cell Dimensions:
    a=10.016(1)
    b=19.772(3)
    c=10.169(1)
    α=90
    β=103.454(7)
    γ=90
    Space group: P2$_1$/c
    Molecules/asymmetric unit (Z'): 1
    Density, calc g-cm$^{-3}$: 1.444

The unit cell parameters were obtained from single crystal X-ray crystallographic analysis according to the procedure described in Stout et al., *X-Ray Structure Determination: A Practical Guide* (MacMillian, 1968).

Powder X-Ray Diffraction

X-ray powder diffraction (PXRD) data were obtained using the PXRD procedure described hereinabove. FIG. 8 shows the PXRD data for the N-1 crystalline form for Example 1H.

Example 2

1-(3-(1-(4-Chlorophenyl)cyclopropyl)-[1,2,4]triazolo[4,3-a]pyridine-8-yl)cyclobutanol TFA Salt

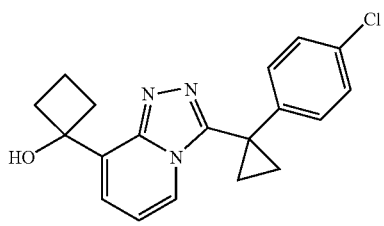

To a suspension of 1C (70 mg, 0.2 mmol) in 2 ml of THF at −10° C. was slowly added iso-propylmagnesium chloride lithium chloride complex (0.602 ml, 0.602 mmol). Upon completion of addition, the mixture was stirred at −10° C. (briefly warmed to 0° C.) for 1 h, and then cyclobutanone (70.4 mg, 1.0 mmol) was added quickly. The reaction mixture was stirred at −10° C. for 30 min, and then slowly warmed to rt where it was stirred for 3 h. After this time, the reaction mixture was quenched with water and extracted with EtOAc (3×5 ml). The combined organic layers were concentrated, and the crude product was purified via prep-HPLC (H$_2$O/CH$_3$CN/TFA, 20% to 100% B, 30×100 Luna column) to obtain Example 2 (15 mg, 16%) as an oil (TFA salt). LC/MS (m/z)=340 (M+H)+. HPLC Purity>95%.

Example 3

3-(1-(4-Chlorophenyl)cyclopropyl)-8-(prop-1-en-2-yl))-[1,2,4]triazolo[4,3-a]pyridine TFA Salt

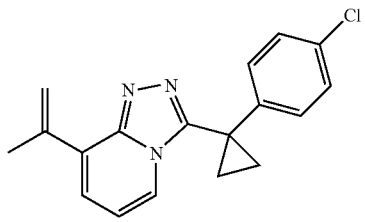

Argon was vigorously bubbled through a stirring mixture of compound 1C (0.070 g, 0.201 mmol), boronic ester 4,4,5,5-tetramethyl-2-(prop-1-en-2-yl)-1,3,2-dioxaborolane (0.038 mL, 0.201 mmol), and K$_3$PO$_4$ (0.107 g, 0.502 mmol) in THF (2 mL) for 5 min. After this time, PdCl$_2$(dppf)-CH$_2$Cl$_2$ (0.016 g, 0.020 mmol) was added. Upon completion of addition, the reaction vessel was flushed with argon, capped, and then heated to 90° C. for 20 h. At the conclusion of this period, the reaction mixture was cooled to rt and filtered to collect the crude product. The crude compound was purified by prep-HPLC (H$_2$O/CH$_3$CN/TFA, 20% to 100% B, 30×100 Luna column) to obtain Example 3 (30 mg, 48%) as an oil (TFA salt). LC/MS (m/z)=310 (M+H)+. HPLC Purity>95%.

Example 3B 3-(1-(4-Chlorophenyl)cyclopropyl)-8-(prop-1-en-2-yl))-[1,2,4]triazolo[4,3-a]pyridine

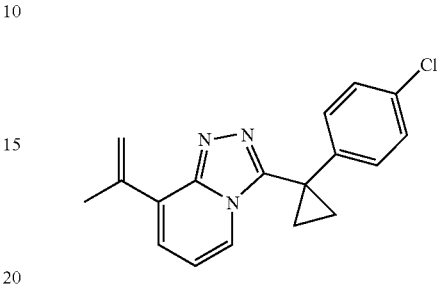

To a slurry of compound 1F (15.1 g; 43.6 mmoles; 1 equiv.) in toluene (135 mL) was added phosphoryl chloride (21 mL, 224 mmoles, 5.1 equiv.) over a 5 min period. Upon the completion of addition, the reaction mixture was heated to 95° C. where it was held for 22 hr. After this time, the reaction mixture was concentrated under vacuum distillation to a volume of ~45 mL. Acetonitrile (150 mL) was added to the residual solution. The resulting solution was concentrated by distillation at atmospheric pressure to a minimum volume and then acetonitrile (60 mL) was added to bring the final volume to ~105 mL. The resulting organic solution was cooled to ~5° C. and a solution of potassium carbonate (aq, 13.3 g, 95.3 mmoles, 2.2 equiv.) in water (260 mL) was added to provide a slurry. The slurry was warmed to ~20° C. where it stirred for 18 hr. At the conclusion of this period, the slurry was filtered. The filter cake was washed with water (75 mL) and dried in vacuo for ~3 hr to provide the crude product (12.1 g).

The crude product was added to a flask followed by toluene (50 mL). The resulting mixture was stirred for 20 min in order to achieve full dissolution. Upon full dissolution, a mixture of concentrated hydrochloric acid (4.3 mL, 50.1 mmoles, 1.2 equiv.) and isopropyl alcohol (15 mL) was added to the solution over a 15 min period. The resulting HCl salt slurry was stirred at ~20° C. for 18 hr. The resulting solid was collected by filtration, washed with toluene (25 mL), and then dried in vacuo for 3 hr to provide Example 3B as the HCl salt (11.2 g). The HCl salt was transferred to a flask and then acetonitrile (45 mL) and water (45 mL) were added. The resulting mixture was stirred for ~5 min in order to achieve full dissolution and then cooled to ~5° C. Once at the prescribed temperature, a solution of potassium carbonate (7 g, 50.1 mmoles, 1.2 equiv.) and water (90 mL) was added over a 15 min period. The resulting slurry was stirred for 30 min at room temperature. The resulting solid was collected by filtration, washed with water (60 mL) and then dried in vacuo at room temperature for 48 hr to provide Example 3B as the free base (9.5 g). The free base (9.5 g) was dissolved in acetonitrile (45 mL) at ~40° C. Upon completion of dissolution, the solution was cooled to ~20° C. and water (90 mL, 6 vols) was added. Upon completion of addition, the resulting slurry was stirred for ~3 hr. After this time, the resulting solid was collected by filtration, washed with water (45 mL) and then dried in vacuo at 70° C. for about 18 hours to provide recrystallized Example 3B (yield: 8.5 g, 63%. Purity, 99.61%, melting point 128.9° C.). IR (KBr) 3099, 3025, 1630, 1601, 1484, 1451, 1368, 1325, 1107, 1091, 1044, 1007, 924, 916, 749, 675, 531 cm$^{-1}$.

¹H NMR (400 MHz, CDCl₃): δ1.47-1.60 (m, 2H), 1.66-1.78 (m, 2H), 2.30 (s, 3H), 5.63 (br s, 1H), 6.75 (t,J=6.9 Hz, 1H), 6.78 (s, 1H), 7.18 (s, 1H), 7.16-7.27 (m, 3H), 6.99-7.10 (m, 2H), 7.74 (d,J=6.1, 1H). ¹³C NMR (100.6 MHz, CDCl₃): δ15.4, 19.8, 22.0, 113.6, 121.0, 121.4, 123.5, 127.6, 128.9, 129.9, 132.6, 137.3, 138.7, 148.4, 149.3. Mass $C_{18}H_{17}ClN_3$ (M+1): m/e, 310.13. Anal. Calcd for $C_{18}H_{16}ClN_3$: C, 69.79; H, 5.21; N, 13.56; Cl, 11.44. Found: C, 69.44; H, 5.02; N, 13.48, Cl, 11.45.

Example 4

3-(3-(1-(4-Chlorophenyl)cyclopropyl)-[1,2,4]triazolo[4,3-a]pyridine-8-yl) propan-1-ol

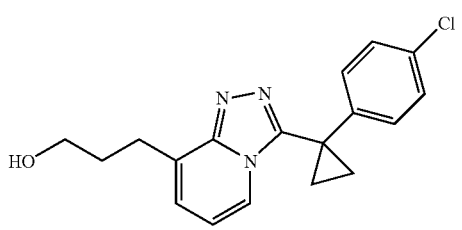

Compound 4A 8-(2-(1,3-Dioxan-2-yl)ethyl-3-(1-(4-chlorophenyl)cyclopropyl)-[1,2,4]triazolo[4,3-a]pyridine To a solution of zinc chloride (274 mg, 2.0 mmol) in THF (4 mL) was added (2-(1,3-dioxan-2-yl)ethyl)magnesium bromide (8.8 mL, 4.4 mmol, 0.5M THF) to provide bis(2-(1,3 dioxan-2-yl)ethyl)zinc. In a separate reaction vessel, a mixture of compound 1C (348.6 mg, 1.0 mmol) and potassium carbonate (276 mg, 2.0 mmol) in DMF (5 mL) was stirred at rt for 3 h. After this time, argon was bubbled through the mixture for 5 minutes and then the bis(2-(1,3 dioxan-2-yl) ethyl)zinc and Pd(dppf)Cl₂[CH₂Cl₂] (81.7 mg, 0.10 mmol) were added. Upon completion of addition, the reaction vessel was flushed with argon, capped, and then heated at 90° C. for 16 h. After this time, the reaction mixture was partitioned between diethyl ether and water and stirred vigorously for 15 minutes. The organic phase was separated, dried over Na₂SO₄ and concentrated in vacuo to yield a residue. The residue was purified via flash chromatography (SiO₂, 0-100% ethyl acetate/hexanes) followed by purification via preparative HPLC (Phenomenex Axia Luna column (30×100 mm); 0-100% B over 15 min, then 3 min B hold @ 40 mL/min; Solvent A=10% MeCN, 90% H₂O; Solvent B=90% MeCN, 10% H₂O) to afford compound 4A (289 mg, 75%) as a pale-yellow foam. LC/MS (m/z)=384 (M+H)+.

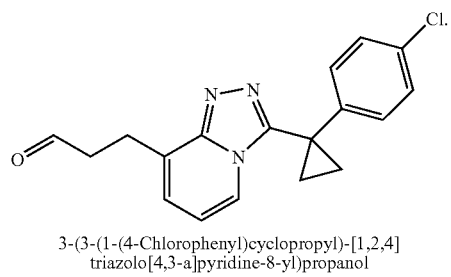

Compound 4B 3-(3-(1-(4-Chlorophenyl)cyclopropyl)-[1,2,4]triazolo[4,3-a]pyridine-8-yl)propanol To a solution of compound 4A (96.0 mg, 0.25 mmol) in acetone (2.5 mL) was added sulfuric acid (111 µL, 1.0 mmol, 9M). The resulting mixture was heated to reflux where it was stirred for 2 h. After this time, the reaction mixture was partitioned between ethyl acetate and 50% saturated aqueous sodium bicarbonate and then solid sodium chloride was added until the aqueous phase was saturated. The organic phase was separated, dried over Na₂SO₄, and concentrated in vacuo to yield a residue. The residue was purified via flash chromatography (SiO₂, 0-100% ethyl acetate/hexanes) to provide compound 4B (95.6 mg, 73%) as an off-white foam.

Example 4

To a 0° C. solution of compound 4B (32.6 mg, 0.1 mmol) in THF (1 mL) was added sodium borohydride (3.9 mg, 0.1 mmol) in one portion. Upon completion of addition, the reaction mixture was stirred for 1 h. After this time, a 50% saturated aqueous ammonium chloride (1 mL) was added and the resulting mixture was stirred vigorously for 1 h. At the conclusion of this period, ethyl acetate (2 mL) was added, and the organic layer was separated, dried over Na₂SO₄, and then concentrated in vacuo to yield a residue. The residue was purified via preparative HPLC (Phenomenex Axia Luna column (30×100 mm); 0-100% B over 15 min, then 3 min B hold @ 40 mL/min; Solvent A=10% MeCN, 90% H₂O with 0.1% TFA; Solvent B=90% MeCN, 10% H₂O with 0.1% TFA), and the desired fractions were collected, washed with saturated aqueous NaHCO₃ and then concentrated to afford Example 4 (9.5 mg, 29%) as a pale-yellow foam. LC/MS (m/z)=328 (M+H)+. HPLC Purity>95%.

Example 5

Methyl 2-(3-(1-(4-chlorophenyl)cyclobutyl)-[1,2,4]triazolo[4,3-a]pyridine-8-yl)-2-methylpropanoate

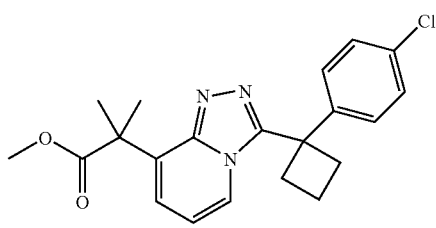

To a crimp-top microwave vial was added 8-bromo-3-(1-(4-chlorophenyl)cyclobutyl)-[1,2,4]triazolo[4,3-a]pyridine (50 mg, 0.14 mmol) (prepared in a manner similar to Example 1), ZnF₂ (7.2 mg, 0.069 mmol), and Pd(dba)₂ (7.9 mg, 0.014 mmol). The vial was flushed with argon, and then P(tBu)₃ (28 μL, 1.0 M, 0.028 mmol), (1-methoxy-2-methylprop-1-enyloxy)trimethylsilane (36 mg, 0.207 mmol), and DMF (1mL) were added. The vial was capped and heated at 80° C. for 16 h. After this time, the reaction mixture was cooled to room temperature and partitioned between ethyl acetate/Et₂O (1:1) and water. The organic phase was separated, dried over Na₂SO₄, and concentrated in vacuo to yield a residue. The residue was purified by prep HPLC (Phenomenex Axia Luna column (30×100 mm); 50-70% B over 15 min, then 3 min B hold @ 40 mL/min; Solvent A=10% MeOH, 90% H₂O, 0.1% TFA; Solvent B=90% MeOH, 10% H₂O, 0.1% TFA). The fractions containing product were neutralized via passage (gravity) through a bicarbonate cartridge (PolymerLabs, PL-HCO₃ MP-Resin, 0.36 mmol, one cartridge per 18mL tube) and then concentrated to provide Example 5 (16 mg, 30%) as a white foam. LC/MS (/z)=384 (M+H)+. HPLC Purity>95%.

Example 6

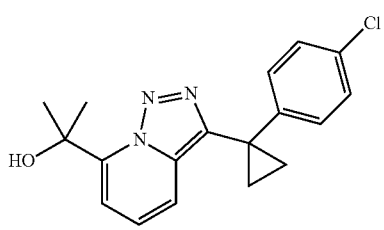

Compound 6A

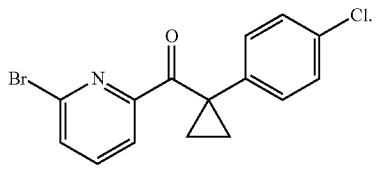

(6-Bromopyridin-2-yl)(1-(4-chlorophenyl)cyclopropyl)-methanone

To a dry 250 mL round bottom flask was added 15 mL of THF and 2.5 M n-BuLi (8.4 mL, 21.1 mmol). The flask was cooled to −78° C. and to it was added a solution of 2,6-dibromopyridine (5 g, 21.1 mmol) in 40 mL of THF, dropwise via addition funnel, under nitrogen atmosphere. Upon completion of addition, the mixture was stirred for an additional 15 min at −78° C. To the resulting dark green solution at −78° C. was added 1-(4-chlorophenyl)cyclopropanecarbonitrile (4.5 g, 25.3 mmol) over 1 min. The reaction mixture was then allowed to warm to room temperature and to it was added 6N HCl (27.5 mL, 165 mmol) and the reaction mixture was heated to reflux for 10 min, followed by stirring at room temperature for 1.5 h. The solution was then made basic by addition of 1N NaOH at 0° C. The organic layer was separated and the aqueous layer was extracted with EtOAc (3×50 mL). The combined organic layers were dried (MgSO₄) and concentrated in vacuo to yield 8.7 g of crude material as an orange oil, which was purified by flash chromatography over 330 g of silica gel (eluted with Hexanes:EtOAc 95:5) to give compound 6A (3.3 g, 47% yield) as a white solid. ¹H NMR: δ 7.62 (d,J=8 Hz, 1H), 7.47 (t,J=8 Hz, 1H), 7.37 (d,J=8 Hz, 1H), 7.24 (d,J=8 Hz, 2H), 7.13 (d,J=8 Hz, 2H), 1.79-1.76 (m, 2H), 1.30-1.28 (m, 2H). LC/MS (m/z)=338 (M+H)⁺.

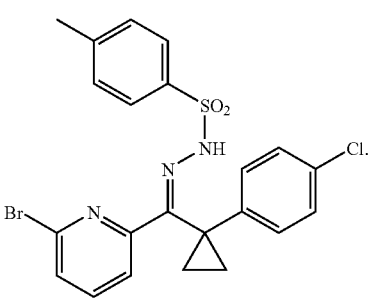

Compound 6B (E)-N'-((6-Bromopyridin-2-yl)(1-(4-chlorophenyl)cyclopropyl)methylene)-4-methylbenzenesulfonohydrazide To a 25 mL round bottom flask was added compound 6A (0.12 g, 0.36 mmol), p-toluenesulfonhydrazide (0.07 g, 0.36 mmol) and 0.7 mL of methanol. The reaction mixture was stirred at 65° C. for 6 h, cooled to room temperature, and the solid was isolated by vacuum filtration to afford compound 6B (0. 13 g, 71% yield) as a white powder. ¹H NMR: δ 13.34 (s, 1H), 7.90 (d,J=8 Hz, 2H), 7.51-7.50 (m, 2H), 7.42-7.40 (m, 1H), 7.31 (d,J=8 Hz, 2H), 7.08 (d,J=9 Hz, 2H), 6.90 (d,J=9, 2H), 2.43 (s, 3H), 1.36 (dd,J=2, 7 Hz, 2H), 1.22 (dd,J=2, 7, 2H). LC/MS (m/z)=506 (M+H)⁺.

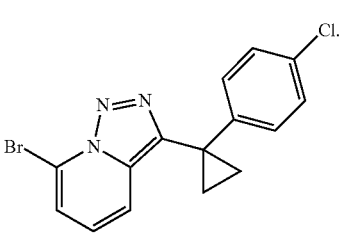

Compound 6C

7-Bromo-3-(1-(4-chlorophenyl)cyclopropyl)-[1,2,3]triazolo[1,5-a]pyridine

To a solution of compound 6B (0.68 g, 1.3 mmol) in 13 mL of dichloromethane was added iodobenzene diacetate (0.65 g, 2.0 mmol) at room temperature. The reaction mixture was stirred at room temperature for 45 min. After this time, the solvent was removed in vacuo, 3 mL of methanol was added and the resulting solid was isolated by vacuum filtration to yield compound 6C (125 mg, 27% yield) as an off-white solid. ¹H NMR: δ 7.28 (s, 4H), 7.16 (dd,J=1, 7 Hz, 1H), 7.05 (dd, 1, 9 Hz, 1H), 6.94 (dd,J=2, 7 Hz, 1H), 1.70 (dd,J=2, 7 Hz, 2H), 1.43 (dd,J=3, 7 Hz, 2H). LC/MS (m/z)=350 (M+H)⁺.

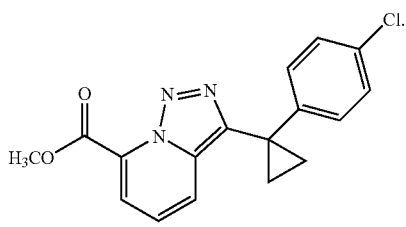

Compound 6D

Methyl 3-(1-(4-chlorophenyl)cyclopropyl)-[1,2,3]triazolo[1,5-a]pyridine-7-carboxylate To a 50 mL pressure vessel was added compound 6C (50 mg, 0.14 mmol), 1,3-bis(diphenylphosphino)propane (11.8 mg, 0.03 mmol), palladium(II) acetate (6.4 mg, 0.03 mmol), 4 mL of methanol and triethylamine (0.06 mL, 0.43 mmol). The vessel was sealed, bubbled with CO for 5 min, and then pressurized to 25 PSI with CO. The reaction mixture was stirred at 50° C. for 17 h under 25 PSI of CO. The mixture was cooled to room temperature, diluted with methanol, filtered through a pad of Celite and concentrated in vacuo. The residue was partitioned between 20 mL of EtOAc and 10 mL of brine. The organic layer was washed with (2×5 mL) water, dried over $MgSO_4$ and concentrated in vacuo to yield a residue. The residue was dissolved in acetonitrile, filtered and purified by reverse phase HPLC (Phen Luna 5u C18 column, 30 min gradient from 20%-100% B. A=$H_2O$/$CH_3CN$/TFA 90:10:0.1. B=$CH_3CN$/$H_2O$/TFA 90:10:0.1), with a flow rate of 20 mL/min. The desired fractions were concentrated in vacuo to yield compound 6D (32.2 mg, 68% yield) as a bright yellow solid. $^1$H NMR (methanol-d3): δ 7.75 (d,J=7 Hz, 1H), 7.54 (d,J=9 Hz, 1H), 7.25-7.18(m,5H),3.96(s, 3H), 1.51 (dd, J=2, 7 Hz, 2H), 1.39(dd, J=3, 7 Hz, 2H). LC/MS (m/z)=328 (M+H)$^+$.

Example 6

To a solution of compound 6D (0.03 g, 0.09 mmol) in 2 mL of THF was added methylmagnesium chloride (0.09 mL, 0.28 mmol) dropwise over a period of 2 min, under nitrogen atmosphere. The reaction mixture was stirred at room temperature for 1 h. After this time, the reaction mixture was quenched with 4 mL of saturated aqueous sodium chloride, the organic layer was separated, and the aqueous layer was extracted (3×5 mL) EtOAc. The combined organic layers were dried over $MgSO_4$ and concentrated in vacuo to give the crude alcohol as an off-white solid. The solid was dissolved in methanol, filtered and purified by reverse phase HPLC (Phen Luna 5u C18 column, 30 min gradient from 20%-100% B. A=$H_2O$/$CH_3CN$ 90:10. B=$CH_3CN$/$H_2O$ 90:10) with a flow rate of 30 mL/min. The desired fractions were concentrated in vacuo to yield Example 6 (17.2 mg, 57% yield) as a white solid. $^1$HNMR: δ 7.24-7.19 (m, 4H), 7.02-6.98 (m, 2H), 6.80 (dd,J=2, 7 Hz, 1H), 1.75 (s, 6H), 1.60 (dd,J=3, 7 Hz, 2H), 1.36 (dd,J=2, 7 Hz, 2H). The carbinol hydroxyl proton is not observed in the $^1$H NMR. LC/MS (m/z)=328/330 (M+H)$^+$.

Examples 7 to 16

Examples 7 to 16 in Table 3 were synthesized according to the procedures described above, or by other similar methods known to one skilled in the art, with other appropriate reagents.

TABLE 3

| Example | Structure | LC/MS (ES+, M + H) | HPLC purity (%) |
| --- | --- | --- | --- |
| 7 | 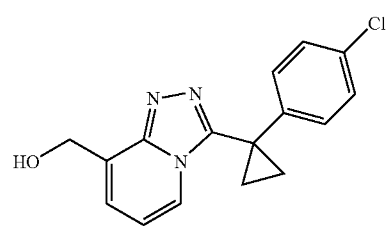 | 300 | >95 |
| 8 | 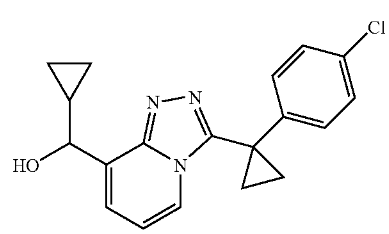 | 340 | >95 |
| 9 | 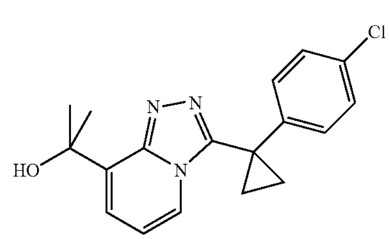 | 356 | >95 |

TABLE 3-continued

| Example | Structure | LC/MS (ES+, M + H) | HPLC purity (%) |
|---|---|---|---|
| 10 | 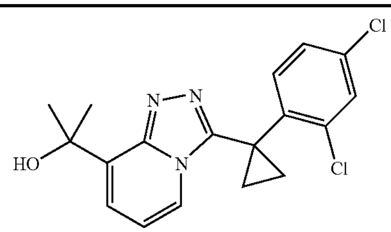 | 362 | >95 |
| 11 | 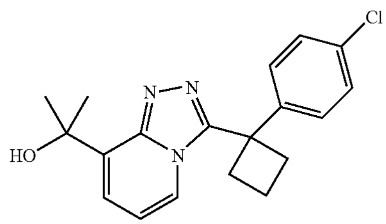 | 342 | >95 |
| 12 | 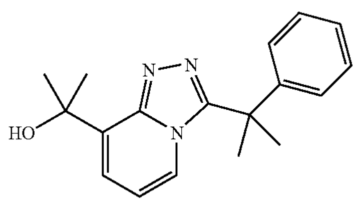 | 296 | >95 |
| 13 | 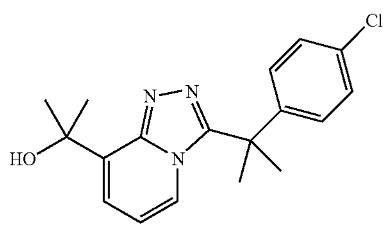 | 330 | >95 |
| 14 | 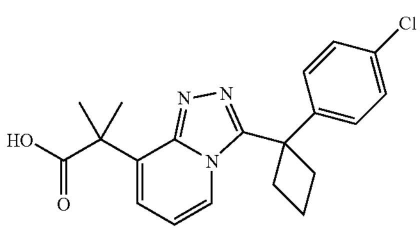 | 370 | >95 |
| 15 | 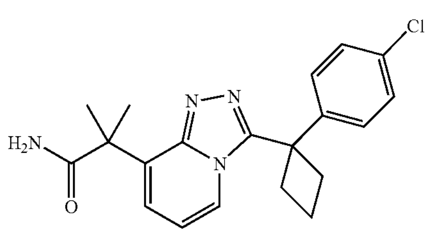 | 369 | >95 |
| 16 | 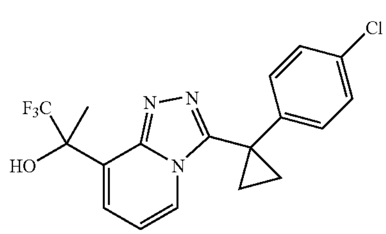 | 382 | >95 |

Example 17

2-(3-(4-(3-(4-Fluorophenyl)-1,2,4-oxadiazol-5-yl)bicyclo[2.2.2]octan-1-yl)-[1,2,4]triazolo[4,3-a]pyridin-8-yl)propan-2-ol

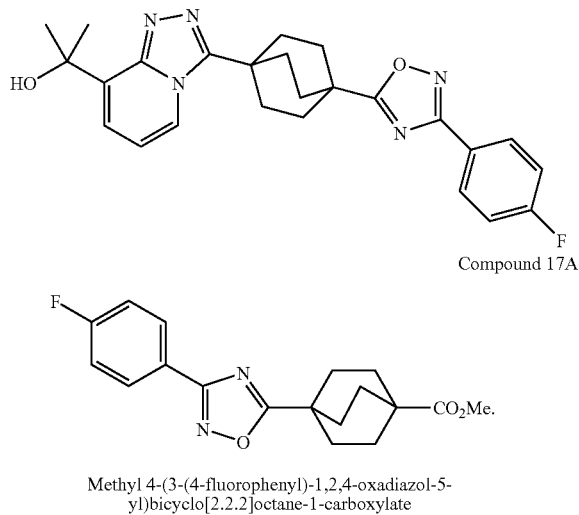

Compound 17A

Methyl 4-(3-(4-fluorophenyl)-1,2,4-oxadiazol-5-yl)bicyclo[2.2.2]octane-1-carboxylate To a suspension of 4-(methoxycarbonyl)bicyclo[2.2.2]octane-1-carboxylic acid (3.9 g, 18.2 mmol) in 60 mL of dichloromethane was added N,N'-carbonyldiimidazole (4.4 g, 27.3 mmol) at room temperature. The reaction mixture was stirred at room temperature for 1 h, then 4-fluoro-N'-hydroxybenzimidamide (5.0 g, 32.4 mmol) was added, followed by stirring at room temperature for 8 h. After this time, the mixture was concentrated in vacuo, diluted in 40 mL of toluene and stirred at reflux for 16 h. After this time, the reaction mixture was cooled to room temperature, diluted with 100 mL of ethyl acetate and washed with 30 mL of brine. The organic layer was separated, dried over MgSO$_4$ and concentrated in vacuo. The resulting crude material was purified by flash chromatography over 330 g of silica gel (elution with 0-20% ethyl acetate in hexanes) to afford compound 17A (3.0 g, 9.1 mmol, 50%) as a white solid. LCMS (m/z)=331 (M+H)$^+$.

Compound 17B

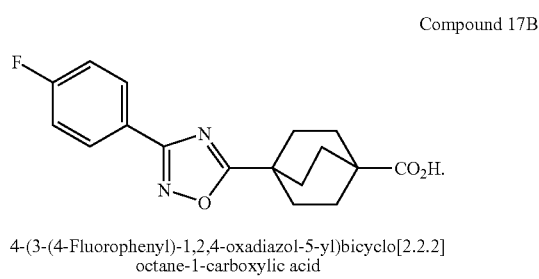

4-(3-(4-Fluorophenyl)-1,2,4-oxadiazol-5-yl)bicyclo[2.2.2]octane-1-carboxylic acid To a suspension of compound 17A (3.0 g, 9.1 mmol) in 7 mL of methanol was added 4M aqueous LiOH (2.4 mL, 9.6 mmol) at room temperature. Upon completion of addition, the reaction mixture was stirred heated to 65° C. where it stirred for 3 h. At the conclusion of this period, the reaction mixture was cooled to room temperature and then concentrated in vacuo. The resulting aqueous residue was partitioned between ethyl acetate and water. The pH was adjusted to 1 by addition of concentrated. HCl. The organic layer was separated and the aqueous layer was extracted (3×15 mL) with ethyl acetate. The combined organic layers were dried over Na$_2$SO$_4$ and concentrated in vacuo to give compound 17B (2.8 g, 8.9 mmol, 97%) as a white solid. LCMS (m/z)=315 (M−H)$^−$.

Compound 17C

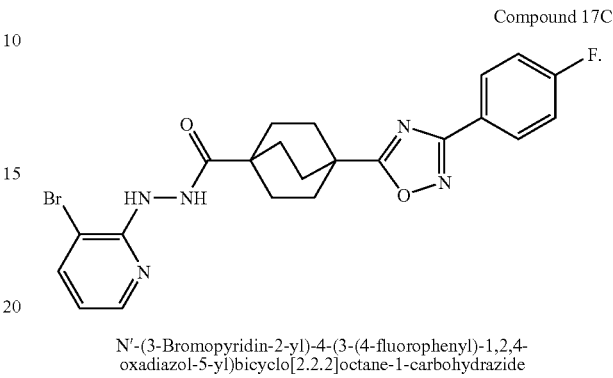

N'-(3-Bromopyridin-2-yl)-4-(3-(4-fluorophenyl)-1,2,4-oxadiazol-5-yl)bicyclo[2.2.2]octane-1-carbohydrazide To a solution of compound 17B (1.0 g, 3.2 mmol) in 25 mL of dry tetrahydrofuran was added NMM (0.65 mL, 5.9 mmol) at room temperature. Upon completion of addition, the solution was cooled to 0° C. and ethyl carbonochloridate (0.38 mL, 3.95 mmol) was added dropwise. The resulting mixture was stirred at 0° C. for 30 min, and then 3-bromo-2-hydrazinylpyridine (compound 1A, 1.49 g, 3.95 mmol) was added in one portion. The reaction mixture was stirred at 0° C. for 30 min, and then at room temperature for 2.5 h. After this time, the reaction mixture was quenched with water. The organic layer was separated, dried over MgSO$_4$ and concentrated in vacuo. The resulting crude residue was purified by flash chromatography over 120 g of silica gel (gradient elution with 0-40% ethyl acetate in hexanes) to give compound 17C (0.73 g, 1.5 mmol, 47%) as a white solid. LCMS (m/z)=488 (M+H)$^+$.

Compound 17D

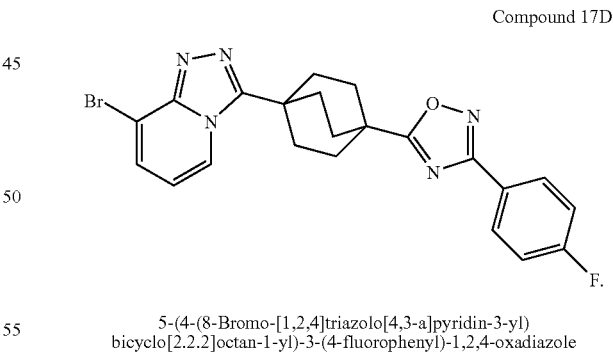

5-(4-(8-Bromo-[1,2,4]triazolo[4,3-a]pyridin-3-yl)bicyclo[2.2.2]octan-1-yl)-3-(4-fluorophenyl)-1,2,4-oxadiazole To a solution of compound 17C (0.73 g, 1.5 mmol) in 22 mL of a 2.7:1 mixture of tetrahydrofuran and carbon tetrachloride, cooled to 0° C., was added DIEA (2.1 mL, 12.0 mmol) followed by dropwise addition of triethylphosphine (0.67 mL, 4.5 mmol). The resulting bright yellow suspension was stirred at 0° C. for 1.5 h, at which point HPLC indicated that the starting material had been consumed. The reaction mixture was then quenched with water, and the organic layer was separated, dried over MgSO$_4$ and was concentrated in vacuo to yield the crude material. The crude material was taken up in 5 mL of methanol, and the resulting solid was isolated by vacuum filtration and then washed with cold methanol to yield compound 7D (0.48 g, 1.02 mmol, 68%) as a yellow solid. LCMS (m/z)=470 (M+H)+.

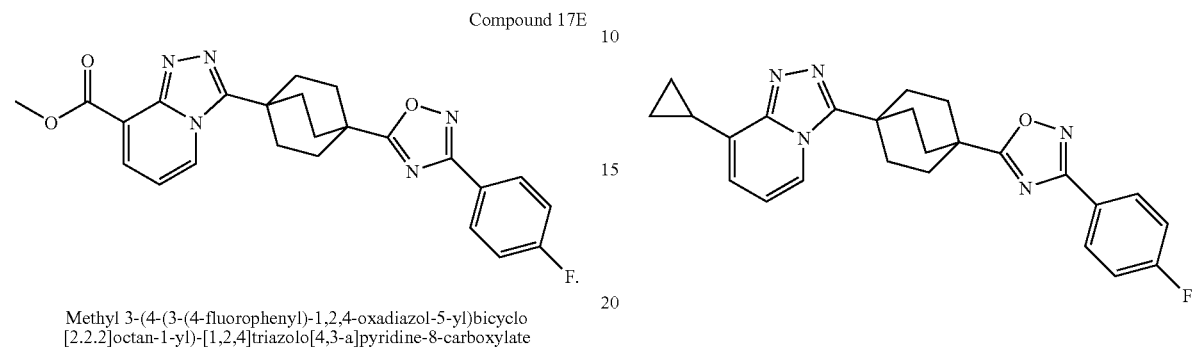

Compound 17E

Methyl 3-(4-(3-(4-fluorophenyl)-1,2,4-oxadiazol-5-yl)bicyclo [2.2.2]octan-1-yl)-[1,2,4]triazolo[4,3-a]pyridine-8-carboxylate To a pressure vessel was added compound 17D (0.4 g, 0.85 mmol), 17 mL of methanol, 1,3-bis(diphenylphosphino)propane (0.07 g, 0. 17 mmol), palladium(II) acetate (0.038 g, 0.17 mmol) and triethylamine (0.36 mL, 2. 6 mmol). The pressure vessel was evacuated and then charged with 25 PSI of CO at room temperature. The reaction mixture was then heated to 60° C. where it stirred for 18 h. After this time, the reaction mixture was cooled to room temperature. Once at the prescribed temperature, the reaction mixture was diluted with methanol, filtered through a pad of Celite and concentrated in vacuo to yield a residue. The residue was partitioned between 100 mL of ethyl acetate and 50 mL of brine. The organic layer was washed (2×25 mL) with water, dried over MgSO4 and concentrated in vacuo to yield the crude product. The crude product was purified by flash chromatography over 40 g of silica gel (gradient elution with 0-100% ethyl acetate in hexanes) to provide compound 17E (0.35 g, 0.79 mmol, 93%) as a white solid. LCMS (m/z)=448 (M+H)+.

Example 17

To a solution of Compound 17E (100 mg, 0.22 mmol) in 4.5 mL of tetrahydrofuran was added dropwise a 3M THF solution of methylmagnesium chloride (447 µL, 1.34 mmol) at room temperature. Upon completion of addition, the reaction mixture was stirred at room temperature for 2 h, and then an additional 6 eq of methylmagnesium chloride was added. After 30 min, the reaction mixture was analyzed by HPLC, which showed that the ketone had been consumed. The reaction mixture was then quenched with 10 mL of saturated aqueous sodium chloride, 10 mL of saturated aqueous ammonium chloride and then ethyl acetate was added until two clear phases emerged. The organic layer was separated and the aqueous layer was extracted (3×10 mL) with ethyl acetate. The combined organic layers were dried over MgSO4 and concentrated in vacuo to yield the crude material. The crude material was purified by flash chromatography over 40 g of silica gel (elution with 0-100% ethyl acetate in hexanes) to yield Example 17 (50 mg, 0.11 mmol, 50%) as a white solid. LCMS (m/z)=470 (M+H)+. LCMS (m/z)=448 (M+H)+.

Example 18

5-(4-(8-Cyclopropyl-[1,2,4]triazolo[4,3-a]pyridin-3-yl)bicyclo[2.2.2]octan-1-yl)-3-(4-fluorophenyl)-1,2,4-oxadiazole To a 10 mL microwave vial was added compound 17D (40 mg, 0.085 mmol), cyclopropylboronic acid (14.7 mg, 0. 17 mmol), potassium phosphate (54.4 mg, 0.26 mmol), palladium (II) acetate (0.71 mg, 3.16 µmol), tricyclohexylphosphine (1.8 mg, 6.41 µmol), 739 µL toluene and 37 µL of water. Upon completion of addition, the vial was flushed with nitrogen, sealed and heated to 100° C. where it stirred for 18 h and then cooled to room temperature. Once at the prescribed temperature, the mixture was diluted with 5 mL of methanol, filtered through a pad of Celite and concentrated in vacuo. The resulting residue was dissolved in 10 mL of chloroform, washed with two 3 mL portions of water, dried over MgSO4 and concentrated in vacuo to yield a residue. This residue was dissolved in acetonitrile, filtered and purified by reverse phase HPLC (Phen AXIA Luna 75×30 mm 5u column, 10 min gradient from 20-100% B. A=H2O/CH3CN/TFA 90:10:0.1. B=CH3CN/H2O/TFA 90:10:0.1, with a flow rate of 30 mL/min). The desired fractions were collected and concentrated in vacuo with excess sodium bicarbonate until the water remained. The aqueous layer was extracted with chloroform, and the combined organic layers were dried over MgSO4 and concentrated in vacuo to give Example 18 (20.0 mg, 0.046 mmol, 53%) as a white solid. LCMS (m/z)=430 (M+H)+.

Example 19

2-(3-(1-(4-Chlorophenyl)cyclobutyl)-[1,2,4]triazolo [4,3-a]pyridin-8-yl)propan-2-amine, TFA Salt

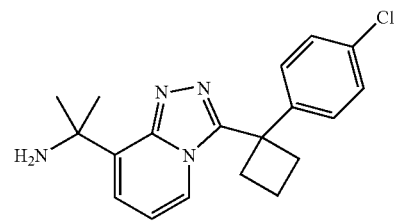

Compound 19A

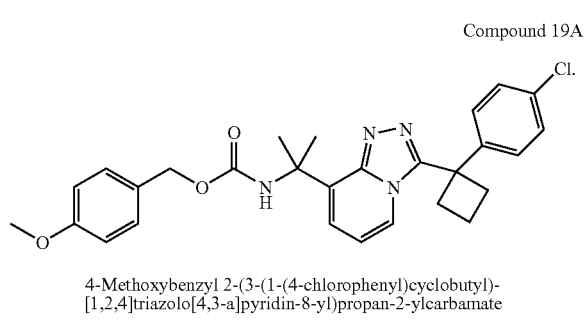

4-Methoxybenzyl 2-(3-(1-(4-chlorophenyl)cyclobutyl)-
[1,2,4]triazolo[4,3-a]pyridin-8-yl)propan-2-ylcarbamate To a solution of Example 14 (120 mg, 0.32 mmol) in dichloromethane (3.2 mL) was added dropwise 1-chloro-N,N,2-trimethylprop-1-en-1-amine (52 μL, 0.39 mmol) during a 1 minute period. Upon completion of addition the reaction mixture was stirred for 1 h and then it was concentrated in vacuo. The resulting residue was dissolved in acetone (810 μL) and then a solution of sodium azide (32 mg, 0.49 mmol) in water (810 μL) was added dropwise during a 1 minute period. Upon completion of addition, the reaction mixture was stirred for 1 h. After this time, the reaction mixture was partitioned between diethyl ether and water and stirred vigorously for 15 minutes. At the conclusion of this period, the organic phase was separated, dried over sodium sulfate, and concentrated in vacuo. The resulting residue was dissolved in toluene (3.24 mL) and heated to reflux where it stirred for 16 h. After this time, the reaction mixture was cooled to room temperature. Once at the prescribed temperature, a solution of 4-methoxybenzyl alcohol (81 μL, 0.65 mmol) in toluene (300 μL) was added, and the resulting solution was heated to reflux where it stirred for 18 h. At the conclusion of this period, the reaction mixture was concentrated in vacuo and the resulting residue was purified via flash chromatography (SiO₂, 0-100% ethyl acetate/hexanes) to afford compound 19A (115 mg, 71%) as a white foam. LC/MS (m/z)=505 (M+H)⁺.

Example 19

To a solution of compound 19A (100 mg, 0.198 mmol) in dichloromethane (990 μL) was added trifluoroacetic acid (990 μL). Upon completion of addition the reaction mixture was stirred for 30 minutes and then carefully poured in to excess 50% saturated aqueous sodium bicarbonate. The resulting mixture was stirred until all the acid was neutralized. The organic phase was separated, dried over sodium sulfate, and concentrated in vacuo. The resulting residue was purified via preparative HPLC (Phenomenex Axia Luna column (30×75 mm); 0-100% B over 15 min, then 3 min B hold @ 40 mL/min; Solvent A=10% MeCN, 90% H₂O with 0.1% TFA; Solvent B=90% MeCN, 10% H₂O with 0.1% TFA.) to provide Example 19 (78.2 mg, 82%) as a white foam (TFA salt). LC/MS (m/z)=341 (M+H)⁺. HPLC Purity>95%.

Example 20

8-(2-(1H-Tetrazol-5-yl)propan-2-yl)-3-(1-(4-chlorophenyl)cyclobutyl)-[1,2,4]triazolo[4,3-a]pyridine

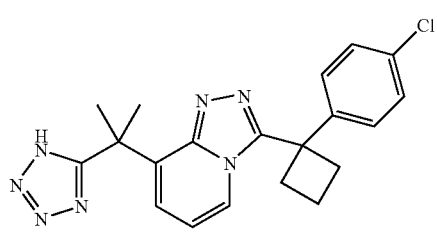

Compound 20A 2-(3-(1-(4-Chlorophenyl)cyclobutyl)-[1,2,4]triazolo
[4,3-a]pyridin-8-yl)-N-(2-cyanoethyl)-2-methylpropanamide To a solution of Example 14 (102 mg, 0.276 mmol) in dichloromethane (2.8 mL) was added dropwise 1-chloro-N,N,2-trimethylprop-1-en-1-amine (44 μL, 0.331 mmol) during a 1 minute period. Upon completion of addition, the reaction mixture was stirred for 90 minutes. At the conclusion of this period, the reaction mixture was cooled to 0° C. and then 3-aminopropanenitrile (122 μL, 1.65 mmol) was added dropwise during a 1 minute period. The resulting mixture was stirred for 30 minutes and then the cooling bath was removed. The mixture was stirred for 16 h and then loaded onto a silica gel column and purified via flash chromatography (SiO₂, 0-30% [25% methanol/75% ethyl acetate]/hexanes, then re-purified on SiO₂ eluting with 0-100% ethyl acetate/hexanes) to afford compound 20A (87 mg, 70%) as a colorless viscous oil. LC/MS (m/z)=422 (M+H)⁺.

Compound 20B

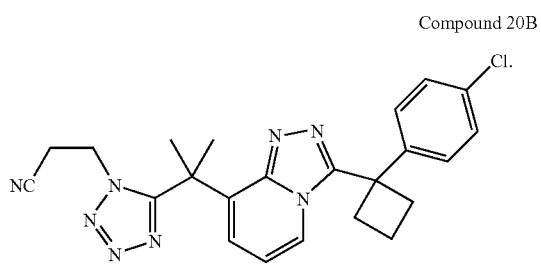

3-(5-(2-(3-(1-(4-Chlorophenyl)cyclobutyl)-[1,2,4]triazolo
[4,3-a]pyridin-8-yl)propan-2-yl)-1H-tetrazol-1-yl)propanenitrile To a solution of compound 20A (30 mg, 0.071 mmol) in dichloromethane (700 μL) was added pyridine (35 μL, 0.427 mmol), and phosphorous pentachloride (22 mg, 0.107 mmol). The resulting mixture was heated to reflux where it stirred for 2h. After this time, the reaction mixture was cooled to room temperature and azidotrimethylsilane (14 μL, 0.107 mmol) was added. Upon completion of addition, the resulting mixture was stirred for 16 h. At the conclusion of this period, more azidotrimethylsilane (14 μL, 0.107 mmol) was added and the reaction mixture was stirred for an additional 2h. At the conclusion of this period, the reaction mixture was loaded onto a silica gel column and purified via flash chromatography (SiO$_2$, 0-60% ethyl acetate/hexanes) to provide compound 20B (20 mg, 62%) as a colorless viscous oil. LC/MS (m/z)=447 (M+H)$^+$.

Example 20

To a solution of compound 20B (16 mg, 0.36 mmol) in THF/MeOH (180 μL/180 μL) was added aqueous sodium hydroxide (72 μL, 0.072 mmol, 1.0M). The resulting mixture stirred vigorously for 16 h. After this time, the pH of the reaction mixture was adjusted to 3-4 with 1M aqueous HCl and resulting mixture was extracted with ethyl acetate. The combined extracts were dried over sodium sulfate, and concentrated in vacuo. The resulting residue was purified via flash chromatography (SiO$_2$, 0-60% [25% methanol/75% ethyl acetate]/hexanes) to furnish Example 20 (11 mg, 77%) as a white solid. LC/MS (m/z)=394 (M+H)$^+$.

Example 21

3-(1-(4-Bromophenyl)cyclopropyl)-8-(2-((2-(trimethylsilyl)ethoxy)methoxy)propan-2-yl)-[1,2,4]triazolo[4,3-a]pyridine

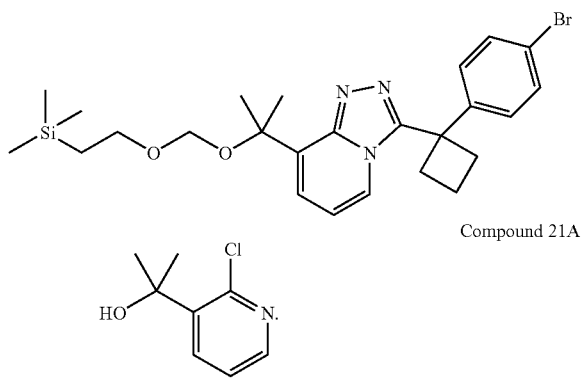

Compound 21A

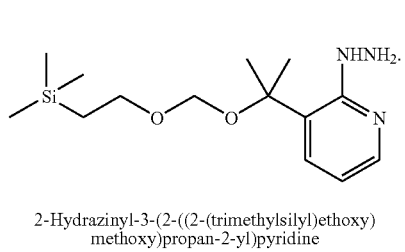

2-(2-Chloropyridin-3-yl)propan-2-ol

To a solution of methyl 2-chloronicotinate (10.0 g, 58.3 mmol) in THF (233 mL) was added a solution of methylmagnesium chloride (58.3 mL, 175 mmol, 3.0M) during a 3 min period, which produced an exotherm to 50° C. Upon completion of addition, the reaction mixture was stirred for 30 minutes. After this time, the reaction mixture was carefully quenched with 50% saturated aqueous ammonium chloride, and then partitioned between diethyl ether and excess 50% saturated aqueous ammonium chloride. The resulting mixture was stirred vigorously for 30 minutes. The organic layer was separated, dried over sodium sulfate, and concentrated in vacuo. The resulting oil was purified via flash chromatography (SiO$_2$, 0-100% ethyl acetate/hexanes) to afford compound 21A (8.36 g, 84%) as a colorless viscous oil. LC/MS (m/z)=172 (M+H)$^+$.

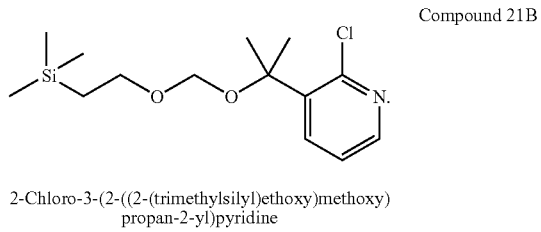

Compound 21B

2-Chloro-3-(2-((2-(trimethylsilyl)ethoxy)methoxy)propan-2-yl)pyridine

To a solution of compound 21A (4.0 g, 23.3 mmol), Hunig's base (16.3 mL, 93.0 mmol), and tetrabutylammoniun iodide (18.9 g, 51.3 mmol) in dichloromethane (46.6 mL) was added (2-(chloromethoxy)ethyl)trimethylsilane (8.2 mL, 46.6 mmol). The resulting mixture was heated to reflux where it stirred for 22 h. At the conclusion of this period, the reaction mixture was loaded onto a silica gel column and purified via flash chromatography (SiO$_2$, 0-30% ethyl acetate/hexanes) to provide compound 21B (5.34 g, 76%) as a colorless oil. LC/MS (m/z)=302 (M+H)$^+$.

Compound 21C

2-Hydrazinyl-3-(2-((2-(trimethylsilyl)ethoxy)methoxy)propan-2-yl)pyridine

To a solution of compound 21B (4.2 g, 13.9 mmol) in pyridine (13.5 mL) was added hydrazine (4.37 mL, 139 mmol). The resulting mixture was heated to 100° C. where it stirred for 5 days. After this time, the reaction mixture was concentrated in vacuo. The resulting oil was purified via flash chromatography (SiO$_2$, 0-100% ethyl acetate/hexanes) to provide compound 21C (3.35 g, 81%) as a pale-yellow oil. LC/MS (m/z)=298 (M+H)$^+$.

Example 21

To a 0° C. solution of 1-(4-bromophenyl)cyclopropanecarboxylic acid (810 mg, 3.36 mmol) and N-methylmorpholine (407 μL, 3.70 mmol) in THF (13.5 mL) was added dropwise isobutyl chloroformate (464 μL, 3.53 mmol) during a 2 minute periods. Upon completion of addition, the mixture was stirred for 2 h and then a solution of compound 21C (1.00 g, 3.36mmol) in THF (20 mL) was added during a 4 min period. Upon completion of addition, the reaction mixture was stirred for 1 h. After this time, the reaction mixture was partitioned between ethyl acetate and water. The organic phase was separated, dried over sodium sulfate, and concentrated in vacuo. The resulting residue was dissolved in THF (20 mL) and carbontetrachloride (13.5 mL) and then cooled to 0° C. Once at the prescribed temperature, Hunig's base (4.40 mL, 25.2 mmol) was added, followed by the dropwise addition of triethylphosphine (1.24 mL, 8.40 mmol). The resulting mixture was stirred for 30 minutes and then an additional triethylphosphine (600 μL) was added. Upon completion of addition, the reaction mixture was stirred for an additional 30 minutes. At the conclusion of this period, the reaction mixture was carefully quenched with water, and then partitioned between ethyl acetate and water. The organic phase was separated, dried over sodium sulfate, and concentrated in vacuo. The resulting oil was purified via flash chromatography (SiO₂, 0-100% ethyl acetate/hexanes) to afford Example 21 (1.16 g, 69%) as a pale-yellow viscous oil. LC/MS (m/z)=502 (M+H)⁺.

Example 22

2-(3-(1-(4-(1H-Tetrazol-5-yl)phenyl)cyclobutyl)-[1,2,4]triazolo[4,3-a]pyridin-8-yl)propan-2-ol

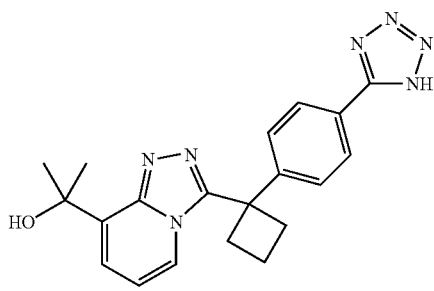

Compound 22A

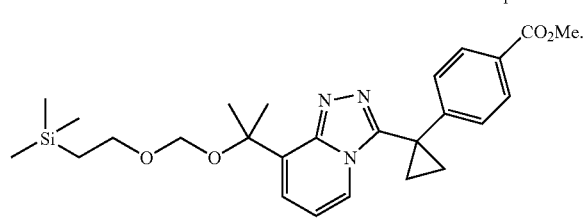

Methyl 4-(1-(8-(2-((2-(trimethylsilyl)ethoxy)methoxy)propan-2-yl)-[1,2,4]triazolo[4,3-a]pyridin-3-yl)cyclopropyl)benzoate Compound 22A was prepared from Example 21 in a manner similar as the procedure for compound 1D set forth above. LC/MS (m/z)=482 (M+H)⁺.

Compound 22B

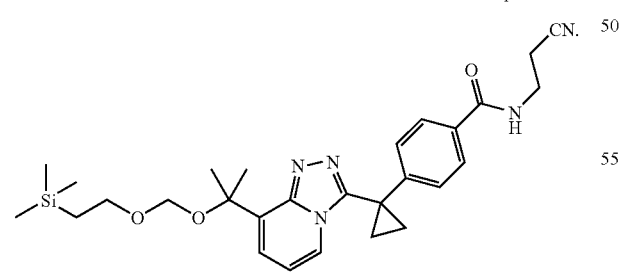

N-(2-Cyanoethyl)-4-(1-(8-(2-((2-(trimethylsilyl)ethoxy)methoxy)propan-2-yl)-[1,2,4]triazolo[4,3-a]pyridin-3-yl)cyclopropyl)benzamide Compound 22B was prepared from compound 22A in a manner similar as the procedure for compound 20A set forth above. LC/MS (m/z)=520 (M+H)⁺.

Compound 22C

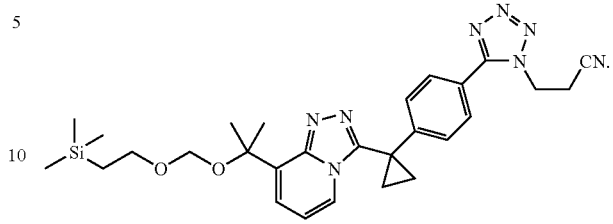

3-(5-(4-(1-(8-(2-((2-(Trimethylsilyl)ethoxy)methoxy)propan-2-yl)-[1,2,4]triazolo[4,3-a]pyridin-3-yl)cyclopropyl)phenyl)-1H-tetrazol-1-yl)propanenitrile To a solution of compound 22B (82 mg, 0.158 mmol), triphenylphosphine (50 mg, 0.190 mmol), and azidotrimethylsilane (25 µL, 0.190 mmol) in a solution of dichloromethane (1.6 mL) was added dropwise diethylazodicarboxylate (30 µL, 0.190 mmol) during a 1 minute period. Upon completion of addition, the mixture was stirred for 16 h. After this time, additional triphenylphosphine (50 mg, 0.190 mmol), azidotrimethylsilane (25 µL, 0.190 mmol) and diethylazodicarboxylate (30 µL, 0.190 mmol) were added. The reaction mixture was stirred for 2 h and then loaded onto a silica gel column and purified via flash chromatography (SiO₂, 0-60% ethyl acetate/hexanes) to provide compound 22C (53 mg, 61%) as a white foam. LC/MS (m/z)=545 (M+H)⁺.

Compound 22D

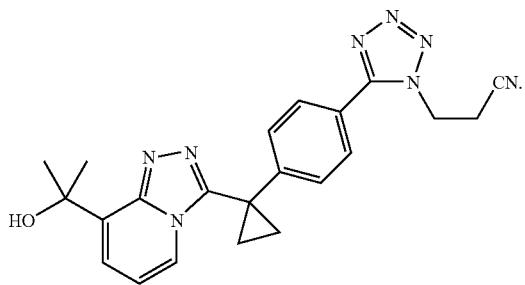

3-(5-(4-(1-(8-(2-Hydroxypropan-2-yl)-[1,2,4]triazolo[4,3-a]pyridin-3-yl)cyclopropyl)phenyl)-1H-tetrazol-1-yl)propanenitrile To a 0° C. solution of compound 22C (50 mg, 0.092 mmol) in dichloromethane (920 µL) was added trifluoroacetic acid (920 µL). Upon completion of addition, the reaction mixture was stirred for 1 h and then carefully poured in to excess 50% saturated aqueous sodium bicarbonate. The resulting mixture was stirred until all the acid was neutralized. The organic phase was separated, dried over sodium sulfate, and concentrated in vacuo. The resulting residue was purified via flash chromatography (SiO₂, 0-100% [25% methanol/75% ethyl acetate]/hexanes) to furnish compound 22D (35 mg, 93%) as a white foam. LC/MS (m/z)=415 (M+H)⁺.

Example 22

Example 22 was prepared from compound 22D in a manner similar to the procedure for Example 20 set forth above. LC/MS (m/z)=362 (M+H)+. HPLC Purity=>99%.

Example 23

2-(3-(1-(1-Benzyl-1H-tetrazol-5-yl)cyclopropyl)-[1,2,4]triazolo[4,3-a]pyridin-8-yl)propan-2-ol

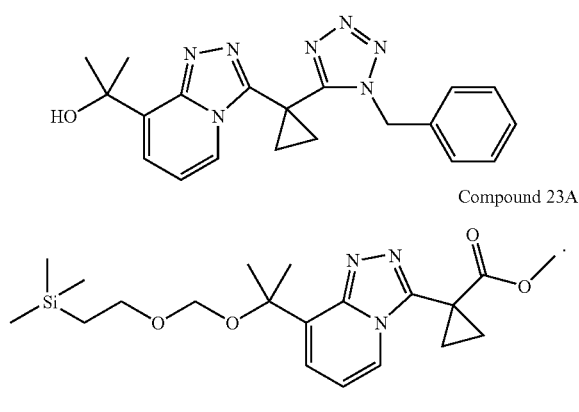

Compound 23A

Methyl 1-(8-(2-((2-(trimethylsilyl)ethoxy)methoxy)propan-2-yl)-[1,2,4]triazolo[4,3-a]pyridin-3-yl)cyclopropanecarboxylate Compound 23A was prepared in a manner similar to the procedure for Example 21 set forth above. LC/MS (m/z)=406 (M+H)+.

Compound 23B

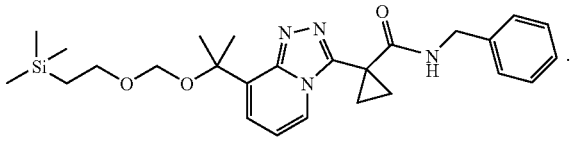

N-Benzyl-1-(8-(2-((2-(trimethylsilyl)ethoxy)methoxy)propan-2-yl-[1,2,4]triazolo[4,3-a]pyridin-3-yl)cyclopropanecarboxamide Compound 23B was prepared in a manner similar to the procedure for compound 20A set forth above. LC/MS (m/z)=481 (M+H)+.

Compound 23C

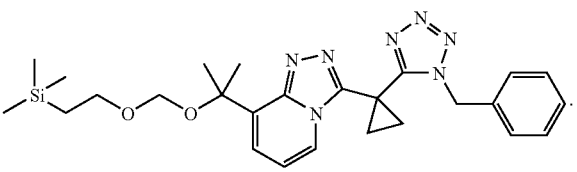

3-(1-(1-Benzyl-1H-tetrazol-5-yl)cyclopropyl)-8-(2-((2-(trimethylsilyl)ethoxy)methoxy)propan-2-yl)-[1,2,4]triazolo[4,3-a]pyridine Compound 23C was prepared from compound 23B in a manner similar to the procedure for compound 20B set forth above. LC/MS (m/z)=506 (M+H)+.

Example 23

Example 23 was prepared from compound 23C in a manner similar to the procedure for Example 20 set forth above. LC/MS (m/z)=376 (M+H)+. HPLC Purity=>99%.

Example 24

2-(3-(1-(4-Phenylthiazol-2-yl)cyclopropyl)-[1,2,4]triazolo[4,3-a]pyridin-8-yl)propan-2-ol

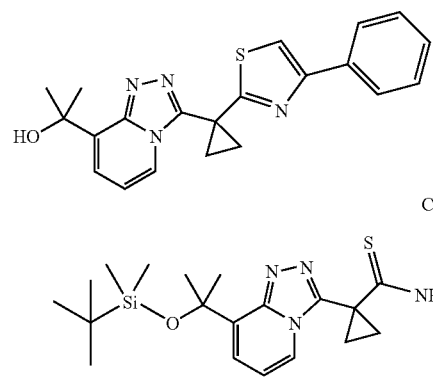

Compound 24A 1-(8-(2-(tert-Butyldimethylsilyloxy)propan-2-yl)-[1,2,4]triazolo[4,3,-a]pyridin-3-yl)cyclopropanecarbothioamide To a solution of 1-(8-(2-(tert-butyldimethylsilyloxy)propan-2-yl)-[1,2,4]triazolo[4,3-a]pyridin-3-yl)cyclopropanecarboxamide (170 mg, 0.454 mmol) (prepared in a manner similar to the procedure for compound 23B set forth above) in dichloromethane (2.3 mL) was a added solution of Lawesson's reagent (367 mg, 0.908 mmol) in dichloromethane (2.3 mL). Upon completion of addition, the mixture was stirred for 3 days. After this time, more Lawesson's reagent (180 mg) was added and the reaction mixture was stirred for an additional 24 h. At the conclusion of this period, the reaction mixture was carefully quenched with 25% saturated aqueous sodium bicarbonate, and then excess 25% saturated aqueous sodium bicarbonate and dichloromethane were added. The resulting mixture was stirred vigorously for 30 min, which produced a thick emulsion. After the emulsion had dissipated, the organic layer was separated, dried over brine and then sodium sulfate, and then concentrated in vacuo. The resulting residue was purified via flash chromatography (SiO$_2$, 0-30% [25% methanol/75% ethyl acetate]/hexanes) to afford compound 24A (142 mg, 80%) as a pale-yellow solid. LC/MS (m/z)=391 (M+H)+.

Example 24

To a solution of compound 24A (20 mg, 0.051 mmol) in THF (510 μL) was added 2-bromo-1-phenylethanone (20 mg, 0.102 mmol). Upon completion of addition, the reaction mixture was stirred for 16 h. At the conclusion of this period, the reaction mixture was partitioned between ethyl acetate and 50% saturated aqueous sodium bicarbonate. The resulting mixture stirred vigorously for 15 min. The organic layer was separated, dried over sodium sulfate, and then concentrated in vacuo. The resulting residue was dissolved in THF (510 μL), and a solution of tetrabutylammonium fluoride (153 μL, 0.153 mmol, 1.0M) was added. Upon completion of addition, the resulting mixture was heated to reflux where it stirred for 1 h. After this time, the reaction mixture was cooled to room temperature and then partitioned between ethyl acetate and 50% saturated aqueous ammonium chloride. The resulting mixture was stirred vigorously for 15 min. The organic layer was separated, dried over brine and then sodium sulfate, and concentrated in vacuo. The resulting residue was purified via flash chromatography (SiO$_2$, 0-60% [25% methanol/75% ethyl acetate]/hexanes) to afford Example 24 (4.9 mg, 25%) as a an off-white foam. LC/MS (m/z)=377 (M+H)$^+$. HPLC Purity>99%.

Examples 25 to 119

Examples 25 to 119 in Table 4 were synthesized according to the procedures described above, or by other similar methods known to one skilled in the art, with other appropriate reagents.

TABLE 4

| Example | Structure | LC/MS (ES+, M + H) | HPLC purity (%) |
|---|---|---|---|
| 25 | 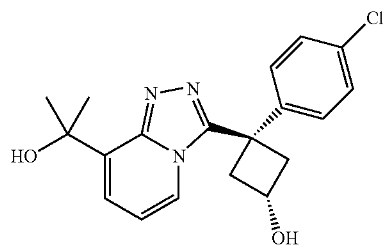 | 358 | >95 |
| 26 | 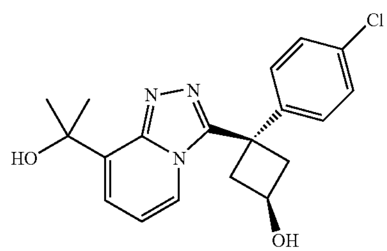 | 358 | >95 |
| 27 | 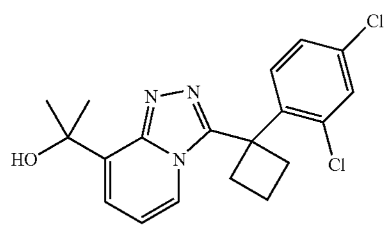 | 376 | >95 |
| 28 | 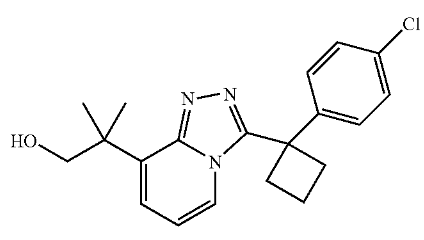 | 356 | >95 |
| 29 | 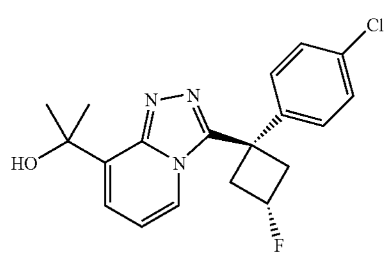 | 360 | >95 |

TABLE 4-continued

| Example | Structure | LC/MS (ES+, M + H) | HPLC purity (%) |
|---|---|---|---|
| 30 | 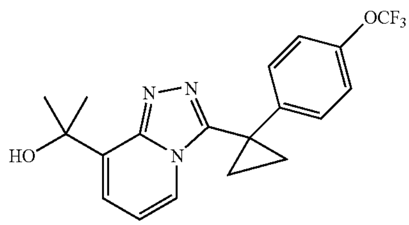 | 378 | >95 |
| 31 | 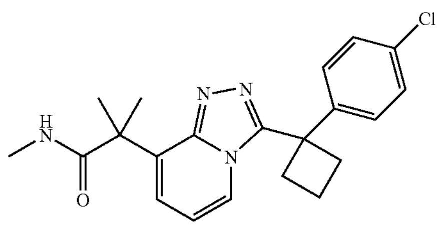 | 383 | >95 |
| 32 | 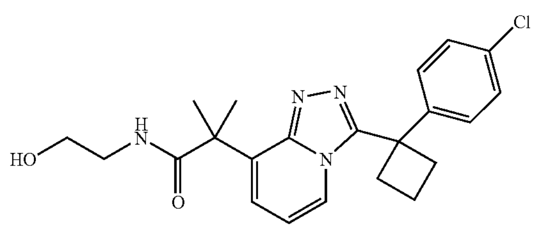 | 413 | >95 |
| 33 | 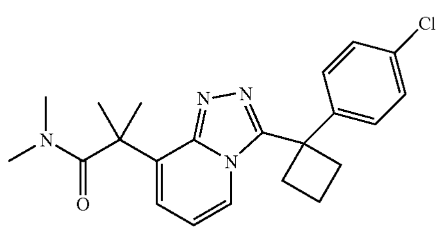 | 397 | >95 |
| 34 | 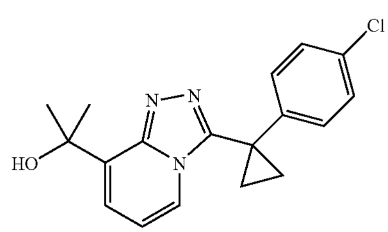 | 362 | >95 |
| 35 | 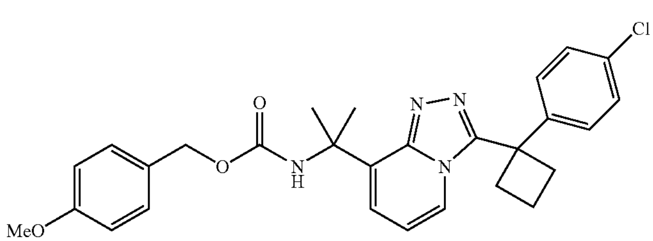 | 505 | >95 |

TABLE 4-continued

| Example | Structure | LC/MS (ES+, M + H) | HPLC purity (%) |
|---|---|---|---|
| 36 | 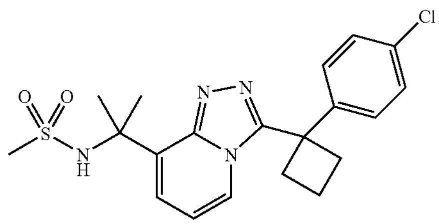 | 419 | >95 |
| 37 | 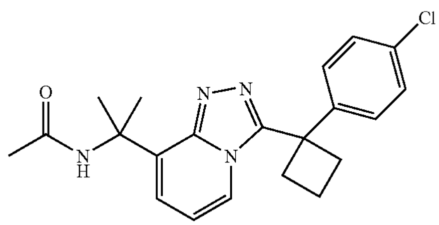 | 383 | >95 |
| 38 | 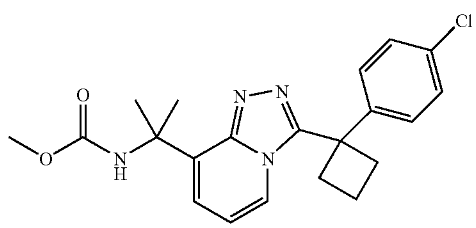 | 399 | >95 |
| 39 | 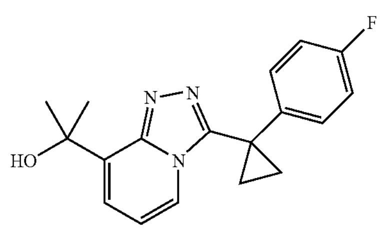 | 312 | >95 |
| 40 | 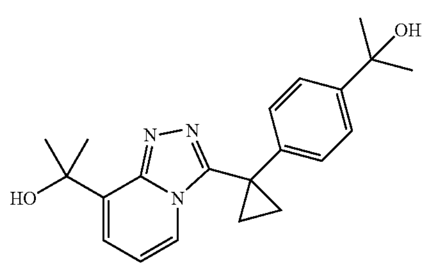 | 352 | >95 |
| 41 | 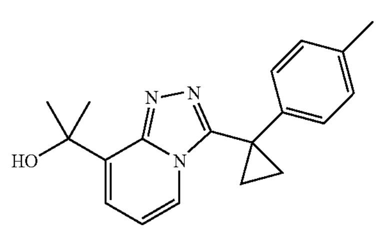 | 308 | >95 |

TABLE 4-continued

| Example | Structure | LC/MS (ES+, M + H) | HPLC purity (%) |
|---------|-----------|---------------------|-----------------|
| 42 | 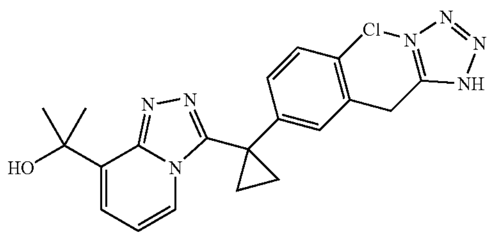 | 410 | >95 |
| 43 | 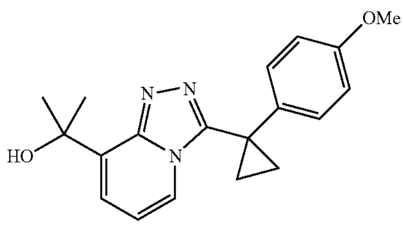 | 324 | >95 |
| 44 | 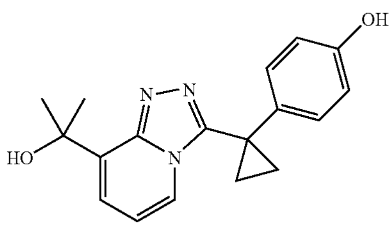 | 310 | >95 |
| 45 | 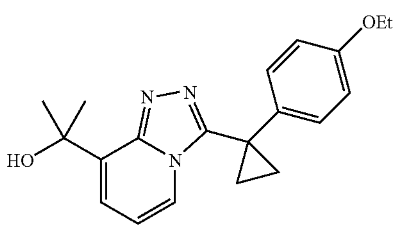 | 338 | >95 |
| 46 | 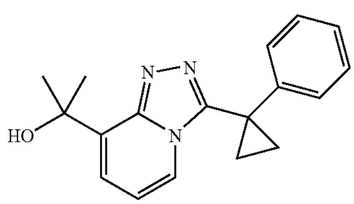 | 294 | >95 |
| 47 | 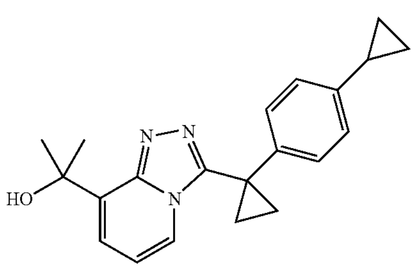 | 334 | >95 |

TABLE 4-continued

| Example | Structure | LC/MS (ES+, M + H) | HPLC purity (%) |
|---|---|---|---|
| 48 | 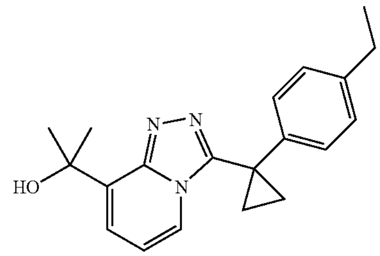 | 322 | >95 |
| 49 | 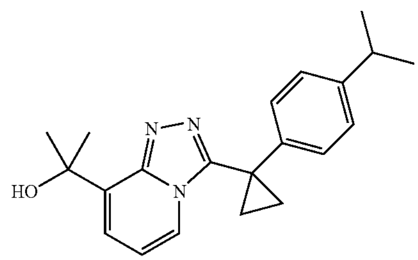 | 336 | >95 |
| 50 | 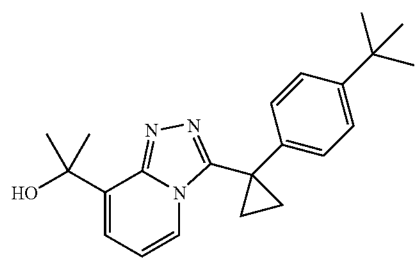 | 350 | >95 |
| 51 | 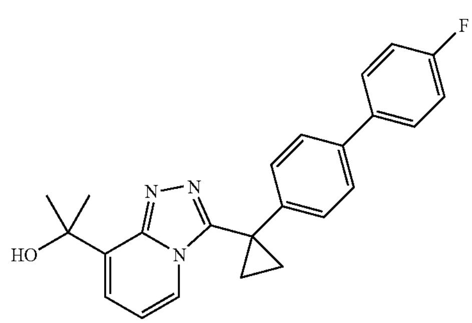 | 388 | >95 |
| 52 | 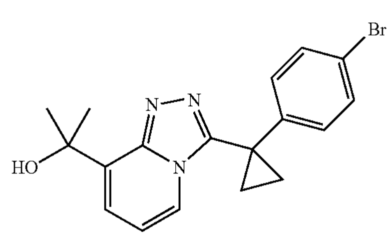 | 372 | >95 |

TABLE 4-continued

| Example | Structure | LC/MS (ES+, M + H) | HPLC purity (%) |
|---|---|---|---|
| 53 | 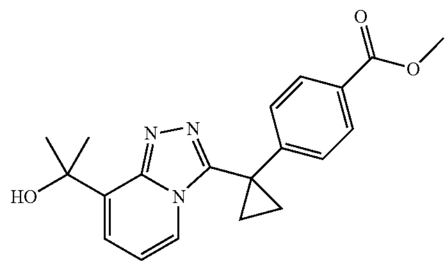 | 352 | >95 |
| 54 | 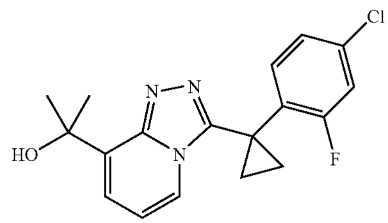 | 346 | >95 |
| 55 | 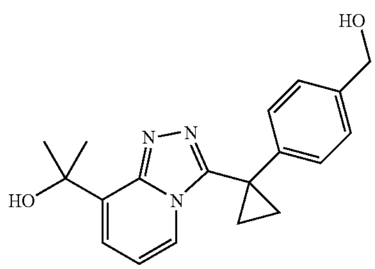 | 324 | >95 |
| 56 | 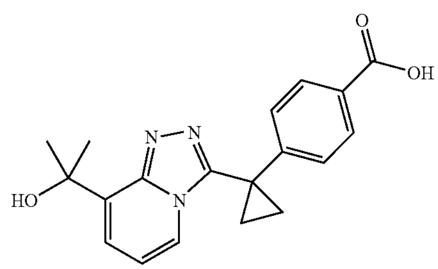 | 338 | >95 |
| 57 | 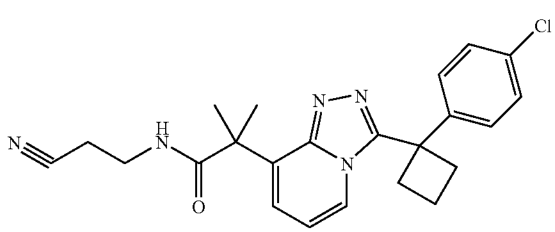 | 422 | >95 |
| 58 | 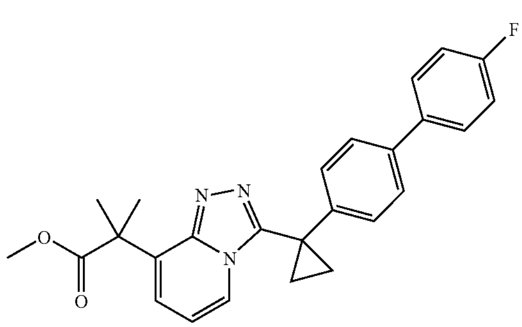 | 430 | >95 |

TABLE 4-continued

| Example | Structure | LC/MS (ES+, M + H) | HPLC purity (%) |
|---------|-----------|---------------------|------------------|
| 59 | 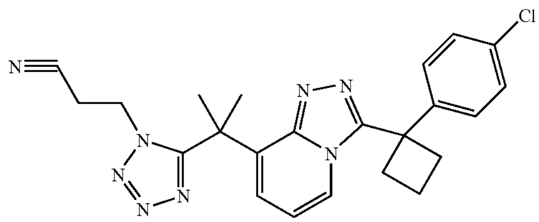 | 447 | >95 |
| 60 | 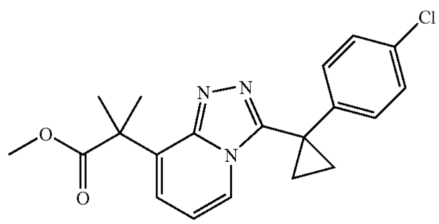 | 370 | >95 |
| 61 | 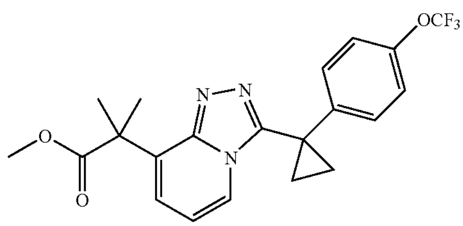 | 420 | >95 |
| 62 | 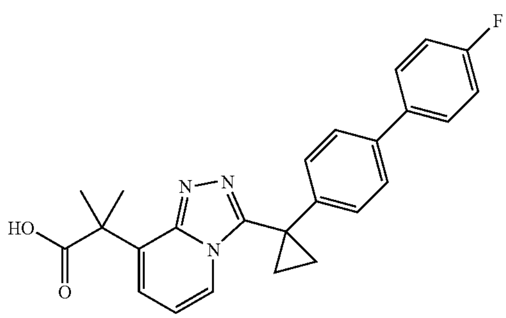 | 416 | >95 |
| 63 | 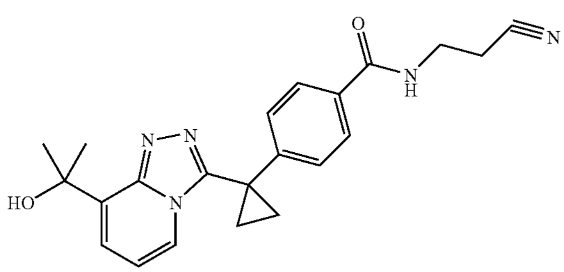 | 390 | >95 |
| 64 | 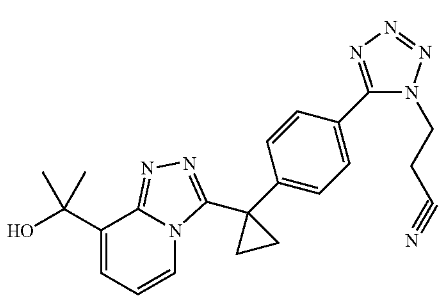 | 415 | >95 |

TABLE 4-continued

| Example | Structure | LC/MS (ES+, M + H) | HPLC purity (%) |
|---|---|---|---|
| 65 | 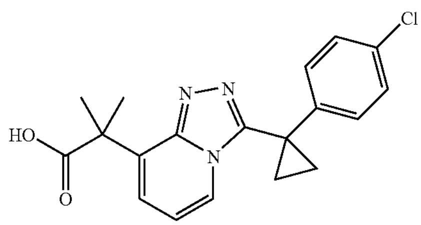 | 356 | >95 |
| 66 | 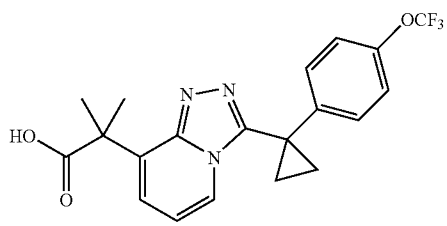 | 406 | >95 |
| 67 | 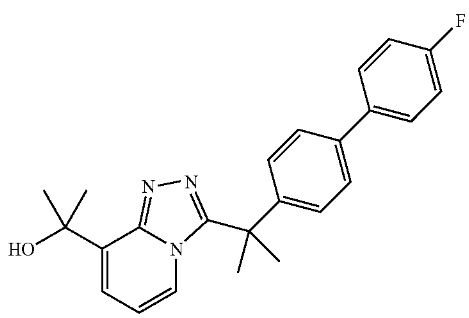 | 390 | >95 |
| 68 | 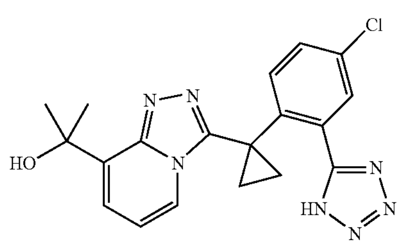 | 396 | >95 |
| 69 | 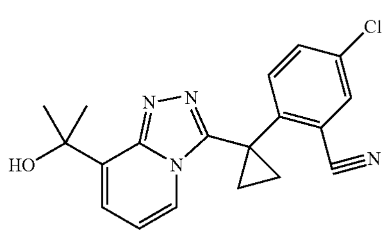 | 353 | >95 |
| 70 | 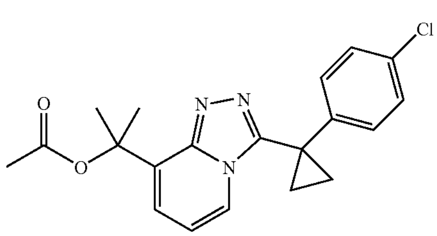 | 370 | >95 |

TABLE 4-continued

| Example | Structure | LC/MS (ES+, M + H) | HPLC purity (%) |
|---|---|---|---|
| 71 | 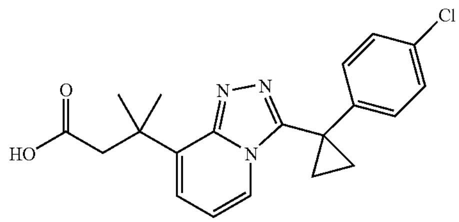 | 370 | >95 |
| 72 | 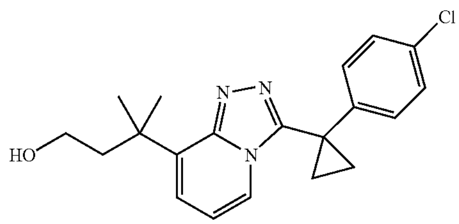 | 356 | >95 |
| 73 | 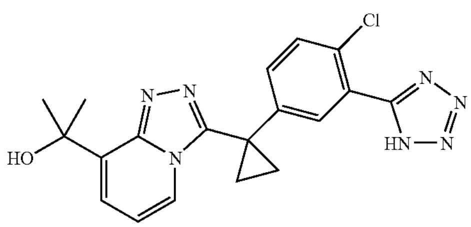 | 396 | >95 |
| 74 | 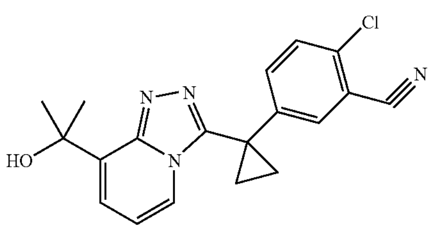 | 353 | >95 |
| 75 | 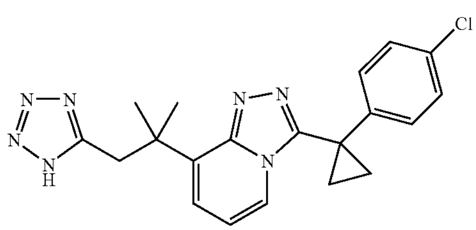 | 394 | >95 |
| 76 | 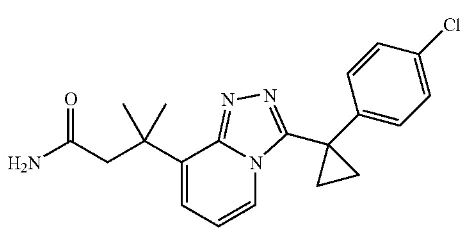 | 369 | >95 |

TABLE 4-continued

| Example | Structure | LC/MS (ES+, M + H) | HPLC purity (%) |
|---|---|---|---|
| 77 | 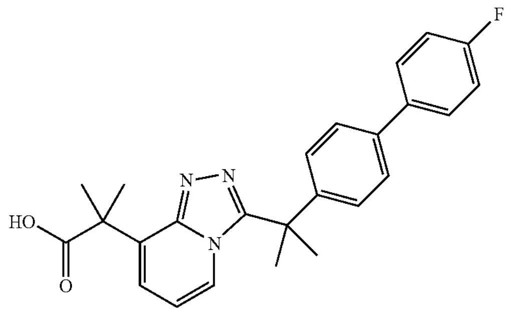 | 418 | >95 |
| 78 | 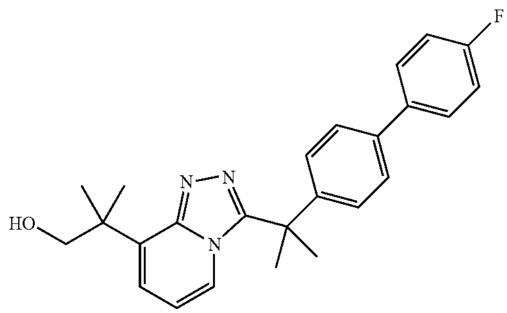 | 404 | >95 |
| 79 | 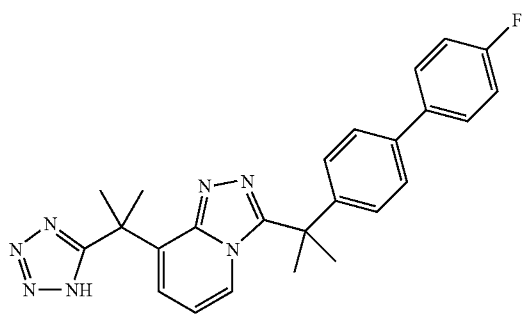 | 442 | >95 |
| 80 | 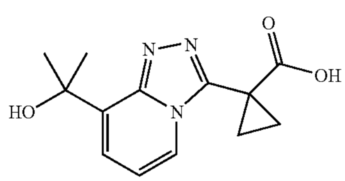 | 262 | >95 |
| 81 | 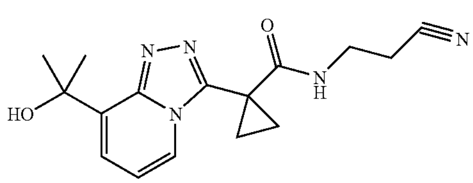 | 314 | >95 |
| 82 | 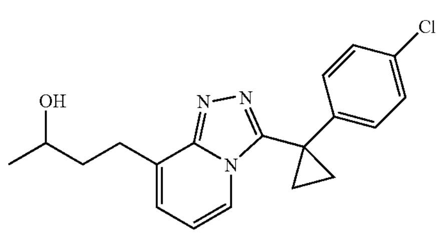 | 342 | >95 |

TABLE 4-continued

| Example | Structure | LC/MS (ES+, M + H) | HPLC purity (%) |
|---|---|---|---|
| 83 | 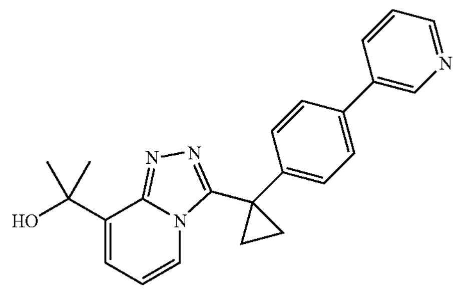 | 371 | >95 |
| 84 | 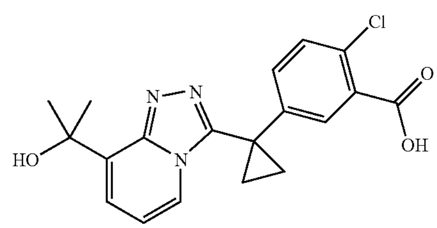 | 372 | >95 |
| 85 | 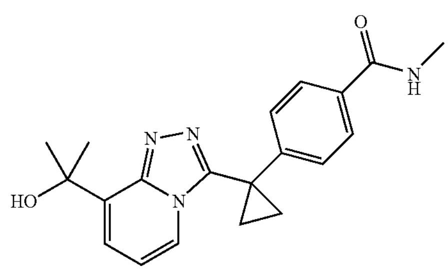 | 351 | >95 |
| 86 | 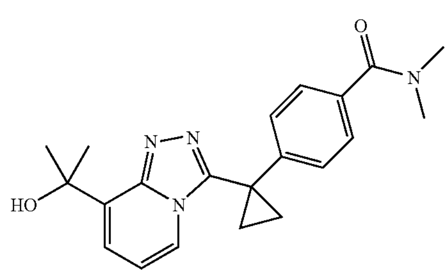 | 365 | >95 |
| 87 | 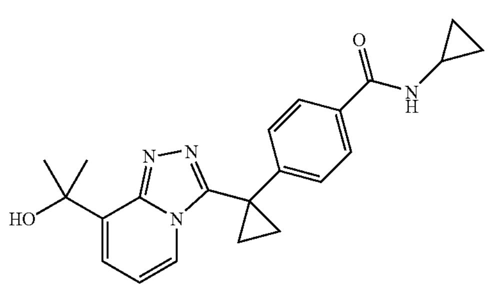 | 377 | >95 |

TABLE 4-continued

| Example | Structure | LC/MS (ES+, M + H) | HPLC purity (%) |
|---|---|---|---|
| 88 | 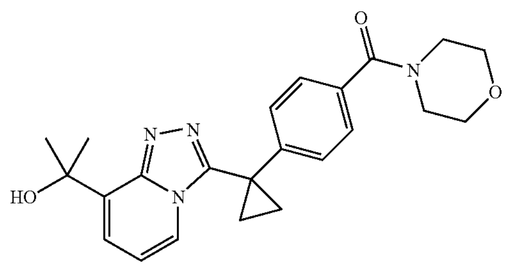 | 407 | >95 |
| 89 | 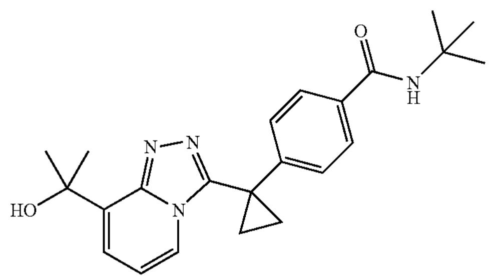 | 393 | >95 |
| 90 | 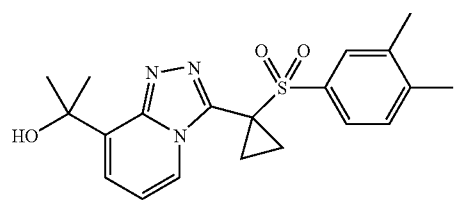 | 386 | >95 |
| 91 | 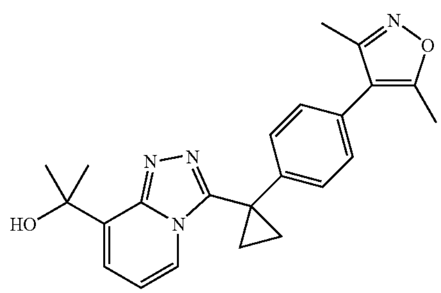 | 389 | >95 |
| 92 | 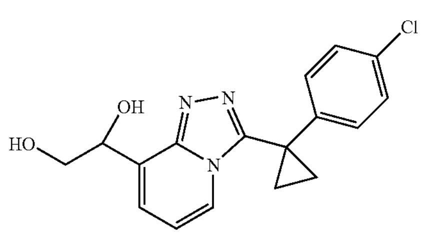 | 330 | >95 |
| 93 | 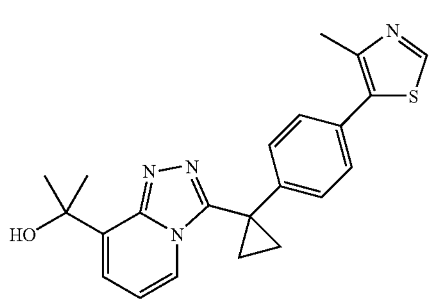 | 391 | >95 |

TABLE 4-continued

| Example | Structure | LC/MS (ES+, M + H) | HPLC purity (%) |
|---|---|---|---|
| 94 | 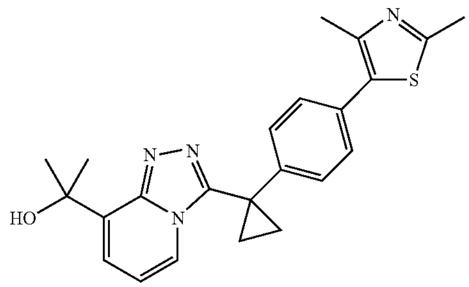 | 405 | >95 |
| 95 | 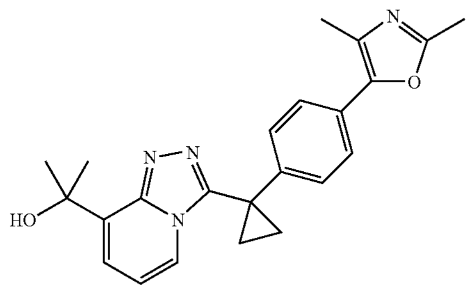 | 389 | >95 |
| 96 | 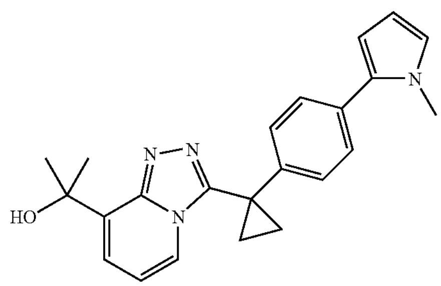 | 373 | >95 |
| 97 | 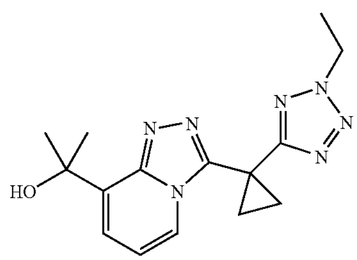 | 314 | >95 |
| 98 | 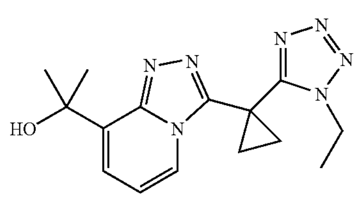 | 314 | >95 |
| 99 | 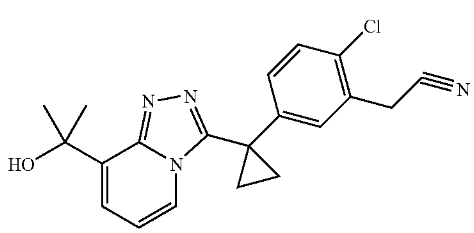 | 367 | >95 |

TABLE 4-continued

| Example | Structure | LC/MS (ES+, M + H) | HPLC purity (%) |
|---|---|---|---|
| 100 | 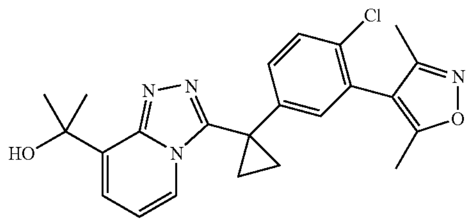 | 423 | >95 |
| 101 | 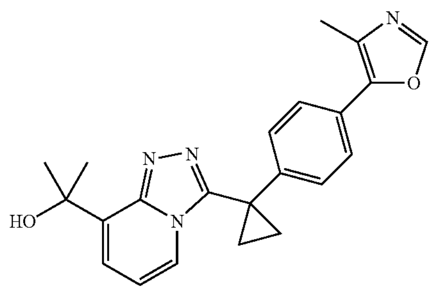 | 375 | >95 |
| 102 | 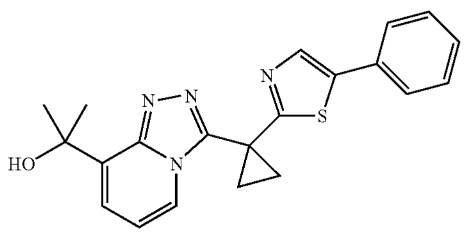 | 377 | >95 |
| 103 | 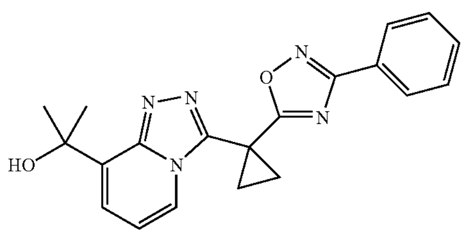 | 362 | >95 |
| 104 | 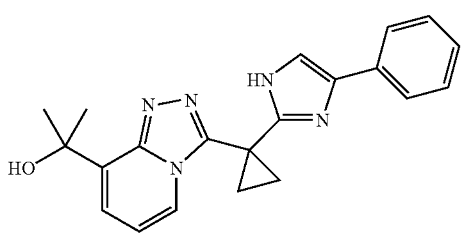 | 360 | >95 |
| 105 | 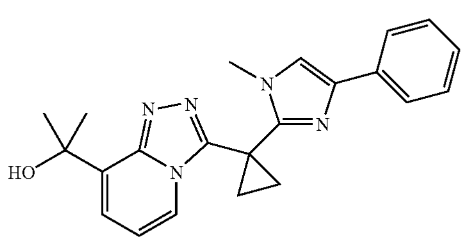 | 374 | >95 |

TABLE 4-continued

| Example | Structure | LC/MS (ES+, M + H) | HPLC purity (%) |
|---|---|---|---|
| 106 | 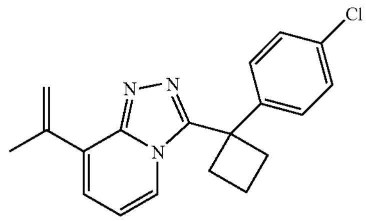 | 324 | >95 |
| 107 | 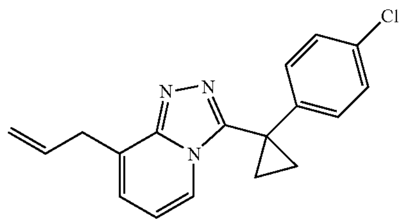 | 310 | >95 |
| 108 | 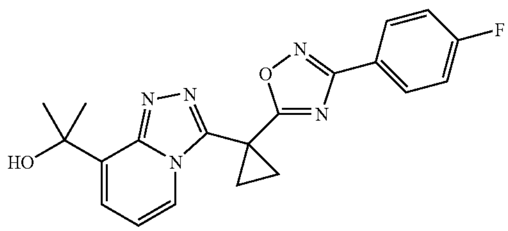 | 380 | >95 |
| 109 | 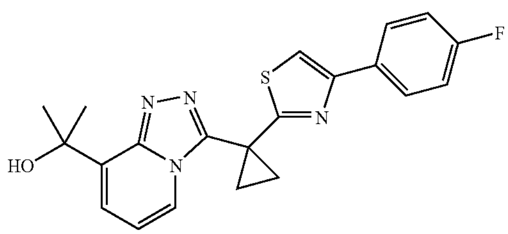 | 395 | >95 |
| 110 | 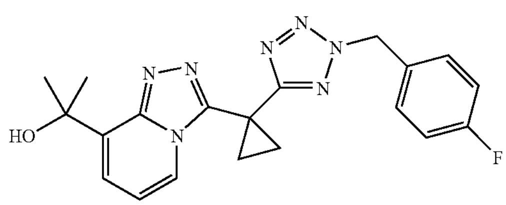 | 394 | >95 |
| 111 | 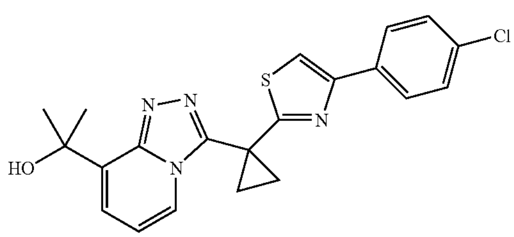 | 411 | >95 |
| 112 | 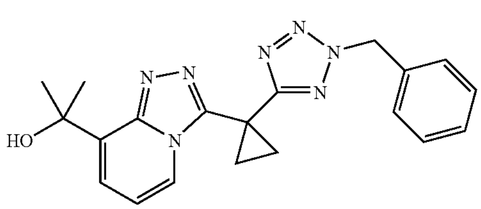 | 376 | >95 |

TABLE 4-continued

| Example | Structure | LC/MS (ES+, M + H) | HPLC purity (%) |
|---|---|---|---|
| 113 | 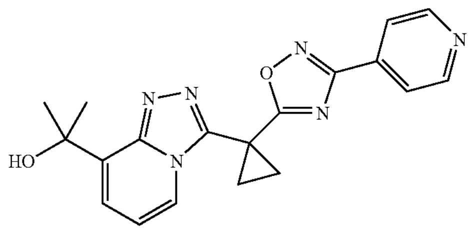 | 363 | >95 |
| 114 | 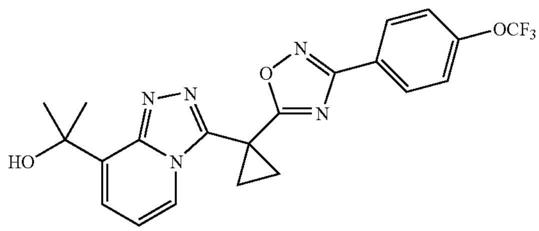 | 446 | >95 |
| 115 | 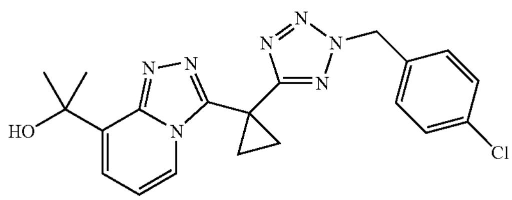 | 410 | >95 |
| 116 | 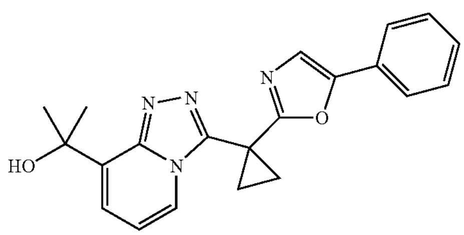 | 361 | >95 |
| 117 | 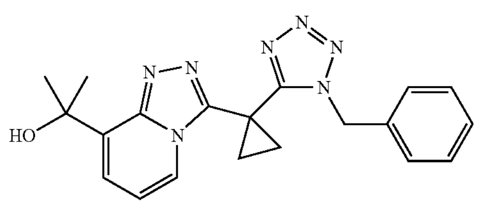 | 376 | >95 |
| 118 | 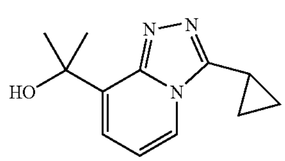 | 218 | >95 |
| 119 | 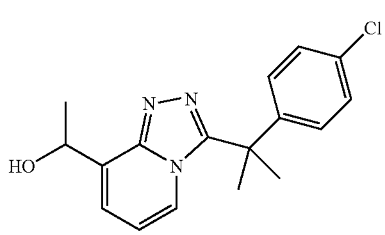 | 316 | >95 |

Assay(s) for 11-Beta-Hydroxysteroid Dehydrogenase Activity

The in vitro inhibition of recombinant human 11beta-HSD1 was determined as follows.

[$^3$H]-Cortisone with a specific radioactivity of 50 Ci/mmol (ART 743, Lot: 050906) was from American Radiolabeled Chemicals, Inc. (St Louis, Mo.); monoclonal ab to Cortisol (P01-9294M-P, Lot: L-28) was from East Coast Bio., (North Berwick, Me.); Protein A-yttrium silicate, type-1, SPA bead NJ® (RPN-143) was from Amersham LifeSciences, (Piscataway, N.J.); 384 well-Optiplate384® (#6007299) was from PerkinElmer (Boston, Mass.); DPBS, pH 7.4 (14040) is from GIBCO, (Grand Island, N.Y.); carbenoxolone (C4790) is from Sigma, (St Louis, Mo.).

Full length recombinant human 11β-HSD1 cDNAs and the cDNA encoding human 11β-HSD2 were expressed stably in HEK 293 EBNA cells. Cells were grown in DMEM (high glucose) containing MEM non-essential amino acids, L-glutamine, hygromycin B (200 µg/ml), and G-418(200 µg/ml) in the presence of 10% FBS.

Human 11β-HSD1 transfected HEK 293 EBNA cells were grown to 80% confluency and the cell pellet was quick frozen and stored at −80° C. before purification. Cell paste, 40 g from −80° C. storage, was thawed in water and then 100 ml of homogenization buffer H (0.01 M sodium phosphate pH 6.5 containing 0.25 M sucrose and protease inhibitor cocktail (Roche #1836145 1 tablet per 50 ml) were added to completely thaw the paste. The cell paste suspension was homogenized using a Polytron for 20 seconds to create a homogeneous mixture. Additional buffer H was added to a volume of 300 ml and cells were broken open using a N2-bomb (at 4° C.) in two batches by treating at 500 psi. The extract was centrifuged at 750×g for 30 min. The supernatant was centrifuged at 20,000×g for 30 min. The supernatant was further centrifuged at 105,000×g for 60 min. The 105,000×g pellet was resuspended in buffer H and centrifuged at 105,000×g for 60 min. The microsome pellet was scraped from the bottom of tube and resuspended in 0.01M phosphate buffer, pH 6.5 containing protease inhibitors (Roche #1836145, 1 tablet per 50 ml). Aliquots were stored at −80° C. until needed. The protein concentration was measured by the BioRad method using BSA standard.

Compounds were dissolved in DMSO to obtain 10 mM stock concentrations. From the 10 mM stock, the compounds were diluted in DMSO to achieve the concentrations.

11β-HSD1 SPA Enzyme Assay

11β-HSD1 was assayed by Scintillation Proximity assay in a 384-well Perkin Elmer white plate. The dose response of the compounds was determined using 11 half-log dilutions of compound in DMSO in duplicate. To each well, 0.5 µl of compound dilution in DMSO were added. 15 µl of assay buffer (for blanks) or 15 µl of human microsomes in assay buffer were added next and the plates were incubated for 10 min at room temperature. The final microsomal protein concentration was 1.1 µg/assay. Duplicates were in the same plate one row below the other. 10 µl of $^3$H-cortisone (final concentration 40 nM) was added to each well and the plate was spun down to mix and bring down the contents to the bottom of the wells. The plates were incubated at room temperature with gentle shaking for 4 hrs. The reaction was stopped with addition of 10 µl of 10 mM carbenoxolone. Then, 0.5 mg of yttrium silicate SPA beads coupled to anti-cortisol antibody in 20 µl were added to all the wells of plate, which were spun down once more and incubated at room temperature overnight. The plate was read in a TopCount® (1 min/well). Data were uploaded automatically to Tool Set, a Lead Evaluation informatics program for data capture and calculation. Graphs were generated with the Curve Master program.

Compounds of the present invention were tested in the assay described immediately above and the results shown in the Table 5 below were obtained.

TABLE 5

| Example | h HSD1 IC$_{50}$ (nM) |
| --- | --- |
| 1 | 2.3 |
| 6 | 20 |
| 42 | 72 |
| 51 | 0.4 |
| 54 | 0.7 |
| 59 | 5495 |
| 72 | 0.5 |
| 80 | 7703 |
| 86 | 35 |
| 90 | 1382 |
| 104 | 191 |
| 109 | 0.6 |
| 110 | 104 |
| 111 | 0.5 |
| 112 | 2822 |

The in vivo inhibition of recombinant human 11beta-HSD1 was determined as follows.

Studies were conducted utilizing diet induced obese (DIO) mice obtained from Jackson Laboratory (ME, USA). These mice were fed a 60% fat diet (Research Diets D12492) soon after weaning and kept on this diet for 24 weeks. These mice were individually housed. All mice were housed under controlled temperature (23° C.) and lighting (12 hours of light between 6 am to 6 pm, 12 hours of dark) with free access to water. The animals continued on this diet and were utilized for experimentation at 30 to 32 weeks of age, at which time these mice weighed 45 to 55 grams.

The basic model of 11-dehydrocorticosterone (DHC) administration to mice to produce corticosterone has been reported in the literature for clinical and preclinical evaluation of the activity of 11β-HSD. Essentially DHC (Steraloids Inc., Newport R.I.), was suspended in the vehicle at a concentration of 10 mg/kg in a volume of 7.5 ml/kg of mouse body weight. For a typical study, non-fasting mice were weighed and separated into groups (n=6) where body weights are not statistically different from each other. Animals were bled via a tail knick, for a 0 time sample and then dosed orally (7.5 ml/kg) with vehicle or drug. At 60 minutes post administration of vehicle or compound, mice were bled again via the tail tip and dosed orally (7.5 ml/kg) with DHC 10 mg/kg. All animals were subsequently bled at 30, 60 and 120 minutes post DHC dosing. Thirty-five microliters of whole blood are collected per time point in microvette tubes coated with EDTA (Sarstedt Tubes Microvette CB 300/Haematology Potassium EDTA #16.444.300) and kept on ice. Samples were centrifuged at 4° C. in a Beckman Coulter centrifuge for 10 minutes at 2500 RPM. Plasma was separated and collected and immediately frozen at −20° C. until corticosterone analysis could be assessed.

Plasma Corticosterone was measured using an EIA (IDS AC-14F1). Samples were measured at (1:2) for the −30(or −60 minute) and 0 time point and (1:10) for the 30, 60 and 120 minutes time points. AUC was calculated using Graphpad and the zero timepoint was used as the baseline. One way ANOVA was calculated using Sigmastat. A p value of less that 0.05 via post hoc analysis with Dunnett's was used to determine statistical significance.

The vehicle utilized for the suspension of the compounds was 0.5% methocel; 0.1% tween 80 in water. Methocel Cellulose (M-0262) was purchased from Sigma-Aldrich, St Louis, Mo. 6. Tween 80 (274364) was purchased from Sigma-Aldrich, St Louis, Mo. Compounds were administered in 7.5 ml/kg volumes at final dosages of 0.1 to 300 mg/kg depending on the study and compound evaluated.

Compound(s) of the present invention were tested in the assay described immediately above and the results shown in the Table 6 below were obtained.

TABLE 6

| Example | Dose | % inhibition |
|---------|------|--------------|
| 1 | 30 mpk | 53 |
| 11 | 30 mpk | 69 |

Utilities and Combinations

A. Utilities

The compounds of the present invention possess activity as inhibitors of the enzyme 11-beta-hydroxysteroid dehydrogenase type I, and, therefore, may be used in the treatment of diseases associated with 11-beta-hydroxysteroid dehydrogenase type I activity. Via the inhibition of 11-beta-hydroxysteroid dehydrogenase type I, the compounds of the present invention may preferably be employed to inhibit or modulate glucocorticoid production, thereby interrupting or modulating cortisone or cortisol production.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermittent claudication), abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

Metabolic Syndrome or "Syndrome X" is described in Ford et al., *J. Am. Med. Assoc.*, 287:356-359 (2002) and Arbeeny et al., *Curr. Med. Chem.-Imm., Endoc. & Metab. Agents*, 1: 1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other 11-beta-hydroxysteroid dehydrogenase type I inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dislipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, memory enhancing agents, cognition promoting agents and anti-inflammatory agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones: ciglitazone, pioglitazone, troglitazone, rosiglitazone; PPAR-gamma agonists; PPAR-alpha agonists; PPAR alpha/gamma dual agonists; SGLT2 inhibitors; dipeptidyl peptidase-IV (DPP4) inhibitors; glucagon-like peptide-1 (GLP-1) receptor agonists; aldose reductase inhibitors; RXR agonists: JTT-501, MCC-555, MX-6054, DRF2593, GI-262570, KRP-297, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's GL-262570, englitazone (CP-68722, Pfizer), or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck), as well as those disclosed by Murakami et al., "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", *Diabetes*, 47:1841-1847 (1998), and WO 01/21602, the disclosure of which is incorporated herein by reference, employing dosages as set out therein, which compounds designated as preferred are preferred for use herein.

Suitable alpha2 antagonists also include those disclosed in WO 00/59506, employing dosages as set out herein.

Suitable SGLT2 inhibitors include T-1095, phlorizin, WAY-123783, and those described in WO 01/27128.

Suitable DPP4 inhibitors include saxagliptan, sitagliptan, vildagliptin, and denagliptan.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) receptor agonists include Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™).

Other anti-diabetic agents that can be used in combination with compounds of the invention include ergoset and D-chiroinositol.

Suitable anti-ischemic agents include, but are not limited to, those described in the Physicians' Desk Reference and NHE inhibitors, including those disclosed in WO 99/43663.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., CP-529414 (Pfizer)), and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983 and 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440.

Preferred hypolipidemic agents are pravastatin, lovastatin, simvastatin, atorvastatin, fluvastatin, cerivastatin, atavastatin, and ZD-4522.

The fibric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, fenofibrate and gemfibrozil being preferred, bile acid sequestrants, such as cholestyramine, colestipol and DEAE-Sephadex (Secholex, Policexide), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in *Drugs of the Future*, 24:9-15 (1999) (Avasimibe); Nicolosi et al., "The ACAT inhibitor, Cl-1011 is effective in the prevention and regression of aortic fatty streak area in hamsters", *Atherosclerosis* (Shannon, Irel.), 137(1): 77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.,* 16(1):16-30 (1998); Smith, C. et al., "RP 73163: a bioavailable alkylsulfinyl-diphenylimidazole ACAT inhibitor", *Bioorg. Med. Chem. Lett.,* 6(1):47-50 (1996); Krause, B. R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.,* 1(3):204-25 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl] ureas with enhanced hypocholesterolemic activity", *Chemtracts: Org. Chem.,* 8(6):359-362 (1995), or TS-962 (Taisho Pharmaceutical Co. Ltd.).

The hypolipidemic agent may be an upregulator of LDL receptor activity, such as MD-700 (Taisho Pharmaceutical Co. Ltd) and LY295427 (Eli Lilly).

Examples of suitable cholesterol absorption inhibitors for use in combination with the compounds of the invention include ezetimibe (Zetia®).

Examples of suitable ileal $Na^+$/bile acid cotransporter inhibitors for use in combination with the compounds of the invention include compounds as disclosed in *Drugs of the Future,* 24:425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology,* 120:1199-1206 (1997), and Cornicelli et al., "15-Lipoxygenase and its Inhibition: A Novel Therapeutic Target for Vascular Disease", *Current Pharmaceutical Design,* 5:11-20 (1999).

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, CP-945598 (Pfizer), SR-147778 (Sanofi-Aventis), MK0364 (Merck) and those discussed in Hertzog, D. L., *Expert Opin. Ther. Patents*, 14:1435-1452 (2004).

The beta 3 adrenergic agonists which may be optionally employed in combination with compounds of the present invention include AJ9677 (Takeda/Dainippon), L750355 (Merck), or CP331648 (Pfizer), or other known beta 3 agonists, as disclosed in U.S. Pat. Nos. 5,541,204, 5,770,615, 5,491,134, 5,776,983, and 5,488,064, with AJ9677, L750, 355, and CP331648 being preferred.

Examples of lipase inhibitors which may be optionally employed in combination with compounds of the present invention include orlistat or ATL-962 (Alizyme), with orlistat being preferred.

The serotonin (and dopamine) reuptake inhibitor and/or modulator which may be optionally employed in combination with a compound of formula I may be sibutramine, topiramate (Johnson & Johnson), APD-356 (Arena) or axokine (Regeneron), with sibutramine and APD-356 being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); MCHR$_1$ antagonist (e.g., GSK 856464); galanin receptor antagonists; MCR-4 antagonists (e.g., HP-228); leptin or mimetics; urocortin mimetics, CRF antagonists, and CRF binding proteins (e.g., RU-486, urocortin).

Further, the compounds of the present invention may be used in combination with HIV protease inhibitors, including but not limited to Reyataz® and Kaletra®.

Examples of suitable memory enhancing agents, anti-dementia agents, or cognition promoting agents for use in combination with the compounds of the present invention include, but are not limited to, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, prednisone, acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha, prednisolone, methylprednisolone, dexamethazone, flucatisone, betamethasone, hydrocortisone and beclomethasone.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

What is claimed is:

1. A compound, enantiomers, diastereomers, or salts thereof, selected from the group consisting of:

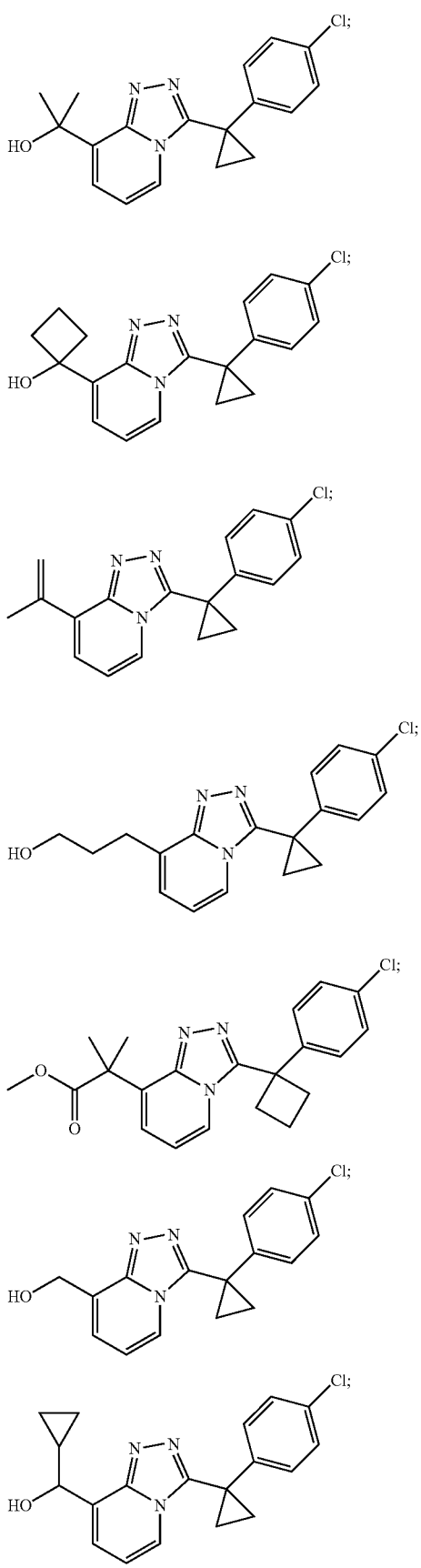
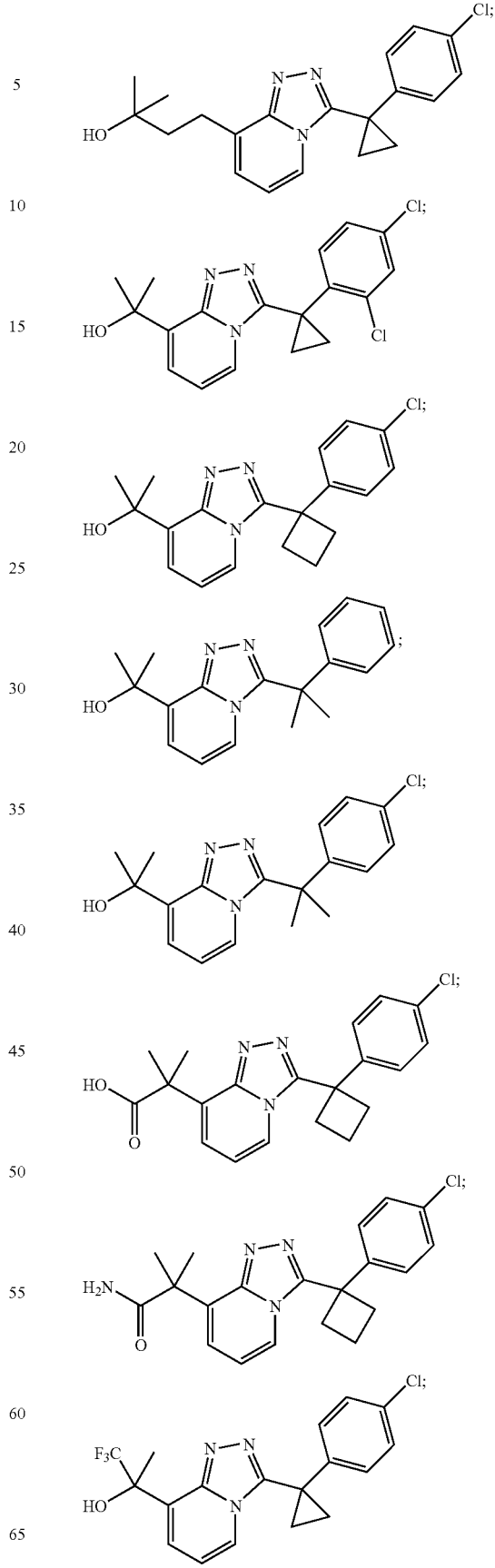

117
-continued
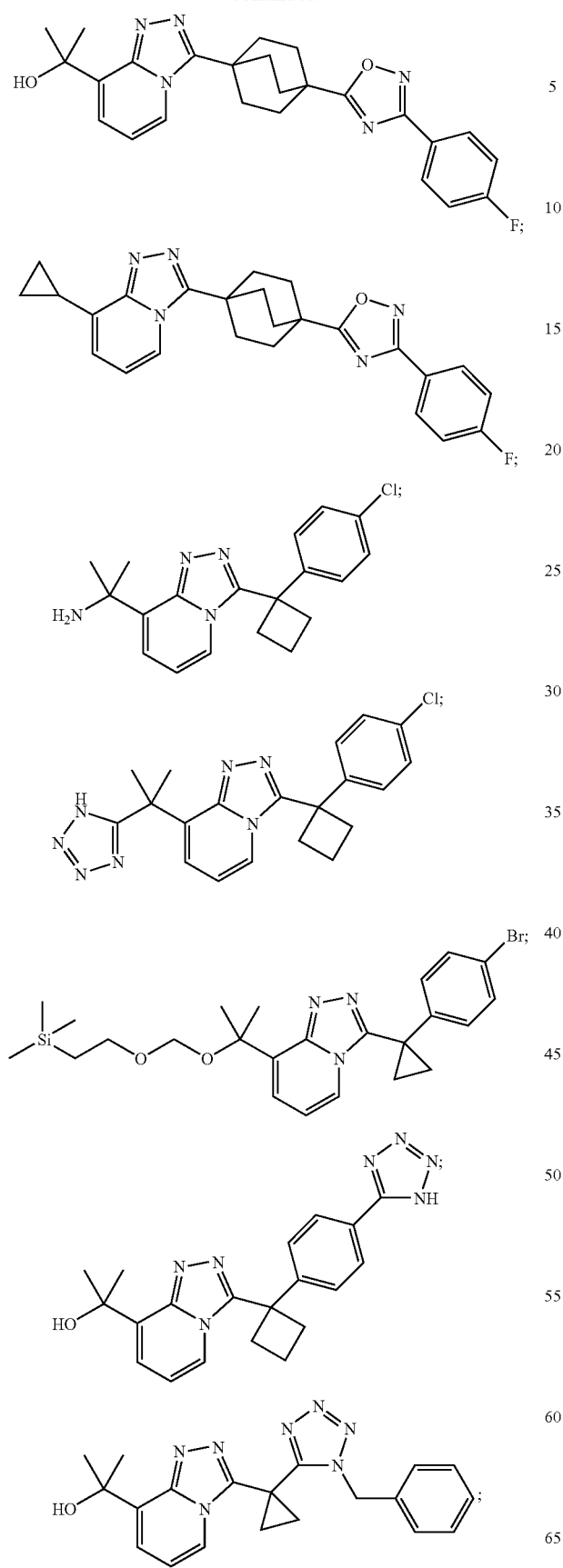
118
-continued
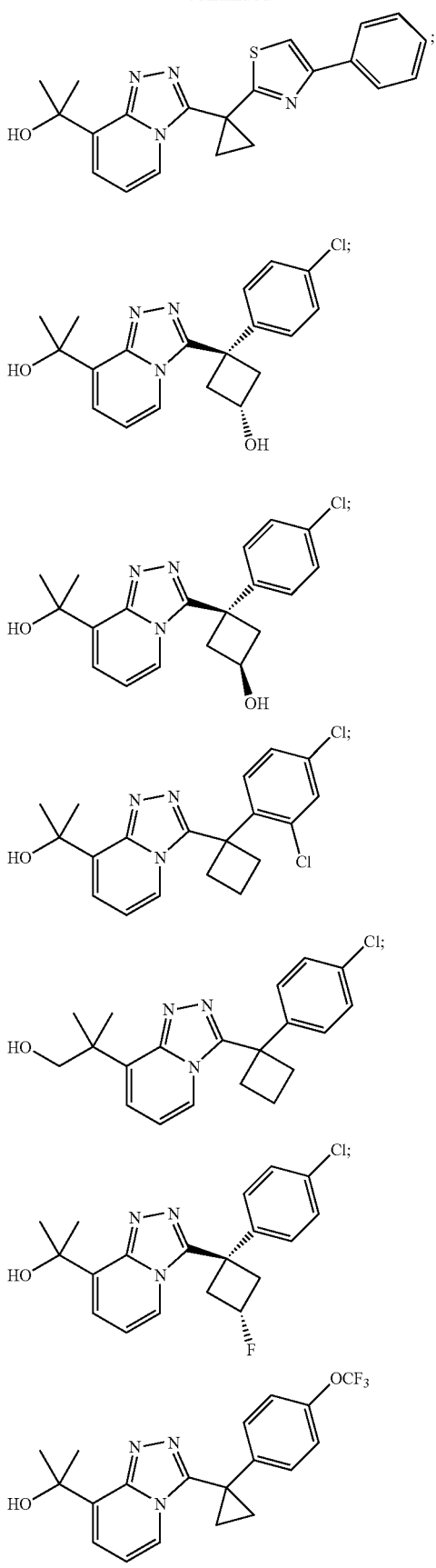

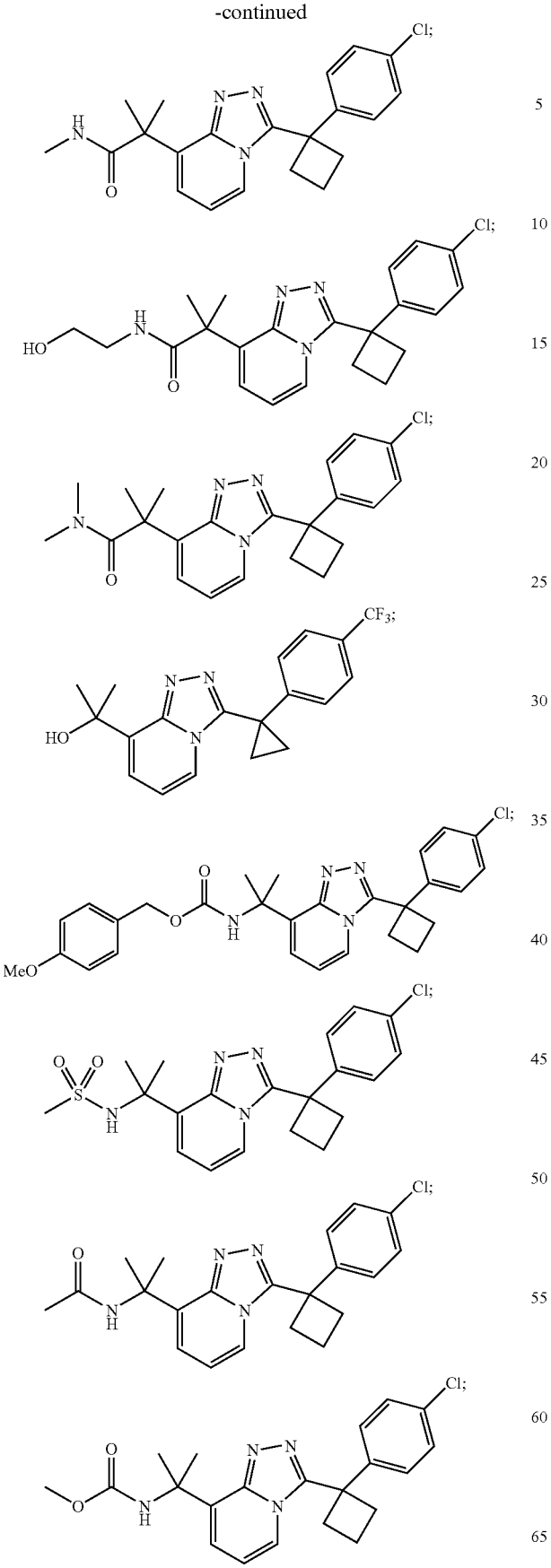

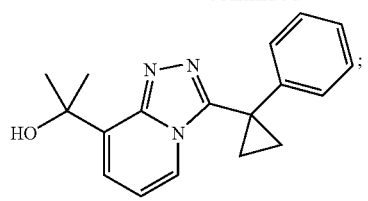
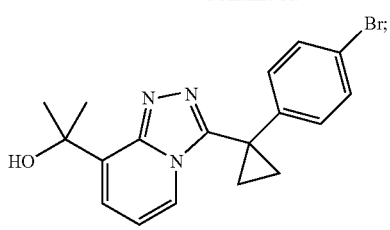
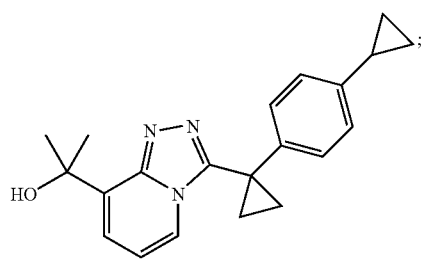
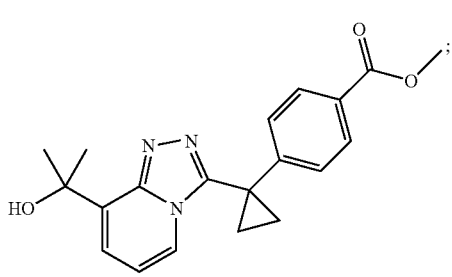
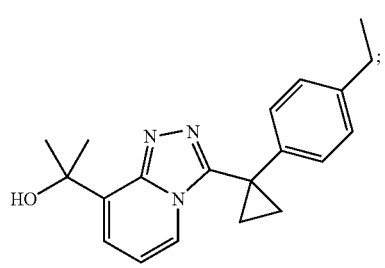
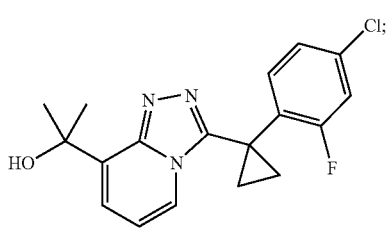
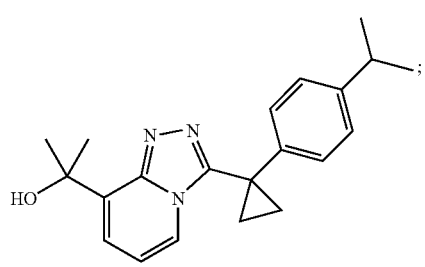
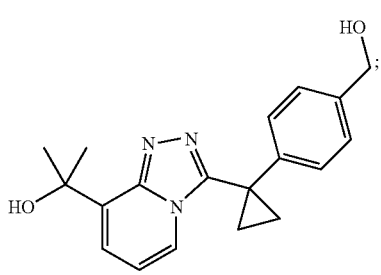
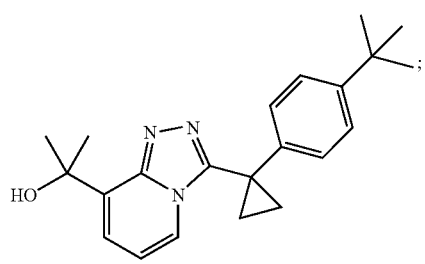
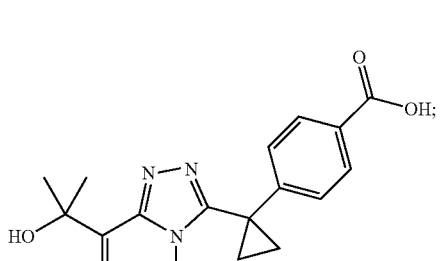
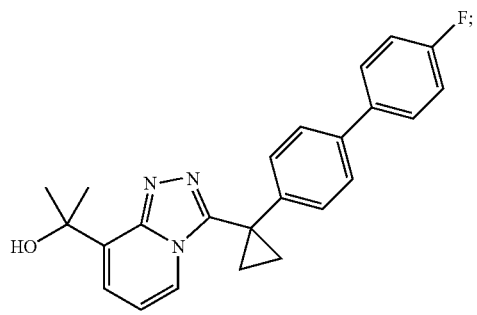
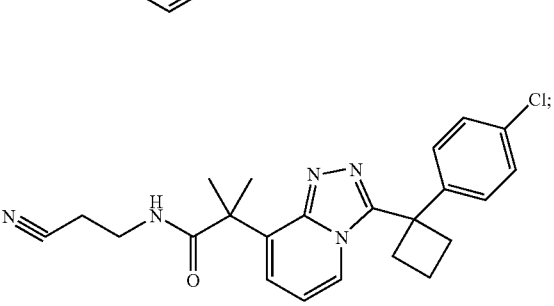

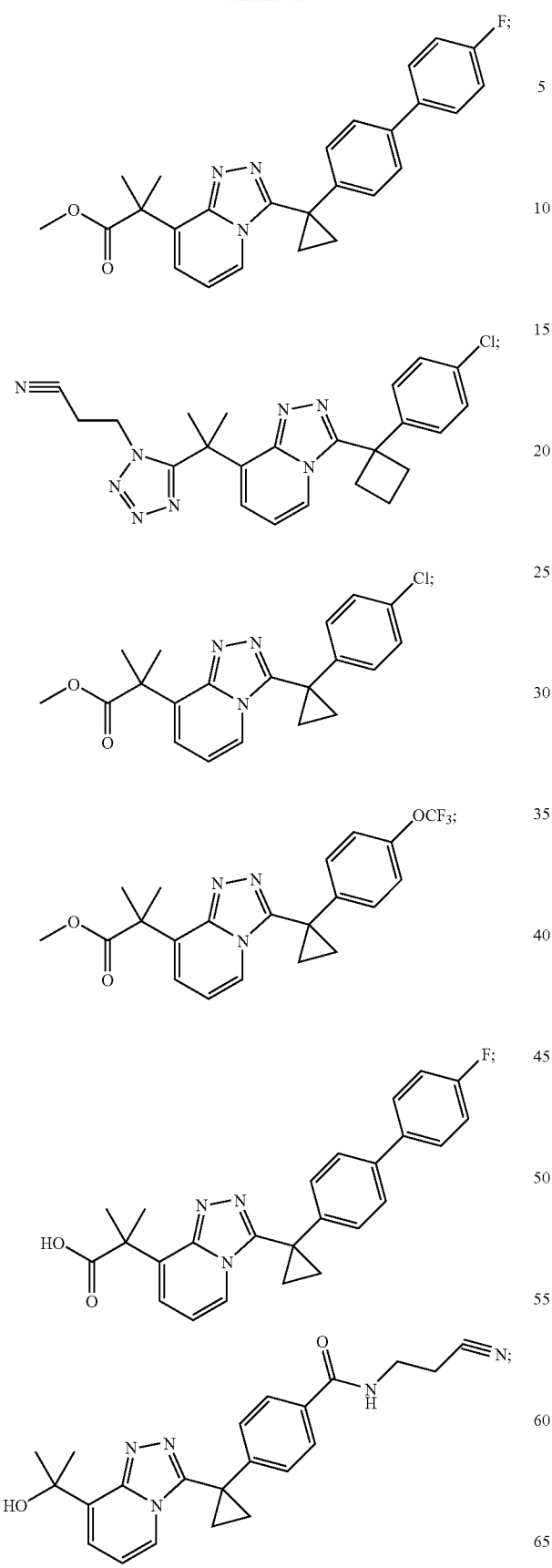
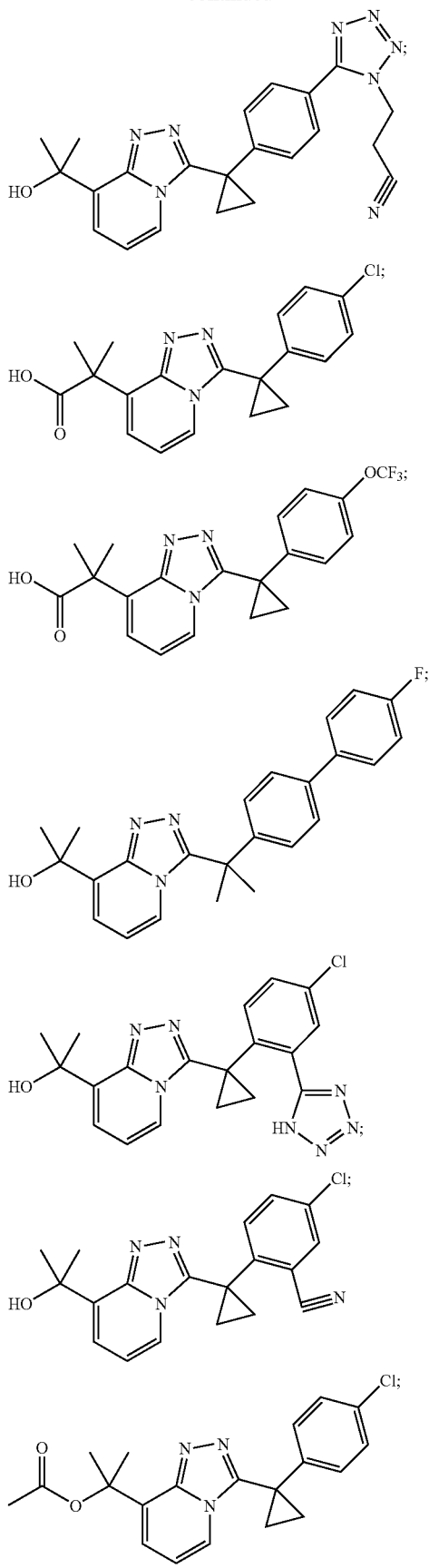

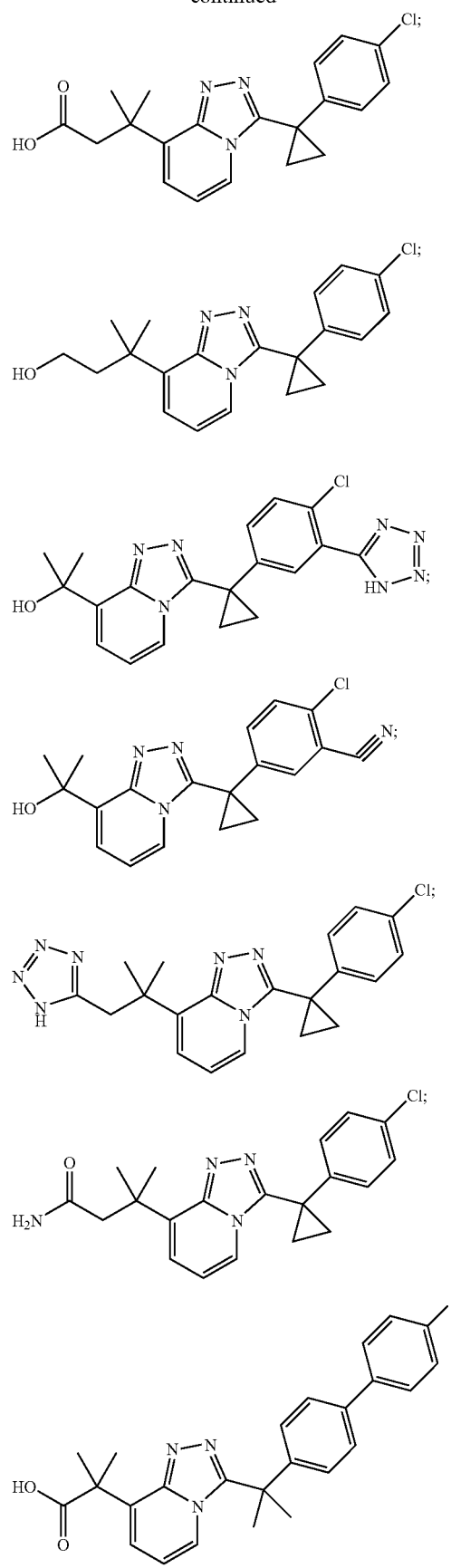
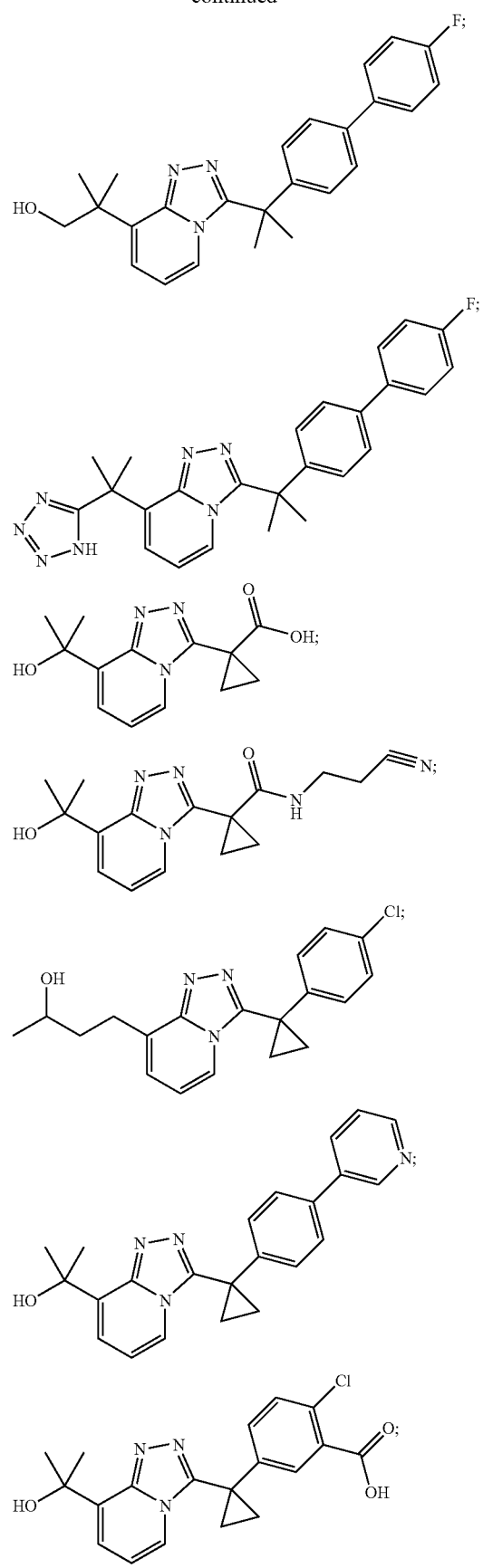

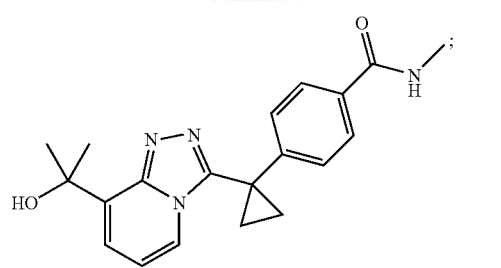
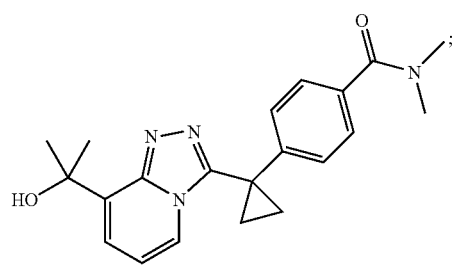
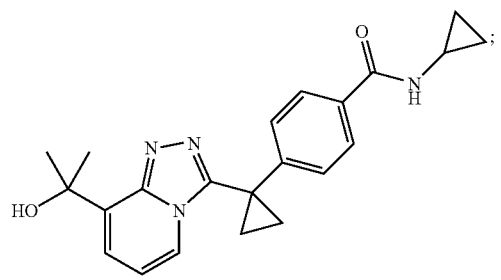
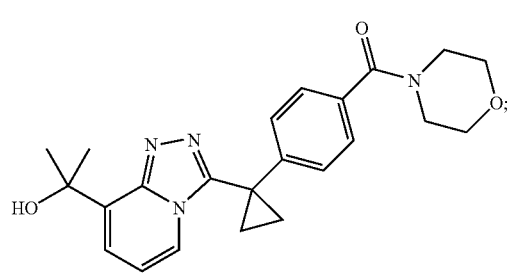
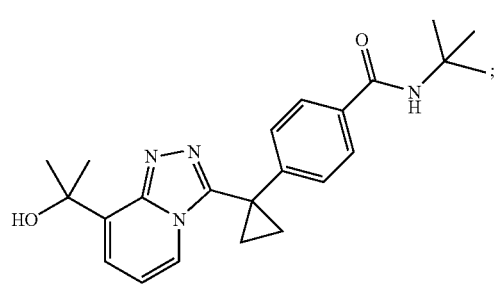
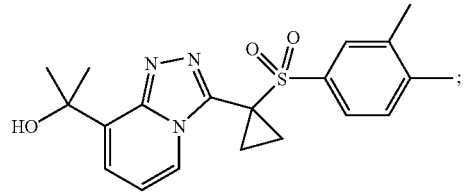
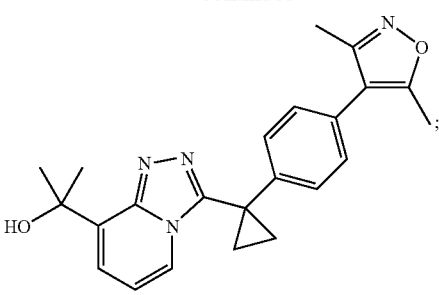
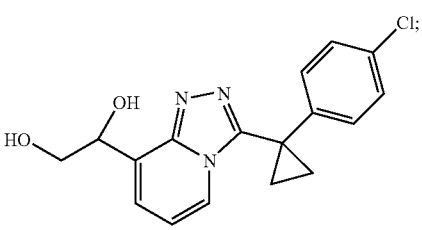
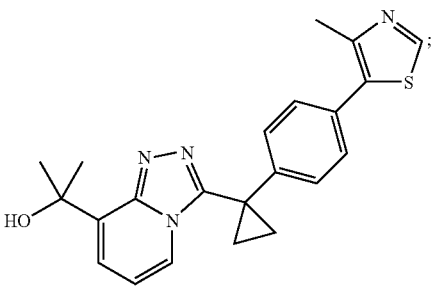
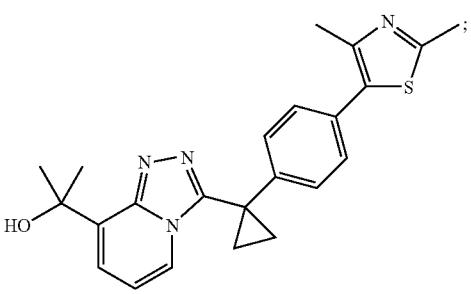
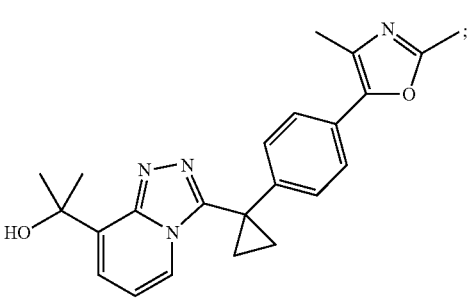
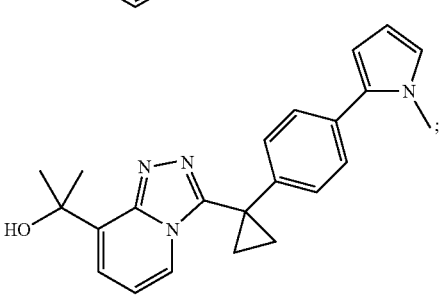

129
-continued
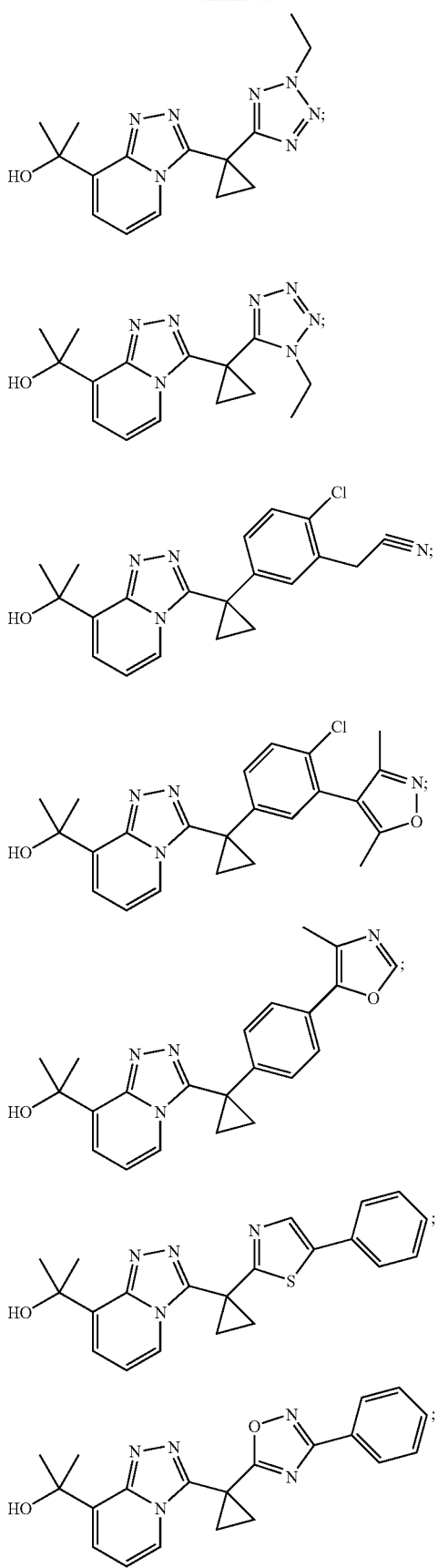
130
-continued
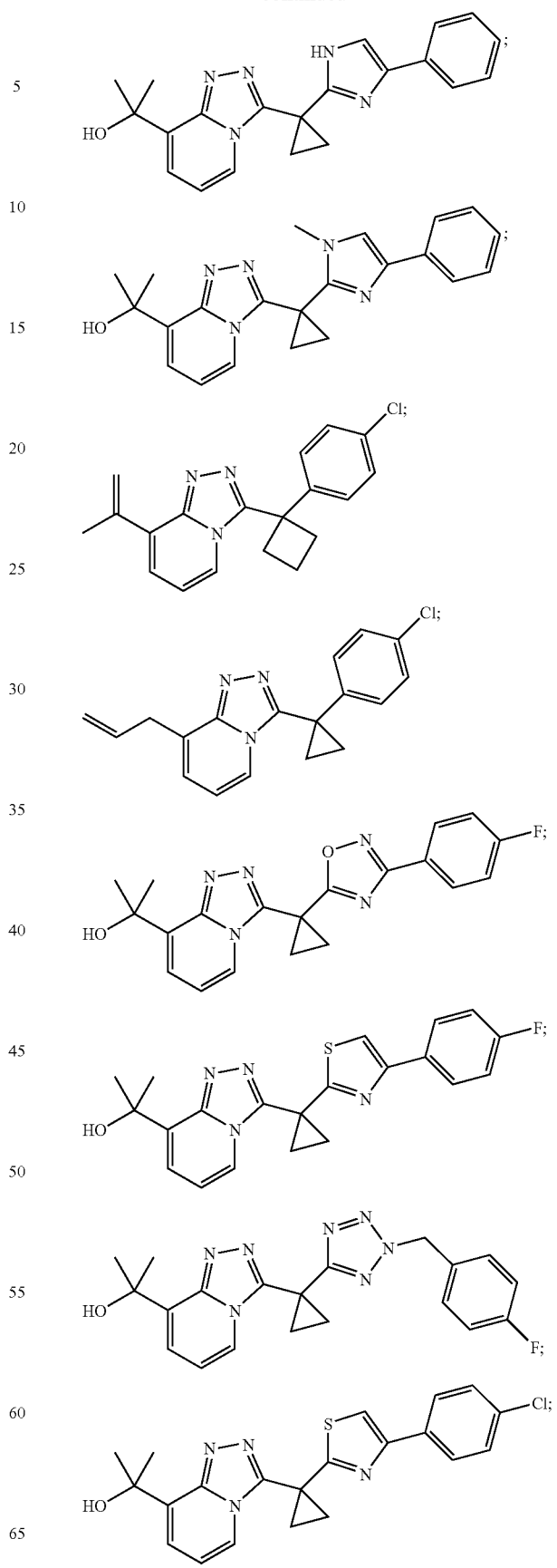

-continued

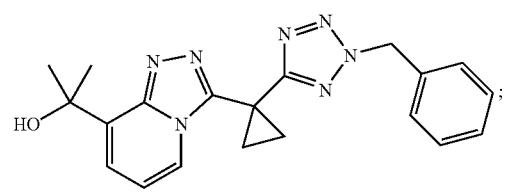

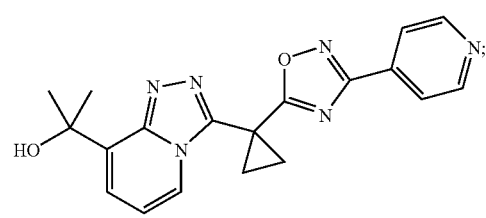

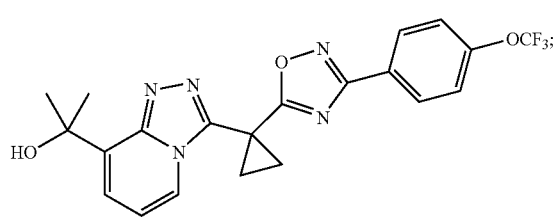

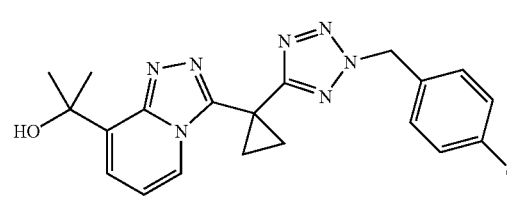

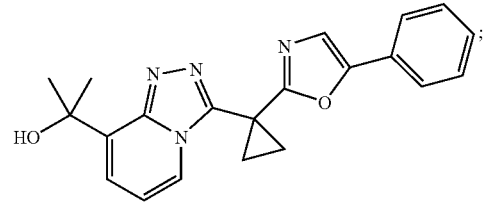

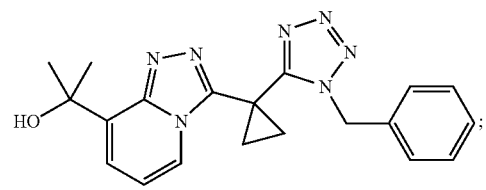

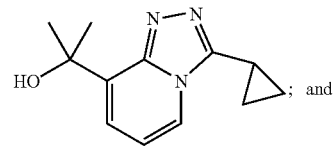; and

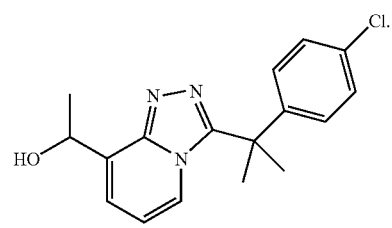

2. A compound, enantiomers, diastereomers, or salts thereof, that is

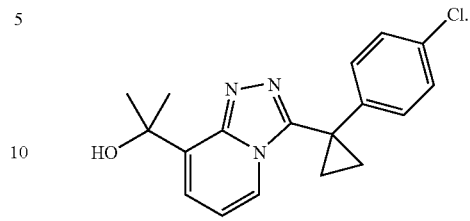

3. A compound, enantiomers, diastereomers, or salts thereof, that is

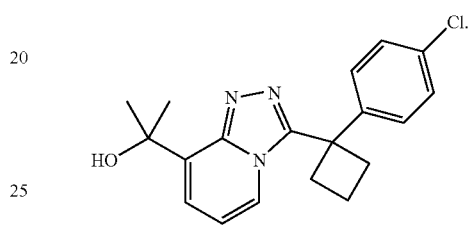

4. A compound, enantiomers, diastereomers, or salts thereof, that is

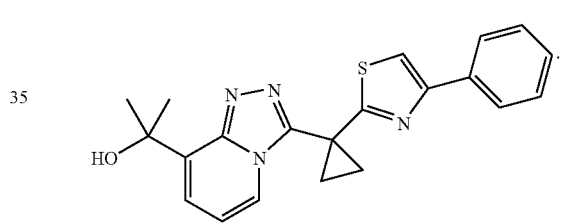

5. A compound, enantiomers, diastereomers, or salts thereof, that is

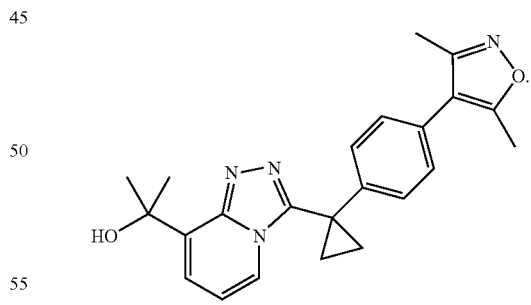

6. The compound of claim 2, wherein the compound is the hydrochloride or bisulfate salt.

7. The compound of claim 6 that is a crystalline form of said hydrochloride or bisulfate salt.

8. A pharmaceutical composition comprising a compound of claim 1.

9. The pharmaceutical composition of claim 8 further comprising a pharmaceutically acceptable carrier, and optionally at least one additional therapeutic agent.

10. A process for preparing a compound having the formula (VII-f)

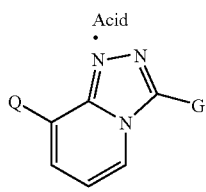

(VII-f)

comprising reacting a hydrazide of formula VII-d with a carboxylic acid or Ph₃PCl₂/diisopropyl ethylamine in the presence of a solvent at elevated temperature to afford a 1,2,4-triazolopyridine of formula VII-e and then contacting the 1,2,4-triazolopyridine of formula VII-e with an appropriate acid to provide the compound of formula (VII-f):

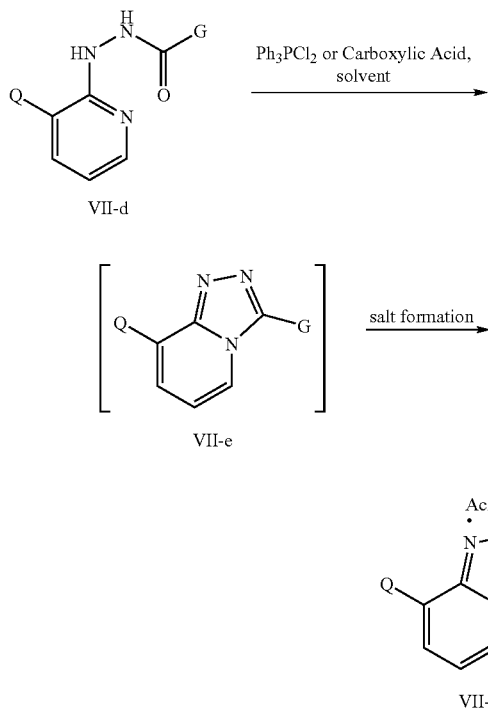

11. The process of claim 10, wherein the hydrazide of formula VII-d

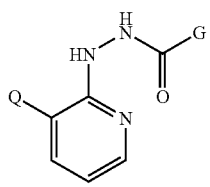

VII-d is prepared by reacting a hydrazinylpyridinyl hydrochloride of formula VII-b with an acid of formula VII-c and oxalyl chloride in a solvent in the presence of a base:

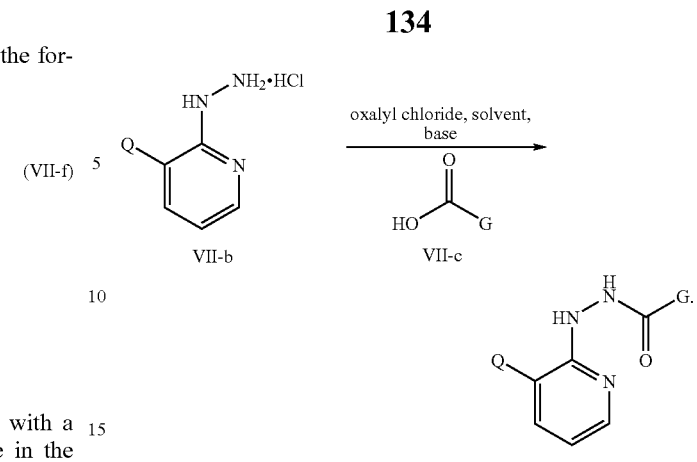

12. The process of claim 11, wherein the hydrazinylpyridinyl hydrochloride of formula VII-b

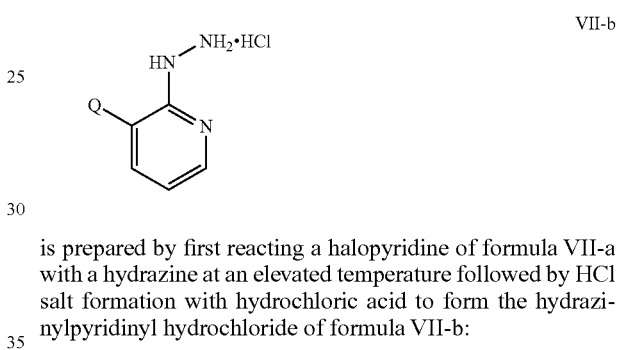

is prepared by first reacting a halopyridine of formula VII-a with a hydrazine at an elevated temperature followed by HCl salt formation with hydrochloric acid to form the hydrazinylpyridinyl hydrochloride of formula VII-b:

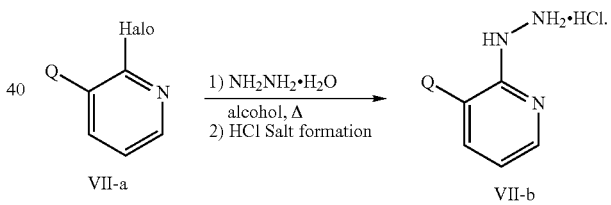

13. A pharmaceutical composition comprising a compound of claim 2.

14. The pharmaceutical composition of claim 13 further comprising a pharmaceutically acceptable carrier, and optionally at least one additional therapeutic agent.

15. A pharmaceutical composition comprising a compound of claim 3.

16. The pharmaceutical composition of claim 15 further comprising a pharmaceutically acceptable carrier, and optionally at least one additional therapeutic agent.

17. A pharmaceutical composition comprising a compound of claim 4.

18. The pharmaceutical composition of claim 17 further comprising a pharmaceutically acceptable carrier, and optionally at least one additional therapeutic agent.

19. A pharmaceutical composition comprising a compound of claim 5.

20. The pharmaceutical composition of claim 19 farther comprising a pharmaceutically acceptable carrier, and optionally at least one additional therapeutic agent.

* * * * *

UNITED STATES PATENT AND TRADEMARK OFFICE
CERTIFICATE OF CORRECTION

PATENT NO. : 8,119,658 B2
APPLICATION NO. : 12/206801
DATED : February 21, 2012
INVENTOR(S) : Jun Li et al.

Page 1 of 1

It is certified that error appears in the above-identified patent and that said Letters Patent is hereby corrected as shown below:

In the Claims:

Claim 20:

Column 134, line 64, change "farther" to -- further --.

Signed and Sealed this
Second Day of October, 2012

David J. Kappos
*Director of the United States Patent and Trademark Office*